United States Patent
Goddard, III et al.

(10) Patent No.: US 9,308,525 B2
(45) Date of Patent: Apr. 12, 2016

(54) METHODS FOR PROVIDING BOND ACTIVATION CATALYSTS AND RELATED CATALYSTS, SYSTEMS, AND METHODS

(71) Applicant: CALIFORNIA INSTITUTE OF TECHNOLOGY, Pasadena, CA (US)

(72) Inventors: William A. Goddard, III, Pasadena, CA (US); Mu-Jeng Cheng, Pasadena, CA (US); Ross Fu, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/192,856

(22) Filed: Feb. 27, 2014

(65) Prior Publication Data

US 2014/0243545 A1 Aug. 28, 2014

Related U.S. Application Data

(60) Provisional application No. 61/770,216, filed on Feb. 27, 2013.

(51) Int. Cl.
| | |
|---|---|
| *B01J 27/198* | (2006.01) |
| *B01J 27/19* | (2006.01) |
| *C07C 253/24* | (2006.01) |
| *B01J 23/00* | (2006.01) |
| *B01J 23/648* | (2006.01) |
| *B01J 23/652* | (2006.01) |
| *B01J 27/02* | (2006.01) |
| *B01J 27/057* | (2006.01) |

(52) U.S. Cl.
CPC .............. *B01J 27/198* (2013.01); *B01J 23/002* (2013.01); *B01J 23/6482* (2013.01); *B01J 23/6525* (2013.01); *B01J 27/02* (2013.01); *B01J 27/0576* (2013.01); *B01J 27/19* (2013.01); *C07C 253/24* (2013.01); *B01J 2523/00* (2013.01)

(58) Field of Classification Search
CPC ........... B01J 27/19; B01J 27/198; B01J 35/00
See application file for complete search history.

(56) References Cited

U.S. PATENT DOCUMENTS

| | | | |
|---|---|---|---|
| 4,335,018 | A | 6/1982 | Franz et al. |
| 4,515,904 | A | 5/1985 | Edwards |
| 5,281,745 | A | 1/1994 | Ushikubo et al. |
| 2004/0162217 | A1 | 8/2004 | Albonetti et al. |
| 2010/0016644 | A1 | 1/2010 | Forkner |

OTHER PUBLICATIONS

Dietl et al. "Gas-Phase Reactions of Cationic Vanadium-Phosphorus Oxide Clusters with C2Hx (x=4, 6): A DFT-Based Analysis of Reactivity Patterns" Chem. Eur. J. 2013, 19, 3017-3028 (published online Jan. 15, 2013).*
Cheng et al. "The Critical Role of Phosphate in Vanadium Phosphate Oxide for the Catalytic Activation and Functionalization of n-Butane to Maleic Anhydride" J. Am. Chem. Soc. 2013, 135, 4600-4603.*
Back et al. "N-Heterocyclic carbenes versus transition metals for stabilizing phosphinyl radicals" Chem. Sci. 2011, 2, 858-861.*
Agaral et al. "An Isolable and Monomeric Phosphorus Radical That Is Resonance-Stabilized by the Vanadium(IV/V) Redox Couple" Angew. Chem. Int. Ed. 2007, 46, 3111-3114.*
Brask et al. "Niobium and vanadium iminophosphinimide complexes" Chem. Commun. 2001, 1676-1677.*
Nomura et al. "Synthesis of (Imido)vanadium(V) Alkyl and Alkylidene Complexes Containing Imidazolidin-2-iminato Ligands: Effect of Imido Ligand on ROMP and 1,2-C—H Bond Activation of Benzene" Organomet. 2014, 33, 6682-6691.*
PCT International Search Report mailed on Jun. 17, 2014 issued for PCT Application PCT/US2014/019168 filed on Feb. 27, 2014 in the name of California Institute of Technology.
Cheng et al., The Critical Role of Phosphate in Vanadium Phosphate Oxide for the Catalytic Activation and Functionalization of n-Butane to Maleic Anhydride, JACS 2013, 135: 4600-4603.
Hodnett, B.K., "Heterogeneous catalytic oxidation: fundamental and technological aspects of the selective and total oxidation of organic compounds". 2000: Wiley New York. (Book).
Fletcher, R., "Practical Methods of Optimization" 1987, New York: Wiley. (Book).
Ballarini, N., et al., "VPO catalyst for n-butane oxidation to maleic anhydride: A goal achieved, or a still open challenge?" *Topics in catalysis* 2006 38(1-3): 147-156.
Centi, G., et al., "Mechanistic aspects of maleic anhydride synthesis from $C_4$ hydrocarbons over phosphorus vanadium oxide." *Chemical Reviews* 1988 88(1): 55-80.
Cheng, M.J., et al., "The magnetic and electronic structure of vanadyl pyrophosphate from density functional theory." *Phys Chem Chem Phys* 2011 13(20): 9831-9838.
Thompson, D.J., et al., "Modelling the active sites in vanadyl pyrophosphate." *Journal of Molecular Catalysis A: Chemical* 2003 198(1): 125-137.
Haras, A., et al., "Changes of local electronic structure of perfect $(VO)_2P_2O_7(100)$ surface in response to oxygen vacancy formation: effect of electron trapping." *Surface science* 2002 513(2): 367-380.
Robert, V., et al., "Role of mixed-valence state in vanadium phosphates catalysts." *Journal of Molecular Catalysis A: Chemical* 1997 119(1): 327-333.
Schiøtt, B., et al., "Formation of maleic anhydride on a vanadyl pyrophosphate surface: a theoretical study of the mechanism." *The Journal of Physical Chemistry* 1991 95(6): 2297-2307.
Gleaves, J., et al., "Temporal analysis of products (TAP)—a unique catalyst evaluation system with submillisecond time resolution." *Catalysis Reviews Science and Engineering* 1988 30(1): 49-116.
Zhang-Lin, Y., et al., "On the Mechanism of *n*-Butane Oxidation to Maleic Anhydride on VPO Catalysts: I. A Kinetics Study on a VPO Catalyst as Compared to VPO Reference Phases." *Journal of Catalysis* 1994 145(2): 256-266.
Agaskar, P.A., et al., "A molecular level mechanism of *n*-butane oxidation to maleic anhydride over vanadyl pyrophosphate." *Catalysis letters* 1994 23(3-4): 339-351.

(Continued)

*Primary Examiner* — Nyeemah A Grazier
*Assistant Examiner* — Amanda L Aguirre
(74) *Attorney, Agent, or Firm* — Steinfl & Bruno LLP

(57) ABSTRACT

Described herein are catalysts for activation of an R—H bond in a R—H substrate and related catalytic matrices, compositions, methods and systems.

9 Claims, 34 Drawing Sheets

(56) References Cited

OTHER PUBLICATIONS

Tran, T., et al., "Differing Reactions of Functionalized Hydrocarbons with Cp*M (NO)(alkyl)($\eta^3$-allyl) Complexes of Molybdenum and Tungsten." *Organometallics* 2011 30(4): 738-751.

Blanksby, S.J., et al., "Bond dissociation energies of organic molecules." *Acc Chem Res* 2003 36(4): 255-263.

Volta, J.-C., "Dynamic processes on vanadium phosphorous oxides for selective alkane oxidation." *Catalysis today* 1996 32(1): 29-36.

Hutchings, G.J., et al., "Role of the product in the transformation of a catalyst to its active state." *Nature* 1994 368(6466): 41-45.

Shimoda, T., et al., "Preparation of Vanadium-Phosphorus Mixed Oxide (P/V=1) Catalysts and Their Application to Oxidation of Butane to Maleic Anhydride." *Bulletin of the Chemical Society of Japan* 1985 58(8): 2163-2171.

Koyano, G., et al., "Structural Changes of Surface Layer of Vanadyl Pyrophosphate Catalysts by Oxidation—Reduction and Their Relationships with Selective Oxidation of *n*-Butane." *Journal of the American Chemical Society* 1998 120(4): 767-774.

Perdew, J.P., et al., "Generalized gradient approximation made simple." *Physical review letters* 1996 77(18): 3865-3868.

Vanderbilt, D., "Soft self-consistent pseudopotentials in a generalized eigenvalue formalism." *Phys Rev B Condens Matter* 1990 41(11): 7892-7895.

Monkhorst, H.J., et al., "Special points for Brillouin-zone integrations." *Physical Review B* 1976 13(12): 5188-5192.

Henkelman, G., et al., "Improved tangent estimate in the nudged elastic band method for finding minimum energy paths and saddle points." *The Journal of Chemical Physics* 2000 113(22): 9978-9985.

Henkelman, G., et al., "A climbing image nudged elastic band method for finding saddle points and minimum energy paths." *The Journal of Chemical Physics* 2000 113(22): 9901-9904.

Saito, T., et al., "Single Crystal Growth of the High Pressure Phase of $(VO)_2P_2O_7$ at 3 GPa." *Journal of Solid State Chemistry* 2000 153(1): 124-131.

Geupel, S., et al., "Synchrotron-radiation study of the two-leg spin ladder $(VO)_2P_2O_7$ at 120 K." *Acta Crystallographica Section C Crystal Structure Communications* 2002 58(4): e10-e10. (12 pages total).

Grimme, S., "Semiempirical GGA-type density functional constructed with a long-range dispersion correction." *J Comput Chem* 2006 27(15): 1787-1799.

Hehre, W.J., et al., "Self—Consistent Molecular Orbital Methods. XII. Further Extensions of Gaussian—Type Basis Sets for Use in Molecular Orbital Studies of Organic Molecules." *The Journal of Chemical Physics* 1972 56(5): 2257-2261.

Francl, M.M., et al., "Self-consistent molecular orbital methods. XXII. A polarization-type basis set for second-row elements." *The Journal of Chemical Physics* 1982 77(7): 3654-3665.

Hay, P.J., et al., "*Ab initio* effective core potentials for molecular calculations. Potentials for K to Au including the outermost core orbitals." *The Journal of Chemical Physics* 1985 82(1): 299-310.

Busca, G., et al., "Surface acidity of vanadyl pyrophosphate, active phase in *n*-butane selective oxidation." *The Journal of Physical Chemistry* 1986 90(7): 1337-1344.

Yin, X., et al., "Reactivity of lattice oxygens present in $V_2O_5$ (010): A periodic first-principles investigation." *The Journal of Physical Chemistry B* 1999 103(8): 1263-1269.

Calatayud, M., et al., "Reactivity of the oxygen sites in the $V_2O_5/TiO_2$ anatase catalyst." *The Journal of Physical Chemistry B* 2004 108(40): 15679-15685.

Schuurman, Y., et al., "Activation of vanadium phosphorus oxide catalysts for alkane oxidation. The influence of the oxidation state on catalyst selectivity." *Industrial & engineering chemistry research* 1994 33(12): 2935-2941.

Kung, H.H., "Desirable catalyst properties in selective oxidation reactions." *Industrial & engineering chemistry product research and development* 1986 25(2): 171-178.

Joly, J., et al., "TPD study of labile oxygen on a $(VO)_2P_2O_7$ catalyst active in *n*-butane partial oxidation." *Applied Catalysis A: General* 1998 169(1): 55-63.

Ballhausen, C.J., et al., "The electronic structure of the vanadyl ion." *Inorganic Chemistry* 1962 1(1): 111-122.

Jin, N., et al., "Trans-dioxo manganese(V) porphyrins." *J Am Chem Soc* 2007 129(41): 12416-12417.

Wachs, I.E., et al., "In situ Raman spectroscopy studies of bulk and surface metal oxide phases during oxidation reactions." *Catalysis today* 1996 32(1): 47-55.

Wachs, I.E., et al., "Fundamental studies of butane oxidation over model-supported vanadium oxide catalysts: Molecular structure-reactivity relationships." *Journal of Catalysis* 1997 170(1): 75-88.

Coulston, G.W., et al., "The Kinetic Significance of $V^{5+}$ in *n*-Butane Oxidation Catalyzed by Vanadium Phosphates." *Science* 1997 275(5297): 191-193.

Xue, Z.-Y., et al., "In Situ Laser Raman Spectroscopy Studies of VPO Catalyst Transformations." *The Journal of Physical Chemistry B* 1999 103(44): 9459-9467.

Guliants, V., et al., "Evolution of the active surface of the vanadyl pyrophosphate catalysts." *Catalysis letters* 1995 32(3-4): 379-386.

Ganduglia-Pirovano, M.V., et al., "Role of ceria in oxidative dehydrogenation on supported vanadia catalysts." *J Am Chem Soc* 2010 132(7): 2345-2349.

Alptekin, G.O., et al., "Methane partial oxidation by unsupported and silica supported iron phosphate catalysts: Influence of reaction conditions and co-feeding of water on activity and selectivity." *Journal of Catalysis* 1999 181(1): 104-112.

Marcu, I.-C., et al., "Effects of the method of preparing titanium pyrophosphate catalyst on the structure and catalytic activity in oxidative dehydrogenation of *n*-butane." *Journal of Molecular Catalysis A: Chemical* 2003 203(1): 241-250.

Arnold III, E.W., et al., "Effect of water vapor on the activity and selectivity characteristics of a vanadium phosphate catalyst towards butane oxidation." *Applied catalysis* 1988 41: 225-239.

Hutchings, G.J., "Promotion in heterogeneous catalysis: a topic requiring a new approach?" *Catalysis letters* 2001 75(1-2): 1-12.

Shilov, A.E., et al., "Activation of C—H bonds by metal complexes." *Chemical Reviews* 1997 97(8): 2879-2932.

64-Baccolini, G., et al., "A New Performance of the Reaction of PCl3/AlCl3 with Anisoles—One-Pot and Multi-Step Syntheses of a New Fused-Ring System [1,2,3] Benzoxadiphospholo[2,3-b][1,2,3]benzoxadiphosphole." *European Journal of Organic Chemistry* 2001 2001(12): 2229-2233.

de Petris, G., et al., "Methane Activation by Metal-Free Radical Cations: Experimental Insight into the Reaction Intermediate." *Chemistry—A European Journal* 2009 15(17): 4248-4252.

Kubias, B., et al., "The reaction network of the selective oxidation of n-butane on $(VO)_2P_2O_7$ catalysts: Nature of oxygen containing intermediates." *Catalysis today* 1996 32(1): 243-253.

Pepera, M.A., et al., "Fundamental study of the oxidation of butane over vanadyl pyrophosphate." *Journal of the American Chemical Society* 1985 107(17): 4883-4892.

Gardner, K.A., et al., "Understanding C—H bond oxidations: H and $H^-$ transfer in the oxidation of toluene by permanganate." *Science* 1995 269(5232): 1849-1851.

Grasselli, R.K., et al., "Multifunctionality of active centers in (amm)oxidation catalysts: from Bi—Mo—$O_x$ to Mo—V—Nb—(Te, Sb)—O-$_x$." *Topics in Catalysis* 2003 23(1-4): 5-22.

Wang, C.M., et al., "Neutral nickel(II)-based catalysts for ethylene polymerization." *Organometallics* 1998 17(15): 3149-3151.

Li, X., et al., "Improvement of the Structural Model for the *M*1 Phase Mo—V—Nb—Te—O Propane (Amm)oxidation Catalyst." *Topics in Catalysis* 2011 54(10-12): 614-626.

Bauer, R.C., et al., "Pincer ligands with an all-phosphorus donor set: subtle differences between rhodium and palladium." *Dalton Trans.* 2011 40(35): 8822-8829.

Derrah, E.J., et al., "Original phenyl-P(O) bond cleavage at palladium(0): a combined experimental and computational study." *Chem. Commun.* 2011 47(30): 8611-8613.

Derrah, E.J., et al., "Chelating Assistance of P—C and P—H Bond Activation at Palladium and Nickel: Straightforward Access to Diverse Pincer Complexes from a Diphosphine-Phosphine Oxide." *Organometallics* 2013 32(4): 1121-1128.

(56) References Cited

OTHER PUBLICATIONS

Gloaguen, Y., et al., "Reactivity of a mononuclear iridium(I) species bearing a terminal phosphido fragment embedded in a triphosphorus ligand." *Inorg. Chem.* 2013 52(4): 1682-1684.

Mazzeo, M., et al., "Phosphido Pincer Complexes of Palladium as New Efficient Catalysts for Allylation of Aldehydes." *Organometallics* 2008 27(22): 5741-5743.

Mazzeo, M., et al., "Phosphido pincer complexes of platinum: synthesis, structure and reactivity." *Dalton Trans* 2011 40(35): 9026-9033.

Pan, B.F., et al., "Coordination of an N-Heterocyclic Phosphenium Containing Pincer Ligand to a Co(Co)$_2$ Fragment Allows Oxidation to Form an Unusual N-Heterocyclic Phosphinito Species." *Organometallics* 2011 30(21): 5560-5563.

Pan, B., et al., "Heterolytic addition of E—H bonds across Pt-P bonds in Pt N-heterocyclic phosphenium/phosphido complexes." *Dalton Trans* 2012 41(30): 9083-9090.

Wife, R.L., et al., "Phosphine Oxide Anions in the Synthesis of Phosphine Ligands." *Synthesis* 1983 (01): 71-73.

Baccolini, G., et al., "A New Performance of the Reaction of PCl$_3$/AlCl$_3$ with Anisoles—One-Pot and Multi-Step Syntheses of a New Fused-Ring System [1,2,3]Benzoxadiphospholo[2,3-b][1,2,3]benzoxadiphosphole." *European Journal of Organic Chemistry* 2001 (12): 2229-2233.

Kurmaev, D.A., et al., "Coordination compounds of chromium (+3) and vanadium (+3) and (+5) with 2,6-bis(diphenylhydroxymethyl)pyridyl ligand: Synthesis and study of catalytic activity in the polymerization of ethylene." *Inorganica Chimica Acta* 2013 396(0): 136-143.

Villanneau, R., et al., "Bisorganophosphonyl and -Organoarsenyl Derivatives of Heteropolytungstates as Hard Ligands for Early-Transition-Metal and Lanthanide Cations." *European Journal of Inorganic Chemistry* 2013 (10-11): 1815-1820.

Tong, L.H., et al., "The coordination chemistry of unsymmetric N-capped tripodal NO$_3$ ligands with iron(III), oxo-vanadium(V) and dioxo-molybdenum(VI) metal centres." *Inorganica Chimica Acta* 2012 383(0): 91-97.

North, M., et al., "Asymmetric cyanohydrin synthesis using an aluminium(salan) complex." *Tetrahedron: Asymmetry* 2012 23(15-16): 1218-1225.

Cao, Y., et al., "Molecular (hyper)polarizabilities computed by pseudospectral methods." *J Chem Phys* 2005 122(10): 104102, (12 pages).

Chen, B., et al., "Investigation of the mechanism of n-butane oxidation on vanadium phosphorus oxide catalysts: evidence from isotopic labeling studies" *J. Am. Chem. Soc.* 2002, 124 (8), 1638-1652.

Busca, G.; et al., "Nature and Mechanism of Formation of Vanadyl Pyrophosphate: Active Phase in n-Butane Selective Oxidation", *Journal of Catalysis*, 99 (1986) 400-414.

Written Opinion issued for PCT Application PCT/US2014/019168 filed Feb. 27, 2014 in the name of California Institute of Technology. Mailed on Jun. 17, 2014, 8 pages.

International Preliminary Report on Patentability issued for PCT Application PCT/US2014/019168 filed Feb. 27, 2014 in the name of California Institute of Technology. Mailed on Sep. 1, 2015, 9 pages.

Dietl et al. "Supporting Information" for "'Gas-Phase Reactions of Cationic Vanadium-Phosphorus Oxide Clusters with C2Hx (x=4, 6): A DFT-Based Analysis of Reactivity Patterns' Chem. Eur. J. 2013, 19, 3017-3028 (published online Jan. 15, 2013)", 2013, pp. 1-109.

\* cited by examiner (a)　　　　　　　(b)

$D_H$ (P) = 89.2    $D_H$ (As) = 79.1    $D_H$ (Sb) = 63.8    $D_H$ (Bi) = 67.9

$D_H$ (S) = 90.7    $D_H$ (Se) = 90.0    $D_H$ (Te) = 94.5

$D_H = 92.0$ (a) β-VOPO$_4$ (b) δ-VOPO$_4$ (c) α$_I$-VOPO$_4$ (d) α$_{II}$-VOPO$_4$ $\Delta E = 69.7$ kcal/mol ΔE = 77.1 kcal/mol
(18.1 for Two-Layer Model)

ΔE = 68.8 kcal/mol
(48.4 from Two-Layer Model)

ΔE = 77.4 kcal/mol

ΔE = 78.4 kcal/mol

ΔE = -85.8 kcal/mol

ΔE = -82.0 kcal/mol

ΔE = 80.1 kcal/mol

ΔE = 71.0 kcal/mol

ΔE = 27.2 kcal/mol

ΔE = 47.2 kcal/mol

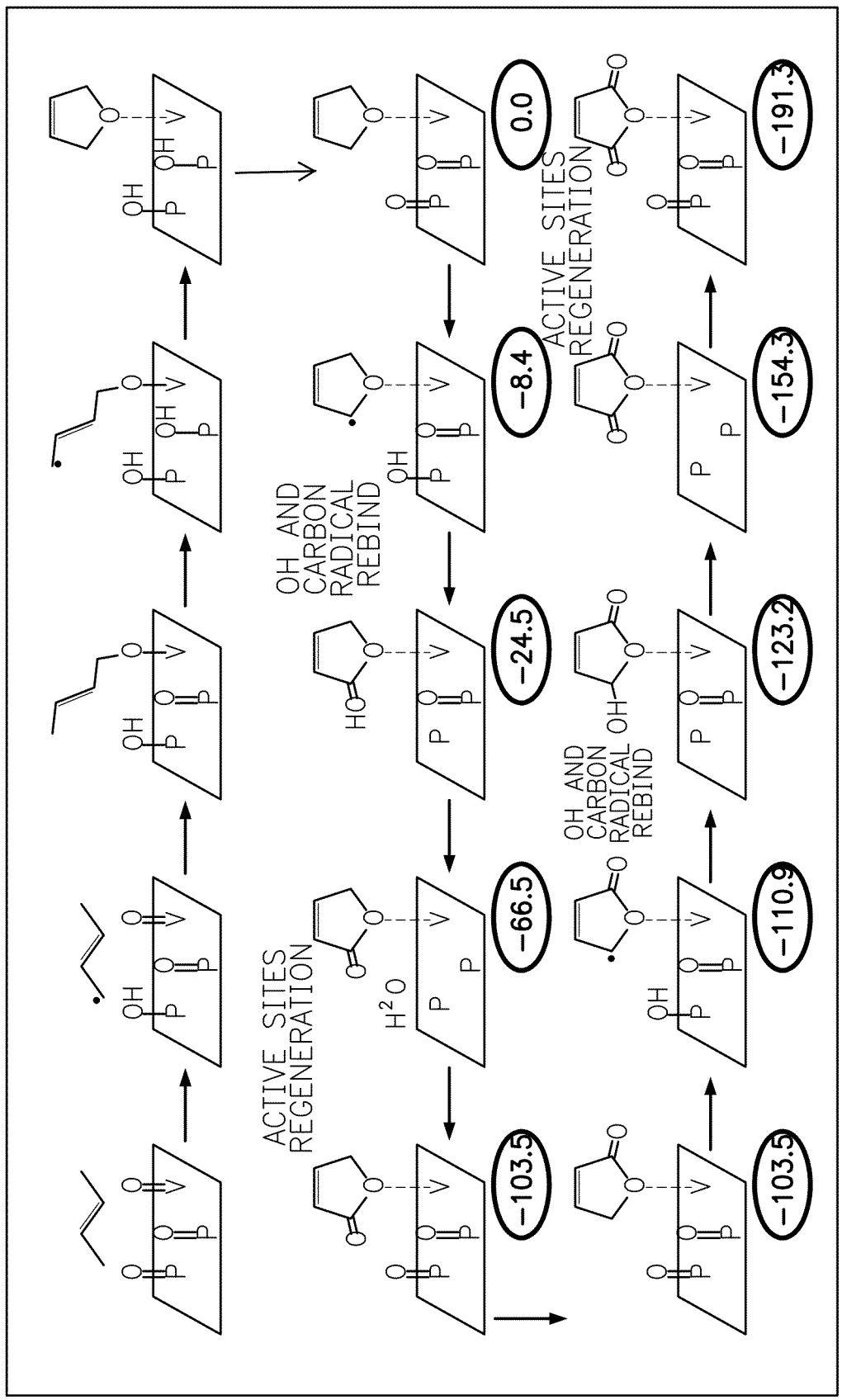
FIG. 42 – Continued $(VO)_2P_2O_7$ $(VO)_2P_2O_7$ (high symmetry)   X1-VOPO$_4$

METHODS FOR PROVIDING BOND ACTIVATION CATALYSTS AND RELATED CATALYSTS, SYSTEMS, AND METHODS

CROSS REFERENCE TO RELATED APPLICATIONS

The present application claims priority to U.S. Provisional Application No. 61/770,216 filed on Feb. 27, 2013 entitled "The Critical Role of Phosphate in Vanadium Phosphate Oxide for the Catalytic Activation and Functionalization of n-Butane to Maleic Anhydride", which is incorporated herein by reference in its entirety.

STATEMENT OF GOVERNMENT GRANT

This invention was made with government support under DE-PS02-05ER15944 awarded by the Department of Energy and under CHE1214158 awarded by the National Science Foundation. The government has certain rights in the invention.

FIELD

The present disclosure relates to methods for providing catalysts and in particular to methods for providing bond activation catalysts and related catalysts, in particular catalytic matrices, as well as related systems, and methods.

BACKGROUND

Improvements in performance of catalyzed reactions (e.g. conversion of n-butane to maleic anhydride (MA) catalyzed by vanadium phosphorus oxide (VPO)) would bring enormous economic and environmental benefits [Ref 1].

Despite numerous experimental [Ref 1-3] and a few theoretical [Ref 4-8] studies, the mechanism of catalyzed reactions such as catalytic oxidation reaction, remains under debate [Ref 3, 9-11].

Thus, development of improved catalysts and in particular improved C—H activation catalysts remains challenging.

SUMMARY

Described herein are methods for providing bond activation catalysts based on reduction-coupled activation and related catalysts, systems, and methods. In particular, bond activation catalysts herein described are capable in several embodiment of activating one or more substrates presenting a substrate-hydrogen bond which is homolytically cleaved by a catalytic site presented on the catalyst.

According to a first aspect, a method for providing a catalyst capable of activating a R—H bond of an R—H substrate, is described. In particular, in some embodiments the method comprises: selecting the R—H bond to be activated in an R—H substrate of formula (I):

R—H　　(I)

wherein R is an organic moiety selected from the group consisting of substituted or unsubstituted alkyl, alkenyl, alkynyl, aryl, alkoxy, aryloxy, alkylamino, arylamino, and acyl groups, the R—H bond having an R—H bond enthalpy; and selecting elements and/or functional groups Y1, X, M, A and optionally Y2 and/or Z, to form a set of selected elements and/or functional groups capable of forming a compound of formula (II):

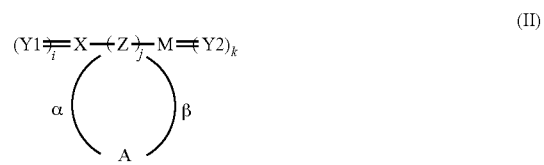

wherein:

Y1 is an element or functional group selected from the group consisting of O and NR', wherein R' is a hydrogen, substituted or unsubstituted alkyl, alkenyl, or aryl group, Y1 being capable of forming a Y1-H single bond with the group H from the R—H substrate, and the Y1-H single bond having a Y1-H enthalpy;

X is a column 15 or column 16 element capable of forming a double bond to Y1;

Y2 is an element or functional group selected from the group consisting of O and NR', wherein R' is a hydrogen, substituted or unsubstituted alkyl, alkenyl, or aryl group;

M is an element selected from the group consisting of V, Nb, Ta, Cr, Mo, W, Mn, Tc, Re, Fe, Ru, and Os;

A is a supporting moiety including a plurality of elements and/or functional groups linking M and X in a configuration presenting Y1 for reaction with a substrate; and Z is an element or functional group selected from the group consisting of O and NH;

α and β being independently one or more single covalent bonds;

i is 1-2;

j is 0-1; and k is 0-1.

In particular, in the method for providing a catalyst capable of activating a R—H bond of an R—H substrate, the selecting of a Y1, X, M, A, and optionally Y2 and/or Z, is performed to have a difference between the Y1-H bond enthalpy and the R—H bond enthalpy that is less than a threshold value in a model system. In some embodiments, the method further comprises mixing the set of selected elements and/or functional groups in a reaction mixture to synthesize a candidate catalyst comprising Y1, X, M, and A, and optionally Y2 and/or Z. In some embodiments, the method can also comprise contacting the synthesized candidate catalyst with the R—H substrate for a time and under conditions to allow the interaction between the Y1 element or functional group of the candidate catalysts with the R—H substrate. In some embodiments, the method can further comprise detecting activation of the R—H bond following the contacting to select the synthesized candidate catalyst capable of activating the R—H bond thus providing the catalyst capable of activating the R—H bond.

According to a second aspect, a catalyst for activation of a R—H bond in a R—H substrate of formula (I) is described, wherein the R—H bond has an R—H bond enthalpy. The catalyst is a compound of formula (II) wherein Y1, X, Z, M, and Y2 are selected such that the Y1-H bond enthalpy is equal or lower than the R—H bond enthalpy.

According to a third aspect, a catalytic matrix for activation of a R—H bond in a R—H substrate of formula (I), wherein the R—H bond has an R—H bond enthalpy, is described. The catalytic matrix comprises a plurality of catalytic cores of Formula (III)

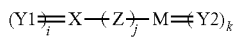

(III)

wherein in catalytic cores of the plurality of catalytic cores of formula (III), Y1, X, Z, M, and Y2 are selected in each catalytic core such that the Y1-H bond enthalpy is equal or lower than the R—H single bond enthalpy and wherein Y1, X, Z, M, and Y2 are independently selected among catalytic cores of the plurality of catalytic cores in the catalytic matrix. In the catalytic matrix, the M and X of each catalytic core of the plurality of the catalytic cores of Formula (III) are connected to a supporting moiety A including a plurality of elements and/or functional groups linking the M and the X of each catalytic core of the plurality of the catalytic cores of Formula (III), the supporting moiety A configured to form a framework presenting Y1 of each catalytic core of the plurality of the catalytic cores for reaction with a substrate R—H.

According to a fourth aspect, a method of selecting a catalyst for activation of a R—H bond in a R—H substrate of formula (I), the R—H bond having an R—H bond enthalpy, is described. The method comprises selecting a catalyst of formula (II) and/or a catalytic matrix comprising a plurality of catalytic cores of formula (III) having a Y1-H bond enthalpy equal or lower than the R—H single bond enthalpy.

According to a fifth aspect, a method of activating an R—H bond in an R—H substrate of Formula (I) is described. In particular, in some embodiments, the method comprises providing the R—H substrate comprising the R—H bond, the R—H bond having an R—H bond enthalpy; and providing a catalyst of formula (II) wherein Y1, X, Z, M, and Y2 are selected such that the Y1-H single bond enthalpy is equal or lower than the R—H single bond enthalpy. The method further comprises contacting the catalyst of Formula (II) and/or a catalytic matrix comprising a plurality of catalytic cores of formula (III) with the R—H substrate for a time and under conditions to allow the interaction between the Y1 element or functional group of the candidate catalysts with the R—H substrate; and detecting activation of the R—H bond following the contacting.

According to a sixth aspect, a system to activate an R—H bond in an R—H substrate is described. The system comprises one of more substrates R—H of Formula (I), the R—H bond having an R—H bond enthalpy; and one or more catalyst and/or catalytic matrices herein described wherein Y1, X, Z, M, and Y2 are selected such that the difference between the Y1-H bond enthalpy and the R—H bond enthalpy of the one or more substrates is equal or less than about 25 kcal/mol.

The methods, and related catalysts and in particular catalytic matrices, systems, and methods herein described allow in several embodiments to perform catalysis that is selective and active for substrates that are typically inactive when contacted with some known catalytic materials under certain known procedures. In particular, catalysts, and in particular catalytic matrices, systems, and methods herein described, allow in some embodiments to obtain bond activation catalysis on some substrates known to be inactive to bond activation.

In particular, catalysts, compositions, methods and systems herein described allow in several embodiments to minimize activating the products of the reaction or activating a different substrate also in the reaction mixture.

The catalysts, compositions, methods and systems herein described can be used in connection with applications wherein R—H activation is desired such as for example converting saturated hydrocarbons into functional materials useful for developing specialized and commodity chemicals. Exemplary applications comprise industrial chemistry applications, in particular when directed to synthesize feedstock chemicals such as maleic anhydride or acrylonitrile, pharmaceutical applications, in particular when directed to the functionalization of molecules to synthesize potential drug candidates, agricultural chemistry applications, in particular when directed to synthesize pesticides and herbicides as well as fertilizers, petrochemical application in particular when directed to synthesize and functionalize hydrocarbon-based fuels, and other applications that will be apparent to the skilled person upon a reading of the present disclosure.

The details of one or more embodiments of the disclosure are set forth in the accompanying drawings and the description below. Other features and objects will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 4A shows a schematic of the resting state of an ROA catalyst. FIG. 4B shows a schematic of an ROA catalyst after activation of substrate RH. FIG. 4C shows a schematic of the resting state of a non-ROA catalyst. FIG. 4D shows a schematic of a non-ROA catalyst after activation of substrate RH where N1 is a M1 atom that is not reduced.

FIG. 16A shows the ROA mechanism with a bridging atom Z1, bridging X and M. FIG. 16B shows ROA mechanism without a bridging atom.

FIG. 52A shows the olefinic route mechanism. FIG. 52B shows the alkoxide route mechanism.

DETAILED DESCRIPTION

Figure 1:
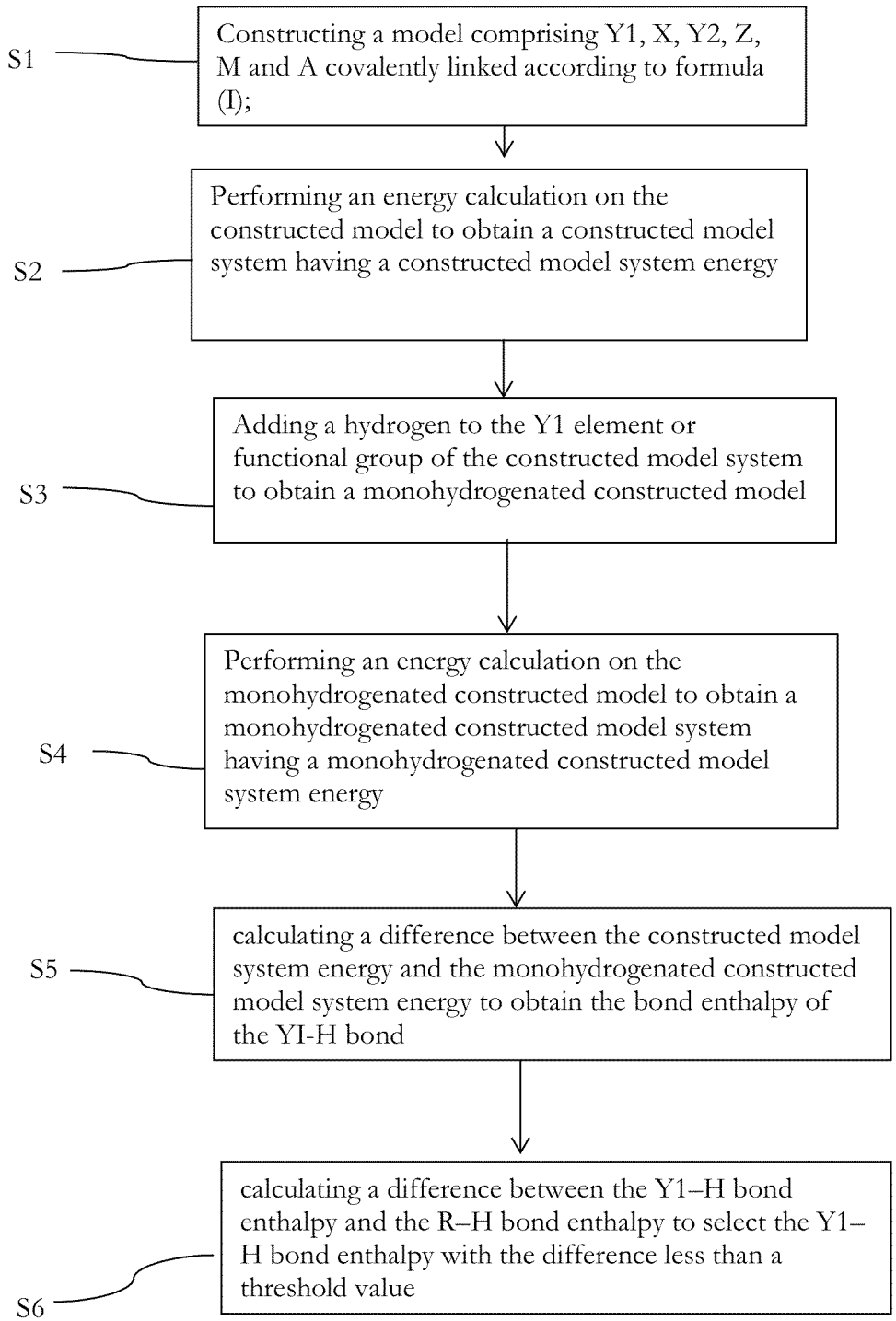
FIG. 1 shows a flowchart illustrating a method to perform selecting elements and/or functional groups Y1, X, M, A and optionally Y2 and/or Z, to form a set of selected elements and/or functional groups according to embodiments herein described

Described herein are methods for providing bond activation catalysts and related systems, and methods. In particular, several embodiments herein described are directed to catalysts presenting a catalytic site having a bond enthalpy when bond to hydrogen that is equal or lower than the bond enthalpy of the hydrogen in a substrate of interest.

The term "catalyst", as used herein, refers to a substance capable of increasing the rate and/or selectivity of a chemical reaction when added to the chemical reaction relative to the rate and/or selectivity of the reaction when the catalyst is not added. In particular, in some embodiments, the catalysts described herein are capable of catalyzing R—H bond activation reactions. A catalyst can participate in multiple chemical transformations. The effect of a catalyst can vary due to the presence of inhibitors (which reduce the catalytic activity) or promoters (which increase the activity). Catalyzed reactions have a lower activation energy (rate-limiting free energy of activation) than the corresponding uncatalyzed reaction, resulting in a higher reaction rate at the same temperature. Catalysts in the sense of the present disclosure comprise substance of various chemical nature such as elements or functional groups which can provide one or more catalytic site within a catalytic moiety or framework where the catalytic sites are presented for activation.

The term "catalytic site", as used herein refers to a particular atom directly involved in the bond-breaking and/or bond-forming steps of a catalyzed reaction occur. By way of example, the catalytic site of a catalyst which operates by abstracting a hydrogen from a substrate, is the particular atom which abstracts the hydrogen from the substrate.

The term "activation", as used herein, refers to a process in which a bond between two chemical species is broken such that one of the species can further react with additional chemical species or otherwise undergoing further chemical transformations. In particular, in some embodiments herein described, the activation is of an R—H bond in which the R—H bond is broken and the resulting R fragment can react with additional species. By way of example, a particular activation reaction can be C—H bond activation, for example, in the C—H activation of n-pentane to replace one of the hydrogen atoms with an iodine atom [Ref 12].

The term "bond enthalpy" as used herein refers to the energy required to homolytically break a chemical bond between two chemical species. By way of example, the bond enthalpy of a C—H bond in an ethane molecule is approximately 101 kcal/mol, meaning that approximately 101 kcal/mol of energy is required to homolytically break the C—H bond to form an ethyl radical and a hydrogen radical. Similarly, by way of another example, the bond enthalpy of a C—H bond in a benzene molecule is approximately 113 kcal/mol. Similarly, by way of another example, the bond enthalpy of the O—H bond in methanol is approximately 104 kcal/mol. Bond enthalpies can be determined computationally and/or experimentally, using methods known to a skilled person (see, e.g. [Ref 13]).

The term "presenting" as used herein, with reference to a element and/or functional group, and in particular with reference to a catalytic site, indicates attachment performed to maintain the chemical reactivity of the element, functional group, and/or catalytic site as attached. The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material. Accordingly, an element, functional group, and/or catalytic site presented on a moiety, is able to perform under the appropriate conditions the one or more chemical reactions that chemically characterize the functional group.

In embodiments wherein an element and/or functional groups are presented in a compound of Formula I or related portions therefore, the element and/or functional group are configured in the related structure so that under appropriate conditions they are able to perform the one or more chemical reactions that characterize the element and/or functional groups. For example, in a catalyst of Formula (I) comprising Y1, X, Z, M, and Y2 of O, Te, O, V, and κ, respectively, the catalyst can be configured with a particular moiety A (e.g. of Formula (IV)) such that the O, Te, O, V, and O are presented in such a way so as to permit the appropriate elements, functional groups, and/or catalytic sites (e.g. the O element for Y2) to be accessible to a particular substrate such that the substrate can interact with the appropriate elements, functional groups, and/or catalytic sites and undergo the reaction catalyzed by the catalyst.

In embodiments herein described the catalytic site Y1 is presented for binding with a target R—H bond in the substrate. Such language denotes a configuration of the remaining elements and/or functional groups of the catalytic core and/or supporting moiety A that results in a configuration of Y1, such that under appropriate condition Y1 is able to chemically react with an R—H substrate.

In some embodiments, the substrate of interest can be a R—H substrate of formula (I)

wherein R is an organic moiety selected from the group consisting of substituted or unsubstituted alkyl, alkenyl, alkynyl, aryl, alkoxy, aryloxy, alkylamino, arylamino and acyl groups, and wherein the R—H bond has a R—H bond enthalpy.

In some embodiments, R can be C1-C12 substituted or unsubstituted alkyl (e.g. methyl, ethyl, propyl, butyl, isobutyl, tert-butyl, pentyl, isopentyl, neopentyl, octyl, isooctyl, and others apparent to a skilled person), C2-C12 substituted or unsubstituted alkenyl and/or substituted or unsubstituted alkynyl (e.g. ethenyl, ethynyl, propenyl, propynyl, butenyl, butadienyl, and others apparent to a skilled person), C5-C10 substituted or unsubstituted aryl (e.g. pyrrolyl, oxazolyl, furanyl, pyridinyl, phenyl, naphthyl, indolyl, and others apparent to a skilled person), C1-C12 substituted or unsubstituted alkoxy (e.g. methoxy, ethoxy, propoxy, butoxy, sec-butoxy, tert-butoxy, pentoxy, and others apparent to a skilled person), C5-C10 substituted or unsubstituted aryloxy (e.g. pyrrolyl, oxazolyloxy, furanyloxy, pyridinyloxy, phenoxy, naphthyloxy, indolyloxy, and others apparent to a skilled person), C1-C12 substituted or unsubstituted alkylamino (e.g. methylamino, ethylamino, propylamino, butylamino, isobutylamino, tert-butylamino, pentylamino, isopentylamino, neopentylamino, octylamino, isooctylamino, and others apparent to a skilled person), C5-C10 substituted or unsubstituted arylamino (e.g. pyrrolylamino, oxazolylamino, furanylamino, pyridinylamino, anilino, naphthylamino, indolylamino, and others apparent to a skilled person) C1-C12 substituted or unsubstituted acyl (e.g. formyl, acetyl, propionyl, butanoyl, pentanoyl, hexamoyl, and others apparent to a skilled person).

In some embodiments, the method for providing a catalyst capable of activating a R—H bond of an R—H substrate comprises selecting the R—H bond to be activated in the R—H substrate. In some of these embodiments, the selecting of the R—H bond to be activated in the R—H substrate, is performed with an R—H substrate wherein R is an organic moiety selected from the group consisting of substituted or unsubstituted alkyl, alkenyl, alkynyl, aryl, alkoxy, aryloxy, alkylamino, arylamino, and acyl groups, the R—H bond having an R—H bond enthalpy.

In some embodiments, the R—H bond enthalpy of an R—H bond of a selected R—H substrate can be between about 95 and about 105 kcal/mol (e.g., an alkane C—H bond).

In some embodiments, the R—H bond enthalpy of an R—H bond of a selected R—H substrate can be between about 105 and about 110 kcal/mol (e.g., an alkene C—H bond).

In some embodiments, the R—H bond enthalpy of an R—H bond of a selected R—H substrate can be between about 110 and about 115 kcal/mol (e.g., an arene C—H bond).

In some embodiments, the R—H bond enthalpy of an R—H bond of a selected R—H substrate can be between about 125 and about 135 kcal/mol (e.g., an alkyne C—H bond).

In some embodiments, the R—H bond enthalpy of an R—H bond of a selected R—H substrate can be between about 85 and about 97 kcal/mol (e.g. an aldehyde C—H bond or a terminal C—H in propene).

In some embodiments, the method to provide a catalysts further comprises selecting elements and/or functional groups Y1, X, M, A and optionally Y2 and/or Z.

The term "element", as used herein, refers to a chemical element as shown in the periodic table of the elements. In particular, a skilled person will realize that each column of elements in the periodic table is designated as a "group" or "column". For example, the column of elements beginning with vanadium is designated column 5, the column of elements beginning with nitrogen is column 15, and the column of elements beginning with oxygen is column 16. Thus, a phrase such as "a column 15 element" or "an element selected from column 15" refers to an element of column 15 of the periodic table.

The term "functional group", as used herein, refers to a group of atoms of chemical elements bonded together to form a group of atoms which are capable of forming bonds with one or more additional elements or functional groups. The bonds formed can be single or multiple (e.g. double or triple bonds). In particular, some exemplary functional groups can be, for example, =O, =Se, =NH, =Ph, =CH2, —NH—, —PH—, and/or —CH2-, where the "=" denotes a double bond to another element or functional group, and "—" denotes a single bond to another element or functional group.

In some of these embodiments, the selecting of elements and/or functional groups Y1, X, M, A and optionally Y2 and/or Z, is performed to form a set of selected elements and/or functional groups capable of forming a compound of formula (II):

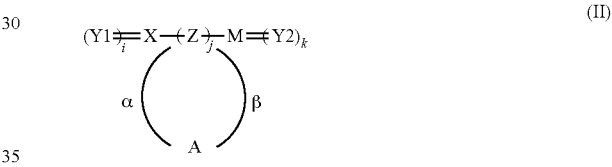

wherein:
  Y1 is an element or functional group selected from the group consisting of O and NR', wherein R' is a hydrogen, substituted or unsubstituted alkyl, alkenyl, or aryl group, Y1 being capable of forming a Y1-H single bond with the group H from the R—H substrate, and the Y1-H single bond having a Y1-H enthalpy;
  X is a column 15 or a column 16 element capable of forming a double bond to Y1;
  Y2 is an element or functional group selected from the group consisting of O and NR', wherein R' is a hydrogen, substituted or unsubstituted alkyl, alkenyl, or aryl group;
  M is an element selected from the group consisting of V, Nb, Ta, Cr, Mo, W, Mn, Tc, Re, Fe, Ru, and Os;
  A is a supporting moiety including a plurality of elements and/or functional groups linking M and X in a configuration presenting Y1 for reaction with a substrate; and
  Z is an element or functional group selected from the group consisting of O and NH;
  α and β being independently one or more single covalent bonds;
  i is 1-2;
  j is 0-1; and
  k is 0-1;

In some embodiments, Y1 can be a functional group NR' such as, for example, NH, NCH$_3$, NCH=CH$_2$, NPh (where Ph indicates phenyl), and others identifiable to the skilled person upon a reading of the present disclosure. A related Y1-H bond enthalpy is determined as function of the chemical nature of the elements linked to the catalytic site Y1 (see e.g. Example 16).

In some embodiments, X can be an element selected from the group consisting of P, As, Sb, Bi, S, Se, Te, and Po. In some embodiments, element X can be bound to other elements and/or functional group as will be understood by a skilled person. For example, in some embodiments X can be bound to one or more group such as OH (e.g. X can be Te—OH) or other groups which can be selected in view of their ability to affect the Y1-H bond enthalpy (e.g. through computational analysis).

In some embodiments, Y2 can be a functional group NR' such as, for example, NH, $NCH_3$, $NCH=CH_2$, NPh (where Ph indicates phenyl), and others identifiable by a skilled person upon a reading of the present disclosure.

In some embodiments, M can be a transition metal having valence electron populations $d^0$ and $d^1$ in the higher and lower oxidation states, respectively, of M.

In some embodiments, M can be an element selected from the group consisting of $V^{+5}$ $V^{+4}$, $Cr^{+6}$, $Mo^{+6}$, $Mo^{+5}$, $Mn^{+7}$, $Mn^{+5}$, and $Mn^{+4}$.

In some embodiments, A can comprise various combinations of O, NH—, P, As, Sb, Bi, S, Se, Te, Po and various metals such as V, Nb, Ta, Cr, Mo, W, Mn, Tc, Re, Fe, Ru, and Os linked together with element M and X with one or more covalent bonds in accordance with the structure of Formula (II). A skilled person will understand, upon a reading of the present disclosure, that the moiety A can comprise additional atoms and/or functional groups which can be linked one to the other and to M and X of Formula (II) in various amounts and proportions to form a bulk of the catalyst of formula (II) configured to link M and X and to present Y1 for reaction with a substrate. A skilled person based on the information concerning Y, X and M will be able to identify and provide a corresponding moiety A formed by various combinations of related elements, even in absence of detailed indications concerning the exact number of atoms and/or functional groups or the absolute structure of the bulk catalyst applying techniques and procedures identifiable by a skilled person upon reading of the present disclosure. [Ref 14, 15].

In embodiments herein described, the selecting of a Y1, X, M, A, and optionally Y2 and/or Z, is performed in function of a set Y1-H bond enthalpy. In particular, in some embodiments, the selecting of a Y1, X, M, A, and optionally Y2 and/or Z, is performed to provide a Y1-H bond enthalpy differing from the R—H bond enthalpy for a value which is less than a threshold value in a model system.

The term "threshold value", as used herein, refers to a particular amount of energy that is set as the difference between a particular Y1-H bond enthalpy and a corresponding particular R—H bond enthalpy. The particular threshold, or difference in energy between a particular Y1-H bond enthalpy and a corresponding particular R—H bond enthalpy determined according to methods herein described, can correlate to the activation energy of a particular C—H activation reaction. In particular, in some embodiments the activation energy is be less than 23 kcal/mol greater than a particular difference in energy between a particular Y1-H bond enthalpy and a corresponding particular R—H bond enthalpy determined according to methods herein described.

The term "model system", as used herein, refers to a hypothetical chemical structure that is representative of a larger chemical structure such as that of a catalyst, and in particular, such as that of catalysts synthesized by the methods herein described. In particular, in some embodiments herein described, the chemical structure comprising a model system can be constructed in a computer using molecular modelling software known to a skilled person (e.g. Gaussian, Spartan, Jaguar, and others known to a skilled person).

In particular, in some embodiments, a threshold value can be between about 10 and about 25 kcal/mol. In particular, in some embodiments, the threshold value can be between about 10 and about 15 kcal/mol, between about 15 and about 20 kcal/mol, or between about 20 and about 25 kcal/mol.

In particular, in some embodiments, selecting elements and/or functional groups Y1, X, M, A and optionally Y2 and/or Z, can be performed to obtain a Y1-H bond enthalpy as schematically illustrated in FIG. 1 by: (S1) constructing a model comprising X, Y1, Z, M and A covalently linked according to Formula (II); (S2) performing energy calculation on the constructed model system to obtain a constructed model system having a constructed model system energy; (S3) adding a hydrogen to the Y1 element or functional group of the constructed model system to obtain a monohydrogenated constructed model; (S3) performing an energy calculation on the monohydrogenated constructed model to obtain a monohydrogenated constructed model system having a monohydrogenated constructed model system; and (S5) calculating a difference between the constructed model system energy and the monohydrogenated constructed model system energy to obtain the bond enthalpy of the Y1-H bond. In some of those embodiments the selecting can also include (S6) calculating a difference between the Y1-H bond enthalpy and the R—H bond enthalpy to select the Y1-H bond enthalpy with the difference less than the threshold value.

A skilled person will understand that the calculations of each of steps (S1) to (S6) can be performed, and models constructed, using software packages available to a skilled person. In particular, the aforementioned calculations can be performed, and models constructed, using software packages available to a skilled person (e.g. Gaussian, Spartan, Jaguar, and others known to a skilled person) and using the calculation methods as herein described (see e.g. Example 16).

In particular, in some embodiments, the constructing of a model is performed by: selecting X, Y1, Z and M; selecting A to link X, Y1, Z and M according to formula (II); and constructing the model by providing an initial geometry to the selected X, Y1, Z, M, and A according to formula (II).

In particular, in some embodiments, A can comprise a reducible metal. In some embodiments, the reducible metal can be a metal selected from the group consisting of $V^{+5}$ $V^{+4}$, $Cr^{+6}$, $Mo^{+6}$, $Mo^{+5}$, $Mn^{+7}$, $Mn^{+5}$, and $Mn^{+4}$.

In particular, in some embodiments, A can be a moiety of formula (IV):

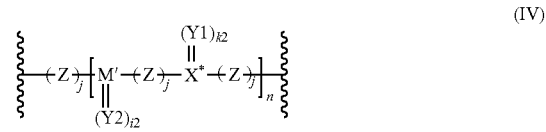

(IV)

wherein:

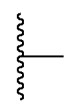

is an α and/or β bond;

X* is a column 15 or 16 element capable of forming a double bond to Y1 or an element selected from the group consisting of V, Nb, Ta, Cr, Mo, W, Mn, Tc, Re, Fe, Ru, and Os, X* being optionally substituted with a moiety of formula (V):

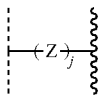

or formula (VI):

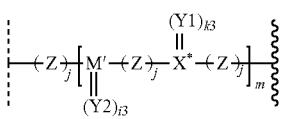

wherein

is the bond to X*;

M' is selected from the group consisting of V, Nb, Ta, Cr, Mo, W, Mn, Tc, Re, Fe, Ru, and Os independent of M;

and wherein m is 1-6 and n is 1-6, and i2, i3, k2, and k3 are independently 0 or 1.

In particular, in some embodiments, A is a moiety of formula (VII):

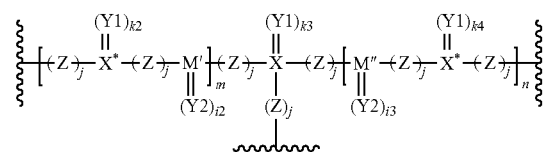

wherein:

is an α and/or β bond;

X* is a column 15 or 16 element capable of forming a double bond to Y1 or an element selected from the group consisting of V, Nb, Ta, Cr, Mo, W, Mn, Tc, Re, Fe, Ru, and Os, X* being optionally substituted with a moiety of formula (V):

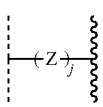

or formula (VI):

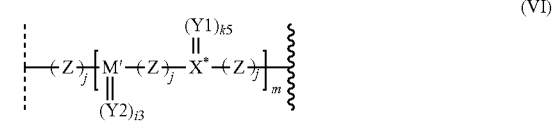

wherein

is the bond to X*;

M' and M" are independently selected from the group consisting of V, Nb, Ta, Cr, Mo, W, Mn, Tc, Re, Fe, Ru, and Os independent of M;

and wherein m is 1-6 and n is 1-6, and i2, i3, i4, k2, k3, k4, and k5 are independently 0 or 1.

In particular, in some embodiments, A is a moiety of formula (VIII):

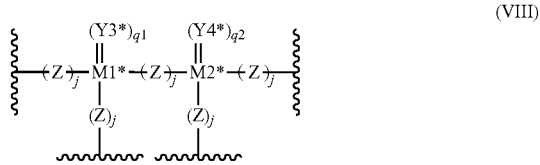

wherein:

is an α and/or β bond;

M1* and M2* are independently column 15 or 16 elements capable of forming a double bond to Y1, or elements selected from the group consisting of V, Nb, Ta, Cr, Mo, W, Mn, Tc, Re, Fe, Ru, and Os independent of M;

Y3* is either:
  Y2 when M1 is an element selected from the group consisting of V, Nb, Ta, Cr, Mo, W, Mn, Tc, Re, Fe, Ru, and Os;
  or
  Y1 when M1 is a column 15 or 16 element capable of forming a double bond to Y1;

and Y4* is either:
  Y2 when M1 is an element selected from the group consisting of V, Nb, Ta, Cr, Mo, W, Mn, Tc, Re, Fe, Ru, and Os;
  or
  Y1 when M1 is a column 15 or 16 element capable of forming a double bond to Y1; and q1 and q2 are independently 0 or 1.

In particular, in some embodiments, A is a moiety of formula (X):

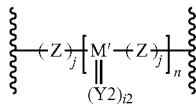

wherein:

is an α and/or β bond;
M' is selected from the group consisting of V, Nb, Ta, Cr, Mo, W, Mn, Tc, Re, Fe, Ru, and Os independent of M;
i2 is 0 or 1;
and n is 1-6.

In particular, in some embodiments, particular combinations of Y1, X, Z, M, and Y2 can be selected with particular moieties of A by first selecting an M and then an X. The following exemplary combinations can be made, as shown in Table 1.

TABLE 1

| M | X | M', M'', M1*, M2* | Z | Y1, Y2, Y3*, Y4* |
|---|---|---|---|---|
| Column 5 element | Column 15 element | Column 5 element | O or NH | O or NR' |
| Column 5 element | Column 15 element | Column 7 element | O or NH | O or NR' |
| Column 5 element | Column 15 element | Column 15 element | O or NH | O or NR' |
| Column 7 element | Column 15 element | Column 5 element | O or NH | O or NR' |
| Column 7 element | Column 15 element | Column 7 element | O or NH | O or NR' |
| Column 7 element | Column 15 element | Column 15 element | O or NH | O or NR' |
| Column 5 element | Column 16 element | Column 5 element | O or NH | O or NR' |
| Column 5 element | Column 16 element | Column 7 element | O or NH | O or NR' |
| Column 5 element | Column 16 element | Column 15 element | O or NH | O or NR' |
| Column 7 element | Column 16 element | Column 5 element | O or NH | O or NR' |
| Column 7 element | Column 16 element | Column 7 element | O or NH | O or NR' |
| Column 7 element | Column 16 element | Column 15 element | O or NH | O or NR' |

Figure 2:
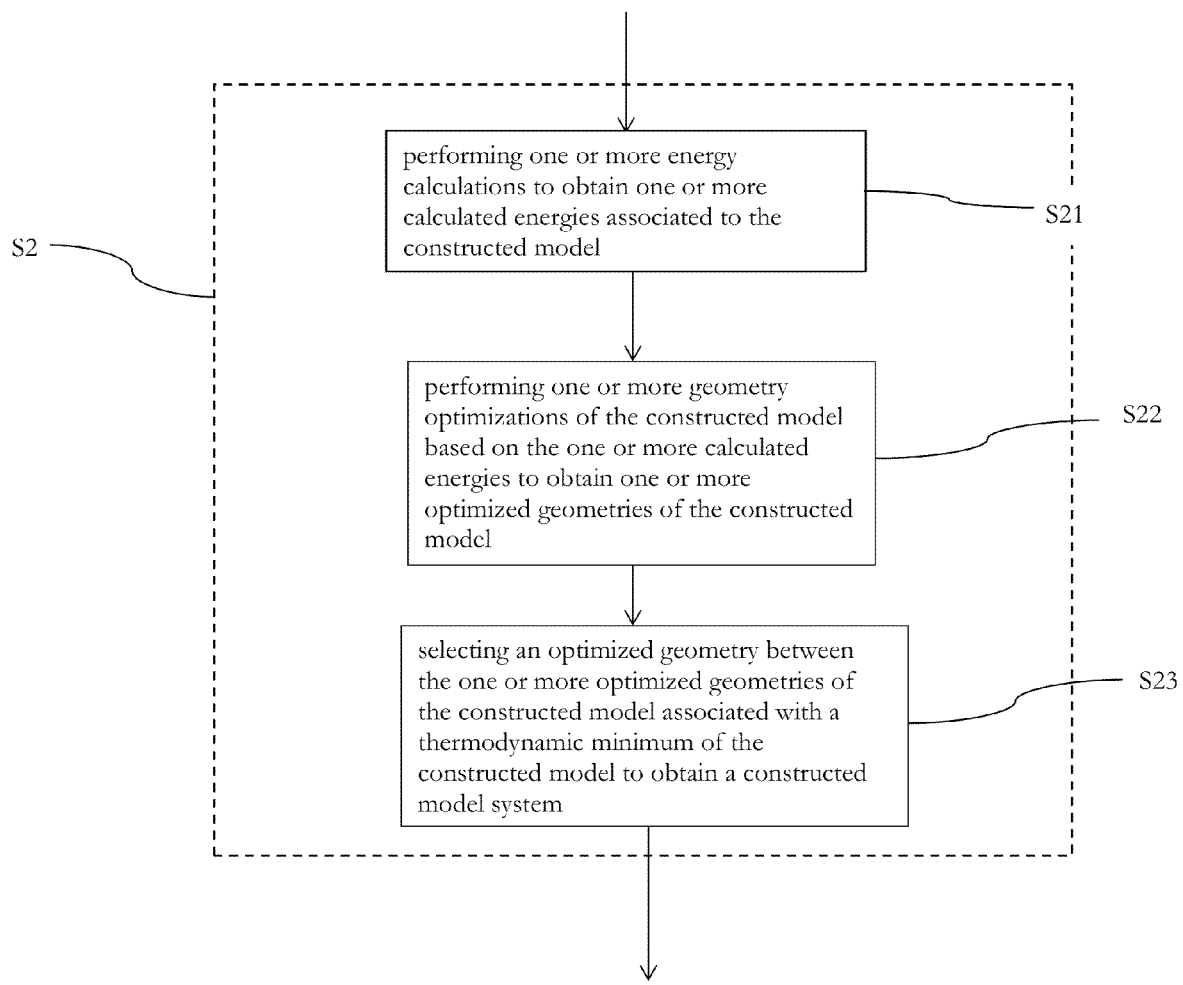
FIG. 2 shows a flowchart illustrating a method for performing an energy calculation on the constructed model to obtain a constructed model system having a constructed model system energy according to embodiments herein described

The constructed model so obtained (FIG. 2 (S1)) the can then be subjected to energy calculations to provide a constructed model system having a constructed model system energy. (FIG. 1 (S2))

In some embodiments, performing an energy calculation on the constructed model to obtain a constructed model system (FIG. 1 (S2)) can be performed by selecting the model system having a geometry associated to a thermodynamic minimum. In particular, in some of those embodiments, the performing an energy calculation on the constructed model, can be performed as schematically illustrated in FIG. 2 by: performing one or more energy calculations to obtain one or more calculated energies associated to the constructed model (S21); performing one or more geometry optimizations of the constructed model based on the one or more calculated energies to obtain one or more optimized geometries of the constructed model (S22); selecting an optimized geometry between the one or more optimized geometries of the constructed model associated with a thermodynamic minim of the constructed model to obtain a constructed model system (S23). In particular, the aforementioned calculations can be performed, and geometries optimized, using software packages available to a skilled person (e.g. Gaussian, Spartan, Jaguar, and others known to a skilled person) and using the calculation methods as herein described (see e.g. Example 16).

The constructed model system so obtained (FIG. 2(S2)) can be converted into a monohodrogenated model by adding a hydrogen to the Y1 element of functional group (FIG. 1(S3)) and the monohydrogenated model so obtained can then be subjected to energy calculations to provide a monohydrogenated constructed model system having a constructed model system energy. (FIG. 1(S4))

Figure 3:
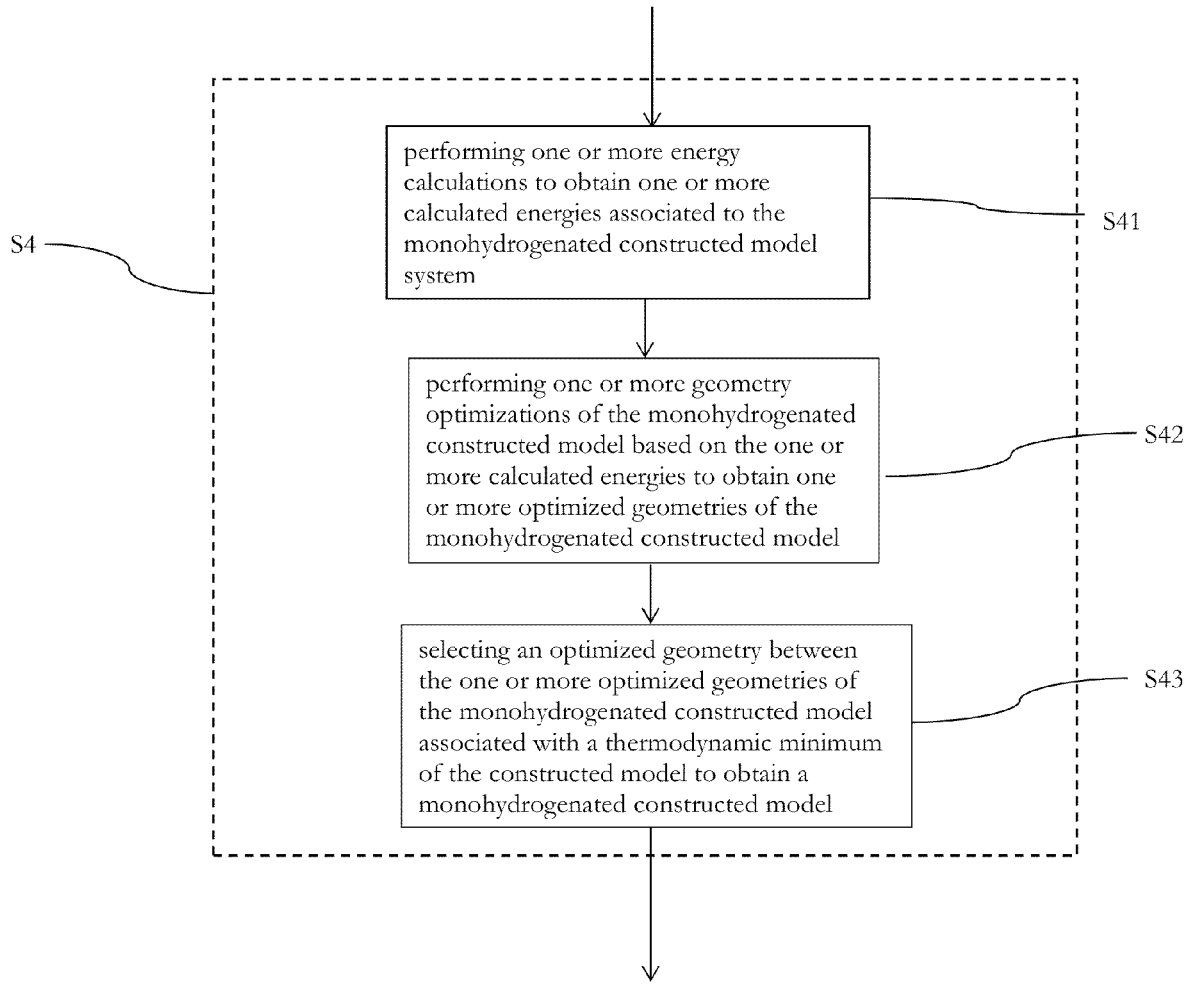
FIG. 3 shows a flowchart illustrating a method for performing an energy calculation on a monohydrogenated constructed model to obtain a monohydrogenated constructed model system having a monohydrogenated constructed model system energy according to embodiments herein described.

In some embodiments, performing an energy calculation on the monohydrogenated constructed model to obtain a constructed model system (FIG. 1, (S4)) can be performed by selecting the monohydrogenated model system having a geometry associated to a thermodynamic minimum. In particular, in some of those embodiments, the performing an energy calculation on the monohydrogenated constructed model, can be performed as schematically illustrated in FIG. 3 by: performing one or more energy calculations to obtain one or more calculated energies associated to the monohydrogenated constructed model (S41); performing one or more geometry optimizations of the monohydrogenated constructed model based on the one or more calculated energies to obtain one or more optimized geometries of the constructed model (S42); selecting an optimized geometry between the one or more optimized geometries of the monohydrogenated constructed model associated with a thermodynamic minim of the constructed model to obtain a monohydrogenated constructed model system (S43). In particular, the aforementioned calculations can be performed, and geometries optimized, using software packages available to a skilled person (e.g. Gaussian, Spartan, Jaguar, and others known to a skilled person) and using the calculation methods as herein described (see e.g. Example 16).

In some embodiments, the obtained constructed model system energy (FIG. 1 (S2) and the monohydrogenated constructed model system energy (FIG. 1 (S4) can be subjected to calculation to obtain the Y1-H bond enthalpy. In particular the bond Y1-H enthalpy can be provided by calculating a difference between the constructed model system energy and the monohydrogenated constructed model system energy to obtain the bond enthalpy of the YI—H bond (FIG. 1 (S5)). In some embodiments, the Y1-H bond enthalpy can be further selected with reference to a threshold value calculated in function of the R—H bond enthalpy. In some of those embodiments, the selecting can further comprises, calculating a difference between the Y1-H bond enthalpy and the R—H bond enthalpy to select the Y1-H bond enthalpy with the difference less than the threshold value and in particular of a threshold value of a model system (FIG. 1(S6).

In particular, the model system used in the selecting of the Y1 X, M, and A elements and optionally Y2 and/or Z elements and/or functional groups according to embodiments herein described that results in the difference between the Y1-H bond enthalpy and the R—H bond enthalpy that is less than a threshold value can be the model system according to Formula (X):

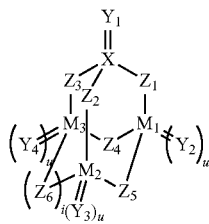

(X)

wherein:
- Y1 is an element or functional group selected from the group consisting of O and NR', wherein R' is a hydrogen, substituted or unsubstituted alkyl, alkenyl, or aryl group, Y1 being capable of forming a Y1-H single bond with the group H from the R—H substrate, and the Y1-H single bond having a Y1-H enthalpy;
- X is a column 15 capable of forming a double bond to Y1 (e.g. below N in column 15);
- M1 is an element selected from the group consisting of V, Nb, Ta, Cr, Mo, W, Mn, Tc, Re, Fe, Ru, and Os;
- M2-M3 are column 15 or 16 elements capable of forming a double bond to Y3-Y4 or elements selected from the group consisting of V, Nb, Ta, Cr, Mo, W, Mn, Tc, Re, Fe, Ru, and Os;
- Y2-Y4 are elements or functional groups selected from the group consisting of O and NR', wherein R' is a hydrogen, substituted or unsubstituted alkyl, alkenyl, or aryl group;
- Z is an element or functional group selected from the group consisting of O and NH;
- Z2-Z6 are elements or functional group selected from the group consisting of O and NH;
- Z2-Z6, M2-M3 and Y3-Y4 are the plurality of elements and/or functional groups linked to M and X in a configuration presenting Y1 for reaction with a substrate thus forming the moiety A;
- u is 0-2;
- i is 0-1, wherein:
  - when i is 0, there is no Z6 and no direct bond exists between M2 and M3.

In particular, in some embodiments, when M2-M3 are group 5, 7, or 15 elements, i=u=1.

In particular, in some embodiments, when M2-M3 are group 6 or group 8 elements, i=0 and u=2.

In some embodiments, particular combinations of Y1-Y4, X, Z1-Z6, and M1 in formula (IV) can be selected by first selecting an M1 and then an X. The following exemplary combinations can be made, as shown in Table 2.

In some embodiments, the model system used in the selecting of the Y1 X, M, and A elements and optionally Y2 and/or Z elements and/or functional groups that results in the difference between the Y1-H bond enthalpy and the R—H bond enthalpy that is less than a threshold value in the model system according to Formula (XI):

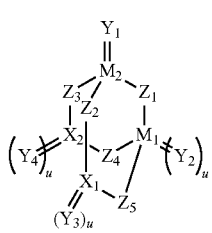

(XI)

wherein:
- Y1 is an element or functional group selected from the group consisting of O and NR', wherein R' is a hydrogen, substituted or unsubstituted alkyl, alkenyl, or aryl group, Y1 being capable of forming a Y1-H single bond with the group H from the R—H substrate, and the Y1-H single bond having a Y1-H enthalpy;
- X is a column 15 or 16 element capable of forming a double bond to Y1;
- X1 and X2 are column 15 and 16 elements capable of forming a double bond to Y1.
- M is an element selected from the group consisting of V, Nb, Ta, Cr, Mo, W, Mn, Tc, Re, Fe, Ru, and Os;
- M2-M3 are elements selected from the group consisting of V, Nb, Ta, Cr, Mo, W, Mn, Tc, Re, Fe, Ru, and Os;
- Y2-Y4 are elements or functional groups selected from the group consisting of O and NR', wherein R' is a hydrogen, substituted or unsubstituted alkyl, alkenyl, or aryl group;
- Z is an element or functional group selected from the group consisting of O and NH;
- Z2-Z5 are elements or functional group selected from the group consisting of O and NH;
- Z2-Z5, M2-M3 and Y3-Y4 are the plurality of elements and/or functional groups linked to M and X in a configuration presenting Y1 for reaction with a substrate thus forming the moiety A; and
- u is 0-2.

In some embodiments, particular combinations of Y1-Y4, X, Z1-Z6, and M1 can be selected by first selecting an M1 and then an X1 and X2. By way of example, the following exemplary combinations can be made, as shown in Table 3.

TABLE 2

| M1 | X | M2, M3 | Z | Y1, Y2 | u |
|---|---|---|---|---|---|
| Column 5 element | Column 15 element | Column 5, 7, or 5 element | O or NH | O or NR' | 1 |
| Column 7 element | Column 15 element | Column 5, 7, or 5 element | O or NH | O or NR' | 1 |

TABLE 3

| M1 | X1, X2 | M2, M3 | Z | Y1, Y2 | u |
|---|---|---|---|---|---|
| Column 5 element | Column 15 element | Column 6 or 8 element | O or NH | O or NR' | 2 |
| Column 7 element | Column 15 element | Column 6 or 8 element | O or NH | O or NR' | 2 |
| Column 5 element | Column 16 element | Column 6 or 8 element | O or NH | O or NR' | 2 |
| Column 7 element | Column 16 element | Column 6 or 8 element | O or NH | O or NR' | 2 |

In particular, in some embodiments, the model system used in the selecting the Y1 X, M, and A elements and optionally Y2 and/or Z elements and/or functional groups that results in the difference between the Y1-H bond enthalpy and the R—H bond enthalpy that is less than a threshold value in the model system according to Formula (XII):

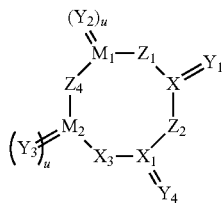

(XII)

wherein:

Y1 is an element or functional group selected from the group consisting of O and NR', wherein R' is a hydrogen, substituted or unsubstituted alkyl, alkenyl, or aryl group, Y1 being capable of forming a Y1-H single bond with the group H from the R—H substrate, and the Y1-H single bond having a Y1-H enthalpy;

X and X1 are column 15 or 16 elements capable of forming a double bond to Y1;

M is an element selected from the group consisting of V, Nb, Ta, Cr, Mo, W, Mn, Tc, Re, Fe, Ru, and Os;

M1-M2 are column 15 or 16 elements capable of forming a double bond to Y3-Y4 or elements selected from the group consisting of V, Nb, Ta, Cr, Mo, W, Mn, Tc, Re, Fe, Ru, and Os;

Y2-Y4 are elements or functional groups selected from the group consisting of O and NR', wherein R' is a hydrogen, substituted or unsubstituted alkyl, alkenyl, or aryl group;

Z is an element or functional group selected from the group consisting of O and NH;

Z2-Z4 are elements or functional group selected from the group consisting of O and NH;

Z2-Z4, M2-M3 and Y3-Y4 are the plurality of elements and/or functional groups linked to M and X in a configuration presenting Y1 for reaction with a substrate thus forming the moiety A; and u is 1-2.

In some embodiments, the model system used in the selecting of the Y1 X, M, and A elements and optionally Y2 and/or Z elements and/or functional groups that results in the difference between the Y1-H bond enthalpy and the R—H bond enthalpy that is less than a threshold value can be the model system according to Formula (XIV):

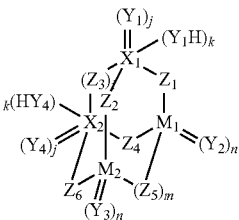

(XIV)

wherein:

Y1 and Y4 are elements or functional groups selected from the group consisting of O and NR', wherein R' is a hydrogen, substituted or unsubstituted alkyl, alkenyl, or aryl group, Y1 and Y4 being capable of forming a Y1-H or Y4-H single bond with the group H from the R—H substrate, and the Y1-H or Y4-H single bond having a Y1-H or Y4-H enthalpy;

X1 and X2 a column 16 element (e.g. S, Se, Te) heavier than N capable of forming a double bond to Y1;

M1-M2 are column 5 or 7 elements heavier than N capable of forming a double bond to Y2-Y3 or column 6 or 8 elements, wherein, in some embodiments, when M1-M2 are column 5 or 7 elements, m=n=1 and, in some embodiments when M1-M2 are column 6 or 8 elements, m=0 and n=2;

Y2-Y3 are elements or functional groups selected from the group consisting of O and NR', wherein R' is a hydrogen, substituted or unsubstituted alkyl, alkenyl, or aryl group;

Z1 is an element or functional group selected from the group consisting of O and NH;

Z2-Z6 are elements or functional group selected from the group consisting of O and NH;

Z2-Z6, M2, X2 and Y3-Y4 are the plurality of elements and/or functional groups linked to M and X in a configuration presenting Y1 for reaction with a substrate thus forming the moiety A;

i is 0-1 m is 0-1;

j is 0-1;

k is 1-3; and wherein:

when i is 0, there is no Z3 and no direct bond exists between X1 and X2, and/or when m is 0, there is no Z3 and no direct bond exists between M1 and M2.

In embodiments wherein an investigation of X in the +4 oxidation state is desired, there are two choices: the dehydrated form (see e.g. Example 8), with i=0, j=1, k=0; or the hydrated form (see e.g. Example 9), with i=1, j=0, and k=3.

In embodiments wherein an investigation of X in the +6 oxidation state is desired, there are two choices: the dehydrated form (see e.g. Example 6), with i=0 and j=2; or the hydrated form (see e.g. Example 7), with i=j=1 and k=1.

In some embodiments, selecting an R—H substrate and selecting elements and/or functional groups Y1, X, M, A and optionally Y2 and/or Z to obtain a set of selected elements and/or functional groups are followed mixing the set of selected elements and/or functional groups in a reaction mixture to synthesize a candidate catalyst comprising Y1, X, M, and A, and optionally Y2 and/or Z.

In some embodiments of the methods herein described, the mixing of the set of selected elements and/or functional groups in a reaction mixture is performed to synthesize a candidate catalyst comprising Y1, X, M, and A, and optionally Y2 and/or Z. A skilled person will be able to identify techniques and procedures that are identifiable by a skilled person upon reading of the present disclosure.

In particular, in some embodiments, the mixing of the set of selected elements and/or functional groups in a reaction mixture to synthesize a candidate catalyst comprising Y1, X, M, and A, and optionally Y2 and/or Z can be performed by methods known to the skilled person (see e.g. [Ref 16, 17] and Examples 1 and 2). By way of example, a particular M can be introduced by the mixing of an oxide of the element M (e.g. $V_2O_5$ or $CrO_3$). A particular X can be introduced by the mixing of an appropriate oxyanion form of the X (e.g. sulfate for S, phosphate for P, or tellurate for Te), and it will also be apparent to a skilled person that when an X is also to be bound to an OH group, that such an OH group can be introduced by hydration with H2O according to methods known to a skilled person. A particular Z will often be introduced as part of the compound used to introduce the M and/or X (e.g. O from CrO3 or tellurate), but can also be introduced though chemical treatments identifiable by a skilled person (e.g. treatment with $O_2$ or $H_2O$). Similarly, a particular Y1 can be introduced as part as part of the compound used to introduce the M and/or X (e.g. O from CrO3 or tellurate), but can also be introduced but can also be introduced though chemical treatments known to a skilled person (e.g. treatment with $O_2$ or $H_2O$). A skilled person will also be able to identify that the particular conditions (e.g. concentration, temperature, and/or pressure) under which the mixing is performed can control the configuration of the synthesized catalyst produced to provide particular A moieties.

In some embodiments, the method further comprises contacting the synthesized candidate catalyst with the R—H substrate for a time and under conditions to allow the interaction between the Y1 element or functional group of the candidate catalysts with the R—H substrate. In particular, a skilled person will realize that the contacting can be performed in an industrial apparatus configured for gas phase reactions, but can also be performed under laboratory conditions using solution phase chemistry with homogeneous and heterogeneous forms of the catalysts and catalytic matrices herein described.

In some embodiments, the method further comprises detecting activation of the R—H bond following the contacting to select the synthesized candidate catalyst capable of activating the R—H bond thus obtaining the catalyst capable of activating the R—H bond In some embodiments of the methods herein described, the detecting activation of the R—H bond following the contacting to select the synthesized candidate catalyst capable of activating the R—H bond thus obtaining the catalyst capable of activating the R—H bond. A skilled person will realize that the activation can be detected by analytical methods such as, for example, gas chromatography-mass spectrometry (gs-ms), infrared spectroscopy (IR), Raman spectroscopy, nuclear magnetic resonance spectroscopy, and others know to a skilled person, such that the activation can be detected by determining the presence of products expected from the activation reaction for a particular substrate.

In some embodiments, the present disclosure also comprises catalysts for activation of a R—H bond in a R—H substrate wherein R is an organic moiety selected from the group consisting of substituted or unsubstituted alkyl, alkenyl, alkynyl, aryl, alkoxy, aryloxy, alkylamino, arylamino, and acyl groups, the R—H bond having an R—H bond enthalpy which can be selected by the method for providing an activation catalyst herein described.

In particular, in some embodiments, the catalysts can be of formula (II): wherein Y1, X, Z, M, and Y2 are selected such that the Y1-H single bond enthalpy is equal or lower than the R—H single bond enthalpy. A skilled person based on the information concerning Y, X and M will be able to identify and provide a moiety A, even in absence of detailed indications concerning the exact number of atoms and/or functional groups or the absolute structure of the bulk catalyst.

More particularly, a skilled person will understand that a structure of the, portions of a catalyst of Formula (II) which does not comprise the core catalyst formed by Y1, X, M and optionally Z and Y2, can include various combinations of elements and/or functional groups and can vary depending on the preparation conditions. In those embodiments, knowledge of exact amounts and proportion of the plurality of atoms that comprise that portion of the catalyst A connected to the X-=Y1 and M(Y2)k groups is not required and a structure A can be prepared such that X-=Y1 and M(Y2)k groups are presented on the surface and thus presented for reaction with a substrate using techniques and procedure identifiable by a skilled person (e.g. [Ref 14, 15]) Accordingly, various, catalysts can be designed and synthesized by methods described herein which have a plurality of internal atoms and/or functional groups forming a moiety A which would be connected to the X=Y1 and M=Y2 (when Y2 is present) groups.

In some embodiments elements and/or functional groups comprised in A are configured to link moiety

(III)

of Formula (II) which provides a catalytic core of the catalyst wherein Y1 is catalytic site.

In some embodiments A comprises various combinations of O, NH—, P, As, Sb, Bi, S, Se, Te, Po and various metals such as V, Nb, Ta, Cr, Mo, W, Mn, Tc, Re, Fe, Ru, and Os linked together with element M and X with one or more covalent bonds in accordance with the structure of Formula (II). In some embodiments, M can be V or Mo, and X can be P or Te. In some embodiments, M and X according to Formula (II) can be linked to an A moiety of any one of formula (IV), (V), (VI), (VII), (VIII) and (IX).

In some embodiments, Y1 can be an oxygen and i is 1; X is phosphorus or a substituted or unsubstituted Te; Z is oxygen and j is 1; M is vanadium or molibdenum; and Y2 is oxygen k is 1.

In some embodiments, Y1 c oxygen and i is 1; X is Te—OH; Z is oxygen and j is 1; M is vanadium or $Mn^{+5}$; and Y2 is oxygen and k is 1.

In some embodiments, A can further comprise one or more catalytic cores. In particular, in some embodiments, A presents a plurality of additional catalytic cores of formula (III) wherein Y1, X, Z M and Y2 of each additional catalytic core are independently selected among Y1, X, M and Y2 wherein:

Y1 is an element or functional group selected from the group consisting of O and NR', wherein R' is a hydrogen, substituted or unsubstituted alkyl, alkenyl, or aryl group, Y1 being capable of forming a Y1-H single bond with the H from the R—H substrate, and the Y1-H single bond having a Y1-H enthalpy;

X is a column 15 or 16 element capable of forming a double bond to Y1;

Y2 is an element or functional group selected from the group consisting of O and NR', wherein R' is a hydrogen, substituted or unsubstituted alkyl, alkenyl, or aryl group;

M is an element selected from the group consisting of V, Nb, Ta, Cr, Mo, W, Mn, Tc, Re, Fe, Ru, and Os;

Z is an element or functional group selected from the group consisting of O and NH;

i is 1-2;

j is 0-1;

k is 0-1;

and wherein Y1, X, Z, M, and Y2 are selected such that the Y1-H single bond enthalpy is equal or lower than the R—H single bond enthalpy.

In some embodiments, in the one or more catalytic cores comprised in A, Y1 is oxygen and i is 1; X is phosphorus; Z is oxygen and j is 1; M is vanadium; and Y2 is oxygen k is 1.

In some embodiments, in the one or more catalytic cores comprised in A, Y1 is oxygen and i is 1; X is Te—OH; Z is oxygen and j is 1; M is vanadium; and Y2 is oxygen and k is 1.

In some embodiments, catalytic cores of formula (III) and supporting moieties A can be linked to form a catalytic matrix for activation of a R—H bond in one or more R—H substrates of formula (I).

In particular, in some embodiments, the catalytic matrix comprises a plurality of catalytic cores of Formula (III) wherein Y1, X, Z, M, and Y2 of at least a portion of the catalytic cores of Formula (III) are selected such that the Y1-H single bond enthalpy is equal or lower than the R—H single bond enthalpy of one or more substrates to be activated by the matrix.

In particular, in embodiments herein described in the catalytic matrix the M and X of each catalytic core of the plurality of the catalytic cores of Formula (III) are connected to a supporting moiety A which comprises a plurality of elements and/or functional groups linking the M and the X of each catalytic core of the plurality of the catalytic cores of Formula I. in the catalytic matrix the supporting moiety A configured to form a framework presenting Y1 of each catalytic core of the plurality of the catalytic cores for reaction with a substrate R—H. In particular, in some embodiments, the supporting moiety A can have any the features of any one of the formulas (IV) to (IX).

In particular, in some embodiments, the plurality of catalytic cores comprising the catalytic matrix can comprise a same or different Y1, X, M and Z.

In some exemplary embodiments, a catalytic matrix can comprise a same catalytic core presented in the matrix for reaction with one or more RH substrates of formula (I). For example, in some embodiments, a catalytic matrix can comprise at least about 75% at least about 85% at least about 90% of a catalytic core VOPO$_4$ presenting P═O and V═O groups to catalyst substrates In some embodiments, the catalytic matrix can comprise a plurality of catalytic cores comprising different Y1, X, M and Z. For example, catalytic matrices herein described can comprise a plurality of catalytic cores such as VOPO4.

In some of those embodiments, the different catalytic cores can result the catalytic matrix comprising at least about 5% of a first catalytic core, at least about 30-50% of a second catalytic core, at least about 45-65% of a third catalytic core.

In some embodiments, different catalytic cores can be located in selected portion of the matrix in connection a reaction to be activated.

In some embodiments, the framework comprised in the catalytic matrix comprises a plurality of layers, each layer of the plurality of layer presenting one or more catalytic cores configured to activate one or more R—H substrate.

In particular, in some embodiments, the catalytic cores can be designed and selected based on the particular substrates to be activated. By way of example, in a multistep reactions (e.g. the conversion of propane to acrolein to acrylonitrile), various intermediates of the reaction undergo R—H bond activation as part of the steps of the transformation. With knowledge of the R—H bond enthalpies (which can either be known experimentally or determined according to computational methods; see e.g. Example 16), the appropriate catalytic cores can be designed and provided according to methods described herein to provide catalytic cores with Y1-H bond enthalpies equal to or below the R—H bond enthalpies of the R—H bonds activated at each step of the transformation. The catalytic matrix can then be configured to have different percentages to each type of catalytic core (the cores either within the same layer or with each type of core in a different layer) so as to ensure that the appropriate intermediates are activated by the appropriate cores to avoid side reactions and thus improve yield and selectivity.

In particular, in some embodiments, each layer of the plurality of layers presents at least about 5% of a first catalytic core, at least about 30-50% of a second catalytic core, at least about 45-65% of a third catalytic core.

In addition, also described herein is method of selecting a catalyst for activation of a R—H bond in a R—H substrate of formula (I). The method comprises selecting the catalyst of formula (II) having the Y1-H bond enthalpy equal or lower than the R—H single bond enthalpy.

In embodiments herein described, catalysts, catalytic cores and/or catalytic matrices herein described can be used in methods of activating an R—H bond in an R—H substrate.

In some embodiments, the method comprises: providing the R—H substrate comprising the R—H bond, the R—H bond having an R—H bond enthalpy and contacting a catalyst of Formula (II) herein described and/or a catalytic matrix herein described with the R—H substrate for a time and under conditions to allow the interaction between the Y1 element or functional group of the candidate catalysts with the R—H substrate. In some embodiments, the contacting is followed by detecting activation of the R—H bond following the contacting.

In some embodiments, the catalyst of formula (II) can be comprised within a catalytic matrix herein described. In particular, in some of those embodiments, the supporting moiety A of the catalyst of formula (II) can comprise one or more catalytic cores of formula (III) to form a structure in which catalytic cores comprised within the matrix are presented in the catalytic matrix for reaction with the R—H substrate of formula (I).

In particular, in some embodiments, the catalyst used in the method is a catalyst of Formula (II), wherein: Y1 is oxygen and i is 1; X is phosphorus; Z is oxygen and j is 1; M is vanadium; and Y2 is oxygen k is 1; and the R—H provided is methane, ethane, propane, butane, or pentane.

In particular, in some embodiments, the catalyst used in the method is a catalyst of Formula (II), wherein Y1 is oxygen and i is 1; X is Te—OH; Z is oxygen and j is 1; M is vanadium; and Y2 is oxygen k is 1; and wherein the R—H provided is ethene or ethyne.

In some embodiments, the catalyst, catalytic cores and/or catalytic matrices herein described can be provided as a part of systems to perform a reaction for the activation of a R—H bond in a R—H substrate of Formula (I).

In a system, the multi-catalyst, catalytic cores and/or catalytic matrices and one or more substrate to perform the R—H activation can be comprised in the system independently.

In particular, in some embodiments, the a system can comprise one of more substrates R—H wherein R is an organic moiety selected from the group consisting of substituted or unsubstituted alkyl, alkenyl, alkynyl, and aryl groups and the R—H bond having an R—H bond enthalpy; and one or more catalyst as herein described wherein Y1, X, Z, M, and Y2 are selected such that the difference between the Y1-H bond enthalpy and the R—H bond enthalpy of the one or more substrates is equal or less than 25 kcal/mol.

Additional components can include reagents and systems to perform the reaction and/or detection of the product which can be performed according to procedures and techniques identifiable by a skilled person based on the catalyzed reaction.

Further advantages and characteristics of the present disclosure will become more apparent hereinafter from the following detailed disclosure by way or illustration only with reference to an experimental section.

EXAMPLES

The following examples are disclosed for further illustration of the embodiments and are not intended to be limiting in any way.

Example 1

Synthesis and Analysis of Catalysts

Catalysts according to embodiments herein described can be synthesized by methods used to synthesize similar catalysts such as, for example, VPO.

Several different phases of the VPO catalyst, including the $\alpha_1$-, $\beta_2$-, $\beta$-, and $X_1$—$VOPO_4$ as well as $(VO)_2P_2O_7$, can be synthesized according to the procedures detailed in, for example, [Ref 16, 17].

For example, $X_1$—$VOPO_4$ can be synthesized by boiling a solution of $NH_4H_2PO_4$ (ammonium dihydrogen phosphate) with $V_2O_5$ powder, isolating the precipitate which consists of $NH_4HVPO_6$, and treating the solid with $O_2$ flow at 823 K.

Computational Analysis

The following computational techniques were used:

The density functional calculations with periodic boundary conditions were performed using the Perdew-Burke-Ernzerhof (PBE) functional [Ref 18], as implemented in the Quantum Espresso code.

Ultrasoft pseudopotentials (USPPs) [Ref 19] with a plane-wave basis set and a cutoff energy of 30 Ry for wavefunctions and 240 Ry for charge density was used.

Electron smearing was employed using the Gaussian-smearing technique with a width of 0.01 Ry.

For bulk structures, the Brillouin zone was sampled with 3×3×4 Monkhorst-Pack k-point grid [Ref 20] for $\alpha_1$- and $\alpha_2$-$VOPO_4$, and 2×2×2 for $\beta$-, $X_1$—$VOPO_4$ and $(VO)_2P_2O_7$. For slab calculations, the Brillouin zone was sampled with 3×3×1 k-point net for $\alpha_1$- and $\alpha_2$-$VOPO_4$ surfaces, and 2×2×1 for $X_1$—$VOPO_4$ and $(VO)_2P_2O_7$ surface.

About 8 Å vacuum space between adjacent slabs was used to prevent the interaction between the replicas along the z direction. Transition states were located by using the "climbing-images" nudged elastic band (CI-NEB) method [Ref 21, 22].

Figure 4:
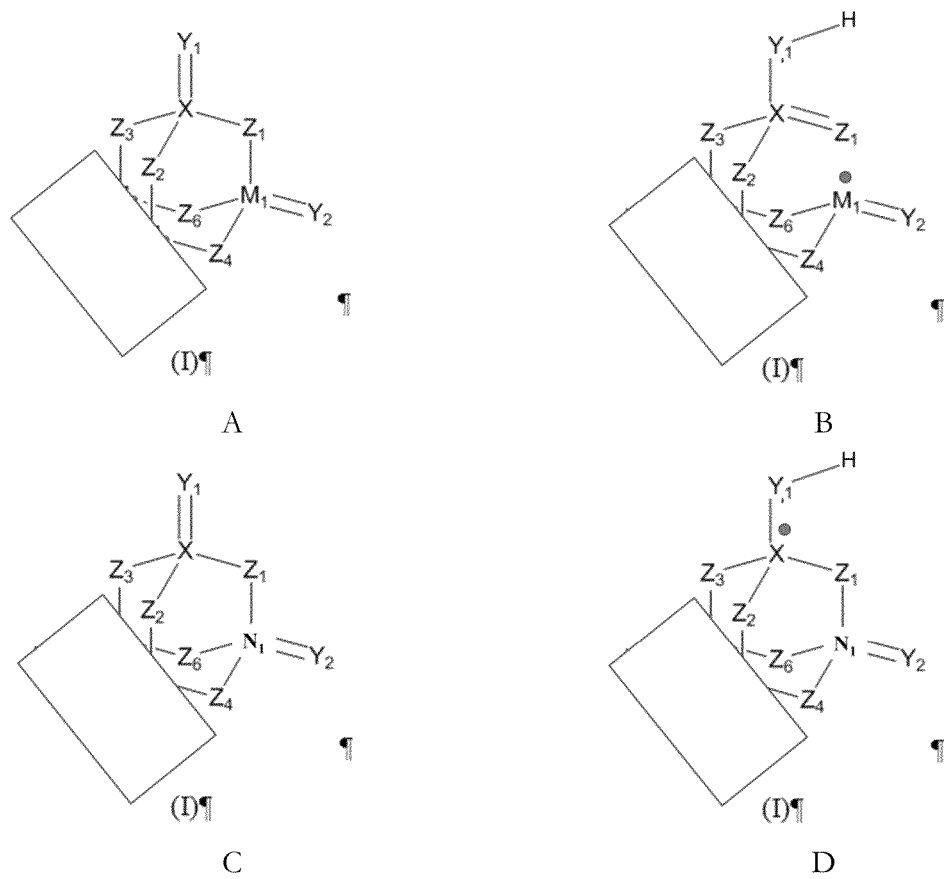
FIG. 4 shows schematic representations of different states of ROA and non-ROA catalysts (I).

For most of the structures except different phases of $VOPO_4$ and the reactants of FIGS. 4 (a), (b), (c), (d), and (e), spin-polarized k wavefunction is utilized.

Calculations using the VASP code with the same k-point net to sample the reciprocal space, projector augmented-wave (PAW) pseudopotentials, and the setting PREC=ACCURATE were also performed. $D_H$'s to be 49.9, 50.8, 52.1, 45.2, and 82.4 kcal/mol for O(1) and O(2) on the $\alpha_I$-$VOPO_4$ surface, and O(1) and O(2) on the $\alpha_{II}$-$VOPO_4$ surface, and O(1)=P on the $X_1$—$VOPO_4$, respectively were also calculated. Those numbers are similar to those obtained by the Quantum Espresso code with USPPs (48.5, 49.2, 52.1, 45.2, and 84.3 kcal/mol), indicating the use of USPPs gives essentially the same results as those using PAW.

In order to reduce the computational cost, the following additional techniques were also used: (i) the high pressure, high symmetry form of VOPO [Ref 23], which has four molecular units per unit cell as compared to the ambient pressure, low symmetry form of VOPO with eight units was used [Ref 24]; (ii) it was found that the band structures, projected density of states, and Mulliken charge distribution are very similar for the two forms, and hence it is expected the surface chemistry to be similar [Ref 4]; (iii) additionally since all the chemistry is initiated by the O(1)=P active site, the binding energy ($D_H$) of a free hydrogen atom to O(1)=P using the low symmetry, ambient pressure form of oxidized VOPO ($X_1$—$VOPO_4$) was calculated and compared the result to that using the high symmetry, high pressure form of oxidized VOPO. It was found that the two $D_H$'s are quite similar (86.1 kcal/mol vs. 84.3 kcal/mol). As a result, it is expected that the results based on the high symmetry form are similar to those that would be obtained using the low symmetry model.

The model was then validated.

Optimization of the cell parameters of $(VO)_2P_2O_7$ (OK) by the PBE functional leads to a=7.624 Å, b=9.661 Å, and c=8.445 Å, in good agreement with experiment (a=7.571 Å, b=9.536 Å, and c=8.362 Å at 300K) with deviations of 0.7, 1.3, and 1.0%, respectively [Ref 23].

Since the atoms within the layers on the bc plane connect to adjacent bc layers through interlayer P—O—P bonds along the a direction, it is expected that London Dispersion (van der Waals attraction) can play an important role. Therefore, the cell parameters were re-optimized with dispersion-corrected PBE (PBE-D2) functional [Ref 25] were re-optimized to obtain a=7.447 Å, b=9.558 Å, and c=8.446 Å, which deviate from the experimental values by −1.6, 0.2, and 1.0%, respectively. This shows that PBE-D2 reduces the error in the calculated cell volume but that the error in the a parameter goes from +1.0% to −1.6%.

The reaction energy of atomic hydrogen to O(1)=P (which was identify as the active site for the VPO chemistry) using PBE-D2 leading to 87.5 kcal/mol for PBE-D2 compared to 84.3 kcal/mol for PBE was also re-calculated. Thus, it was conclude that the results from PBE are similar to those based on PBE-D2.

For small finite clusters, geometry optimizations were carried out using the same functional as implemented in the Jaguar code with the 6-31G basis set [Ref 26, 27] for all atoms except V. For V, the first two shells of core electrons were described by the Los Alamos angular momentum projected effective core potential (ECP) using the double-ζ contraction of valence functions [Ref 28] (denoted as LACVP).

Computational Results
Optimization of the VOPO Bulk Structure

Figure 5:
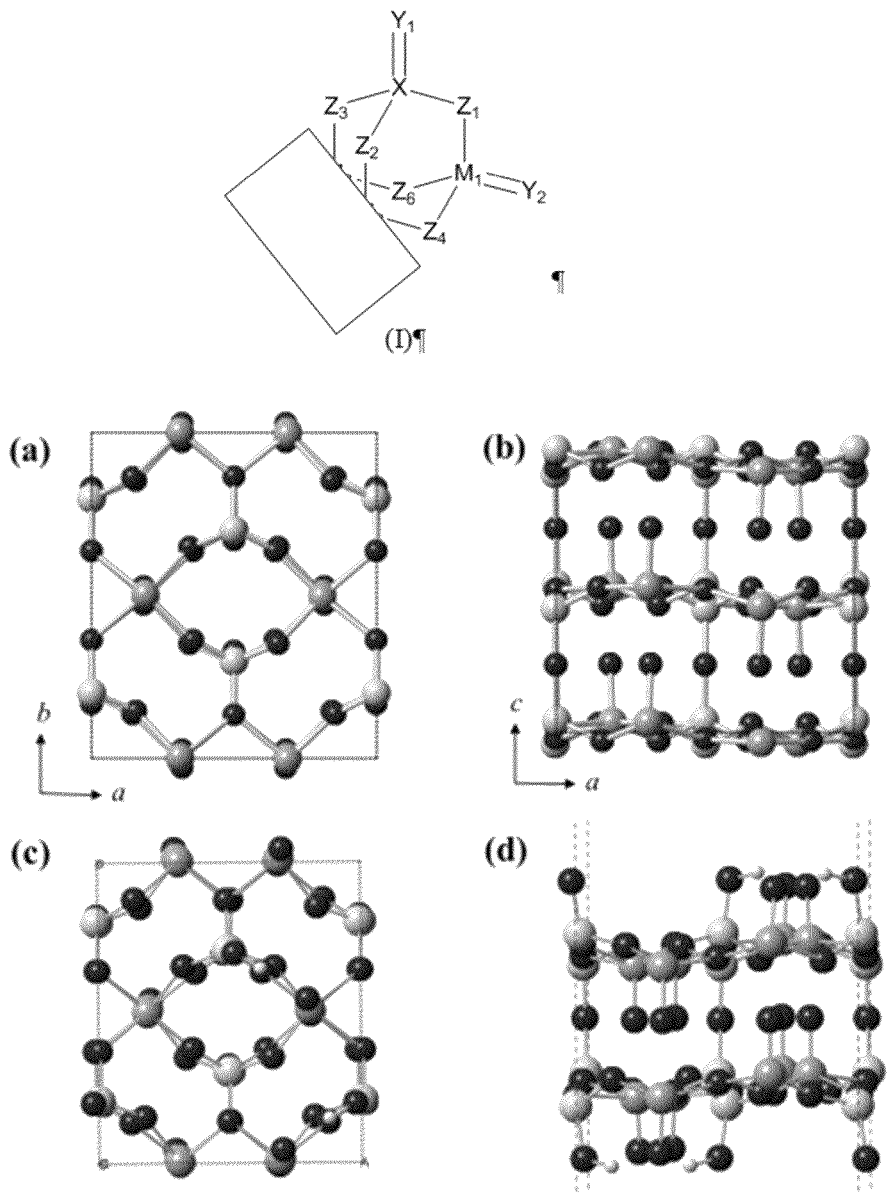
FIG. 5 shows (I), and the top and side views of the bulk (a,b) and surface (c,d) VOPO.

A full optimization of the VOPO bulk structure (FIG. 5), including atomic positions and cell parameters under orthorhombic symmetry was first carried out.

The VOPO surface model used in this work was prepared by cutting the DFT-optimized bulk structure parallel to the ab-plane, cleaving the P—O—P interlayer bonds. It is generally agreed that the active sites involved in n-butane oxidation to MA are on this surface [Ref 18, 24]. The cleaved sites were capped with either hydrogen atoms or hydroxyl groups so that vanadium and phosphorus are maintained at the +4 and +5 oxidation state, respectively, while keeping the surface unit cell neutral. The total number of atoms in the unit cell is 58, which includes eight vanadium, eight phosphorus, four OH, and 34 oxygen atoms. Saturating the cleaved P—O bonds in this way is reasonable since Busca et al. observed that such P—OH motifs exist on the VOPO surface with vibrational frequencies of 2600 to 3600 cm$^{-1}$ [Ref 29].

Evaluation of C—H Activation Power of Various Oxygen and Vanadium Atoms on the VOPO Surface and of Dissociative Adsorption of $O_2(g)$ onto the VOPO Surface The C—H activation power of various oxygen and vanadium atoms on the VOPO surface was evaluated, by calculating the binding energies of these atoms to a free hydrogen atom ($D_H$) [Ref 30, 31].

The C—H activation powers of various lattice oxygen atoms can be evaluated quickly by simply calculating their binding energies to a free hydrogen atom ($D_H$) [Ref 30, 31]. The alkane C—H bond cleavage on the metal oxide surface usually proceeds through a hydrogen abstraction pathway, leading to the formation a surface O—H species and a weakly bounded alkyl radical. During this process, a C—H bond is broken and an O—H bond is formed. Since the strength of the C—H bond is a constant, the stronger the new formed O—H bond is, the more stable the product is, and according to the Hammond's postulate the smaller is the reaction barrier.

It was found that none of the surface oxygen or vanadium atoms can carry out facile n-butane C—H activation. The largest $D_H$, from the O(1)=V (vanadyl) group, is only 58.2 kcal/mol, compared to a bond dissociation energy of 98.3 kcal/mol [Ref 32] for the weakest C—H bond in n-butane. Therefore C—H cleavage by O(1)=V would pose a barrier higher than 40.0 kcal/mol, which is far larger than the experimental values ($E_a$=12.9 to 23.6 kcal/mol, depending on the degree of oxidation of VPO) [Ref 33].

Figure 6:
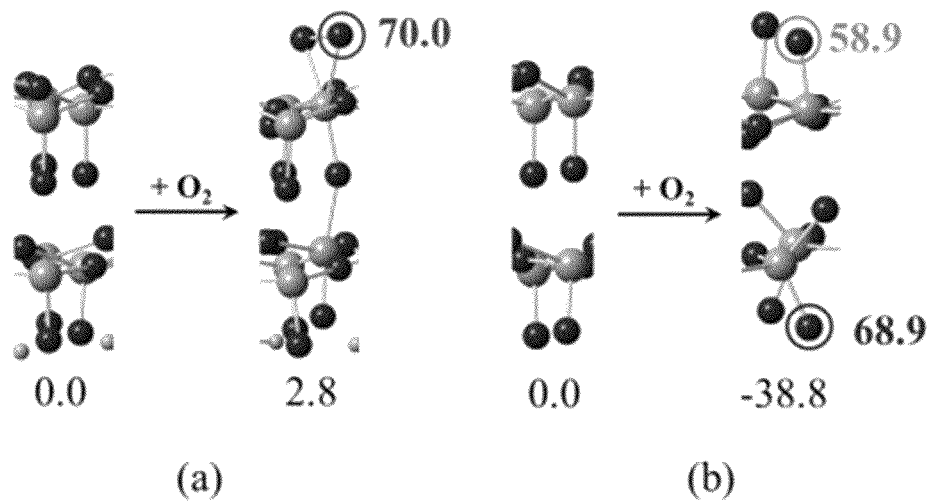
FIG. 6 shows oxygen adsorption energies on the (VO)2P2O7 surface and their DH's (unit is in kcal/mol).
Figure 7:
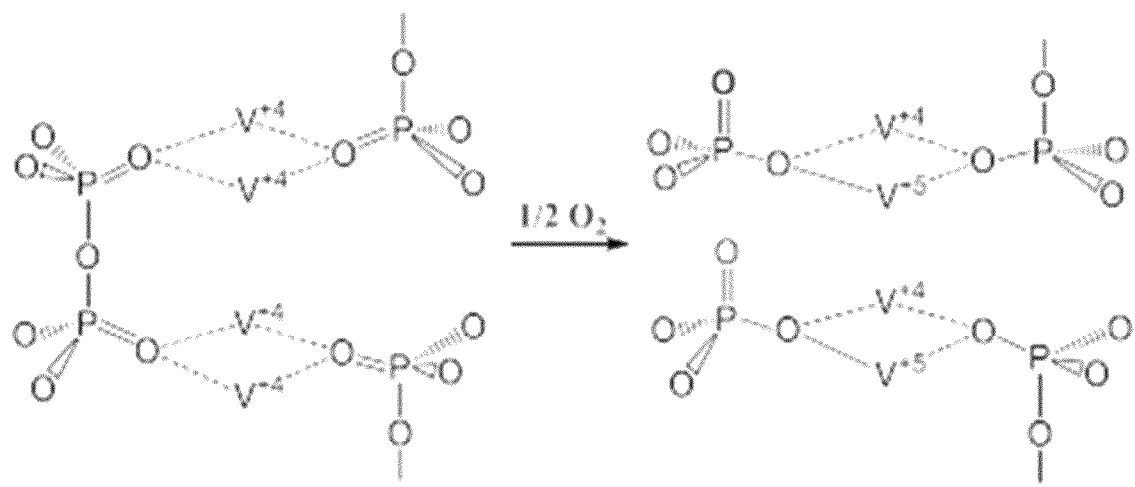
FIG. 7 shows valence bond description of pyrophosphate oxidation.

It has been proposed that gaseous $O_2$ may adsorb on the VOPO surface in a molecular or dissociative fashion, oxidizing $V^{IV}$ to $V^V$ and forming very reactive oxygen species in the form of $O^-$, $O_2^{-1}$, or $O_2^{-2}$ [Ref 11, 34, 35]. This possibility was investigated and found unlikely. The binding of $O_2$ to the VOPO surface is uphill by 2.8 kcal/mol (electronic energy) rather than downhill (FIG. 6 (a)), even though two $V^{IV}$ do oxidize to $V^V$. Moreover, it is found that gaseous $O_2$ chemisorbed to the vanadium, leads to a $D_H$ from the oxygen of peroxyl of 70.0 kcal/mol, indicating that the C—H activation barrier would be at least 30 kcal/mol.

The dissociative adsorption of $O_2(g)$ onto the VOPO surface was also considered. Two oxygen atoms were added to the top of vanadium (the position trans to O(1)). Geometry optimization leads to the formation of two new O=V bonds but simultaneously pushes the two original O(1) atoms to bind with V=O(1) on the second layer, forming two trans-vanadium dioxo motifs (O(1)-V—O(1), FIG. 6(b)) on the other side of the surface. Lowdin spin density analysis was carried out to find that the two newly added oxygen atoms possess some radical character (0.15 e$^-$), but their $D_H$'s are only 58.9 kcal/mol. Trans-dioxo species are rare for first row transition metals [Ref 36]; however, it has been reported recently for the Mn porphyrin system [Ref 37], and is known to activate weak alkane C—H bonds. For the current VOPO system, the $D_H$ of the trans-dioxo vanadium motif is only 68.9 kcal/mol, indicating a minimum barrier for n-butane C—H activation higher than 30 kcal/mol. These results indicate clearly that neither the oxygen on the VOPO surface nor adsorbed $O_2$ (molecularly or dissociatively) is the active site for initial n-butane C—H activation. From experimental studies of the same oxidation reaction catalyzed on supported vanadia, Wachs et al. reached the same conclusion [Ref 38, 39].

Figure 10:
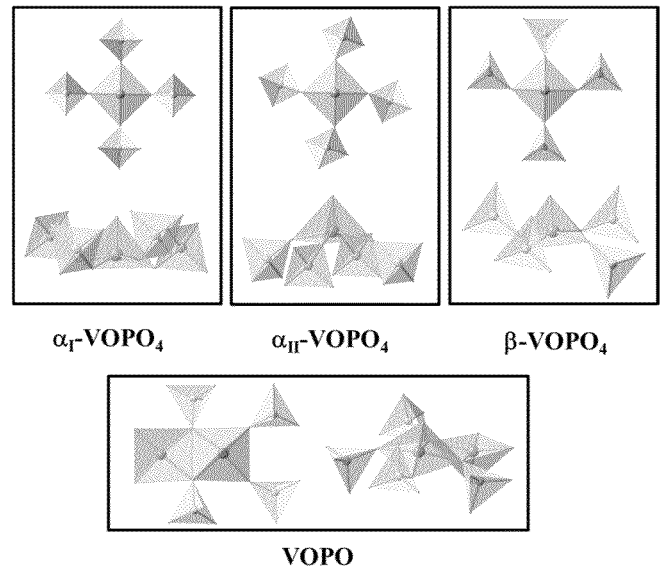
FIG. 10 shows the local environment of vanadium at different phases of VOPO4 and VOPO. The larger polyhedron represents the VO6 or V2O8 motif, while the smaller tetrahedron represents PO4 or P2O7.
Figure 11:
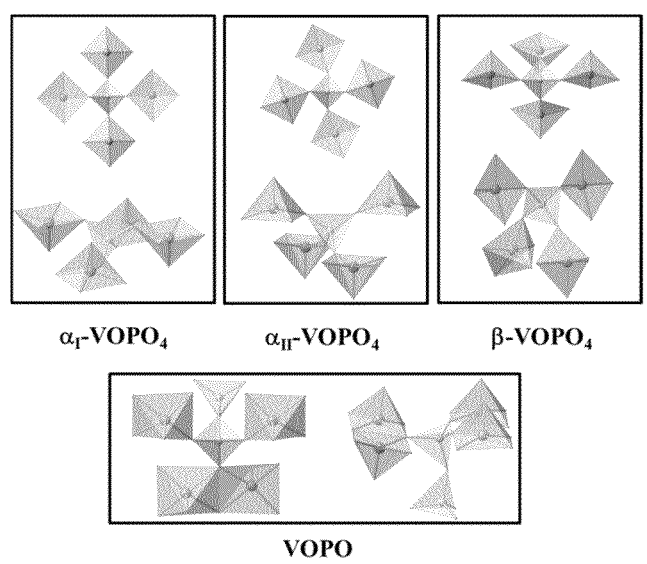
FIG. 11 shows the local environment of phosphorus at different phases of VOPO4 and VOPO. The larger polyhedron represents the VO6 or V2O8 motif, while the smaller tetrahedron represents PO4 or P2O7.

Experiments show that the surface of the working catalyst contains small amounts of various phases of $VOPO_4$ [Ref 14, 15]. This opens a possibility that $V^V$, which is known to activate alkanes and furan [Ref 40], can come from $VOPO_4$. Interestingly, when comparing the structures of well-defined $VOPO_4$ structures ($\alpha_I$, $\alpha_{II}$, and β phase) to VOPO, it is found that no significant structural change takes place at vanadium atoms. Instead the major changes are at phosphorus (FIG. 10 and FIG. 11). In VOPO each phosphorus atom binds to one O—P (forming P—O—P bonds to link two adjacent layers) and three O—V motifs, whereas in $VOPO_4$ phosphorus binds with four O—V motifs.

This suggests that the oxidation of VOPO to $VOPO_4$ may occur by adding oxygen to phosphorus, converting one pyrophosphate into two ortho-phosphates (Scheme 1). In this way, two of the dative bonds in the V—(O)$_2$—V motif of VOPO become covalent, and concurrently, two $V^{IV}$ are oxidized to $V^V$. [Ref 4] This increase in the oxidation state for vanadium may enhance the reactivity of the surface oxygen toward n-butane C—H activation.

Study of Bulk $VOPO_4$ and the Corresponding Surfaces

Figure 12:
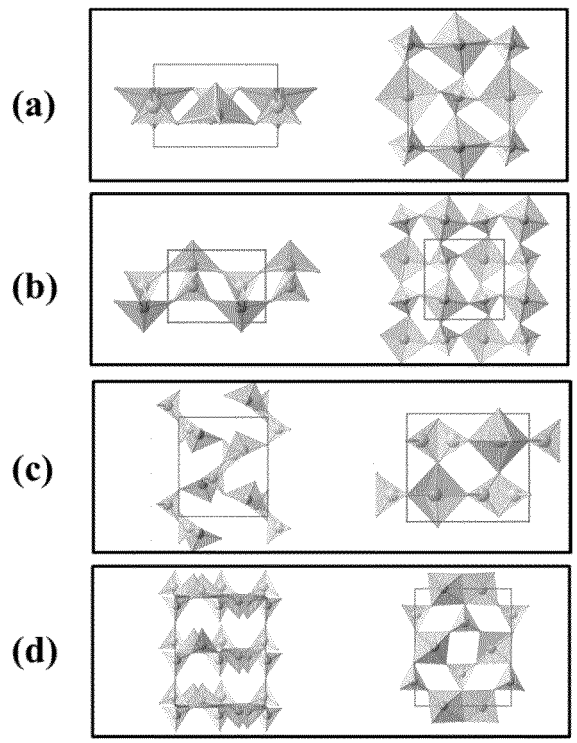
FIG. 12 shows $\alpha_I$- (a), $\alpha_{II}$- (b), β- (c), and X1-phase (d) of VOPO4. $\alpha_I$, $\alpha_{II}$, β-, and X1-VOPO$_4$ contain two, two, four, and eight formula units, respectively.

In order to verify the hypothesis, bulk $VOPO_4$ and the corresponding surfaces were studied. Besides the well-defined $\alpha_I$, $\alpha_{II}$, and β-phase of $VOPO_4$ (FIG. 12), a proposed $X_1$-phase [Ref 16, 17] was also investigated. This phase is proposed to form by directly adding an oxygen to the P—O—P motif, after which the O(1)=P—O(1)=P motifs are formed and vanadium is oxidized to the +5 state, leading to a layered structure. It is considered that this is likely to be the precursor for forming other phases, and that the transformations are through coordinating O(1)=P to the nearby vanadium atoms.

Stability of Bulk $VOPO_4$.

By comparing the energies of different phases of $VOPO_4$ to $VOPO+2\times O_2(g)$, it is found that the β-phase is the most stable with an energy −218.6 kcal/mol more stable than $VOPO+2\times O_2(g)$. This is followed by $\alpha_{II}$-phase (−211.2 kcal/mol) and then $\alpha_I$ (−193.4 kcal/mol). This order is consistent with experiments [Ref 41]. The proposed $X_1$-phase is only −49.6 kcal/mol downhill, corresponding to an adsorption energy of −24.8 kcal/mol per $O_2(g)$. This suggests that it is a metastable state.

The studies start with surface layers of the VPO catalyst that are extensions of the bulk VOPO and examine how oxidation by $O_2$ converts them into $VOPO_4$. Some experimental studies suggest that the surface layers are amorphous after annealing [Ref 42], which indicates that there is no long range order (>25 Å). For convenience in the QM, long range order is assumed, but the characters of the sites discussed require only local order. Thus the conclusions do not require long range order.

Figure 13:
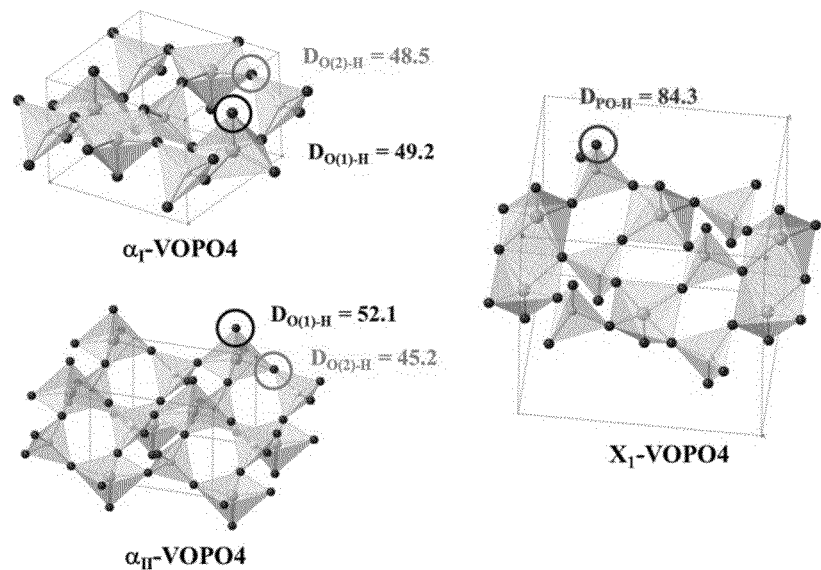
FIG. 13 shows crystal structures of the $\alpha_I$, $\alpha_{II}$, and X1-VOPO$_4$ and the corresponding $D_H$'s for their surface oxygen atoms.

The cell parameters and atomic positions of these $VOPO_4$ phases under orthorhombic symmetry were first optimized, and the C—H activation power of various oxygen sites on these VOPO$_4$ surfaces were then evaluated, focusing on $\alpha_I$, $\alpha_{II}$, and X$_1$ surfaces, due to their layered structures. All surfaces were prepared by cleaving parallel to the layer direction in such a way that only van der Waals interactions are broken. Surprisingly, it is found find that D$_H$'s for the $\alpha_I$-surface are 49.2 and 48.5 kcal/mol for O(1) and O(2) sites, respectively, and D$_H$'s for the $\alpha_{II}$-surface are 52.1 and 45.2 kcal/mol for O(1) and O(2) sites, respectively (FIG. 13). This indicates clearly that none of the oxygen sites on the $\alpha_I$- or $\alpha_{II}$-surfaces can be the reactive center for VPO chemistry. Although the surface of the β-phase was not evaluated, it is expected the oxygen atoms on the β-phase to have similar D$_H$'s, and as a result none of them is expected to present a low barrier pathway for cleaving alkane C—H bonds.

Interestingly, during the course of evaluating the D$_H$ of O(1)=V on the X$_1$-surface, it was found that structural optimization pushes hydrogen that is initially placed to bind with O(1)=V to bind instead with the oxygen of O(1)=P. Most importantly this leads to a D$_H$ of 84.3 kcal/mol, which is 26.1 kcal/mol larger than that of O(1)=V on the VOPO surface and 14.3 kcal/mol larger than that of the vanadium peroxyl. Analyzing the spin density, it is found that although the proton is bound to O(1)=P the electron is delocalized among two nearby vanadium atoms (0.61 e– and 0.45 e–, Lowdin charge). A single-point calculation using the B3LYP functional with Gaussian basis sets (double-zeta quality) leads to a similar spin distribution. This indicates that after the hydrogen abstraction by O(1)=P, it is vanadium that is reduced. A similar phenomenon is observed in the oxidative dehydrogenation of methanol to formaldehyde catalyzed by vanadia/ceria [Ref 43].

Calculating the barrier with QM it is found that this highly reactive O(1)=P site activates the n-butane methylene C—H bonds with a barrier of only 13.5 kcal/mol, which is in the range of experimentally estimated values (12.9 to 23.6 kcal/mol) [Ref 33]. Thus it is proposed that O(1)=P on the metastable X$_1$—VOPO$_4$ surface is the active center for initiating the VPO chemistry. This conclusion is in stark contrast to the common assumption that pyrophosphate or phosphate is the linked ligand and is catalytically inactive. This is also in contrast to all previous speculations of the mechanism based on experimental [Ref 3, 11] and theoretical studies [Ref 4-8], which suggested that the reactive center is either a V—O bond [Ref 3] or chemisorbed O$_2$ on vanadium [Ref 11]. Since, pyrophosphates and phosphates are common components in heterogeneous catalysts, it is speculate that they may play a key role for some of these catalytic systems as for the VPO system [Ref 44, 45].

Since the V metal is reduced during C—H activation, changes in the reduction potential of the V by binding it with electron-donating ligands such as water or replacing it with other metals is expected to change the reactivity of the VPO catalyst. For example, calculations performed by the inventors show that when water is bound with vanadium, D$_H$ of the nearby O(1)=P decreases from 84.3 to 78.1 kcal/mol. This is consistent with the experiments showing that water vapor decreases the VPO reactivity [Ref 46]. The addition of other metals such as Cr, Fe, and Cu as promoters is expected to change the reduction potential of the electron sink, which in turn is also expected to change the intrinsic reactivity of VPO. Indeed such promoters are widely most utilized in most commercial VPO catalysts [Ref 47].

Wachs et al. used in situ Raman spectroscopy to study the same oxidation using supported vanadia catalysts [Ref 38, 39]. They found that the addition of P$_2$O$_5$ phosphate additives increases the MA selectivity. Based on this observation they concluded that the V—O—P bond is the active site for the rate-determining-step. The inventors agree with this conclusion, but find more specifically that it is a O=P—O—V=O unit in which the phosphate is coupled through a bridging O to the V=O bond of V in +5 oxidization state. Also it is found that it is the P=O bond that activates the C—H bond of n-butane (not the V=O). It is not clear whether the P—O—P bonds of the additive are retained in the model catalyst. If they are, then it can be considered that the Wachs' model system may operate under the same mechanism as discovered for VPO. The activity would be expected to be less since the model system may not have the layer to layer integrity of the VPO catalyst. If the model catalyst does not retain the P—O—P units, then it may operate differently. Perhaps experimental tests would be to replace the P$_2$O$_5$ additive with PO$_4$.

Utilizing a non-metal oxo bond (such as P=O or S=O) to activate alkane C—H bonds would be ideal, since it would avoid the direct use of expensive metals at the active center [Ref 48]. Recently, this idea has been explored by Schwarz et al. [Ref 49], who used [P$_4$O$_{10}$]$^{•+}$ to activate methane C—H bonds, and by de Petris et al. [Ref 50], who used [SO$_2$]$^{•+}$ also to activate methane.

The inventors' current results show that bridging a non-metal oxo to a high-valent metal acting as an electron reservoir would be able to activate alkane C—H bonds without being excited to the cation radical state. This idea is also valid for finite molecules. For example, D$_H$ of P$_4$O$_{10}$ (Scheme S1 (a)) is calculated to be only 28.2 kcal/mol. However, replacing one O(1)=P motif by O(1)=V (b), it is found that D$_H$ increases to 60.5 kcal/mol. It is expected that the D$_H$ would be larger if a more electrophilic high valent metal ion such as Fe or Co is used. This concept can be utilized to design a new class of homogeneous C—H activation catalysts.

Ability of Highly Reactive Surface of X1-VOPO4 to Convert n-Butane to MA

Figure 8:
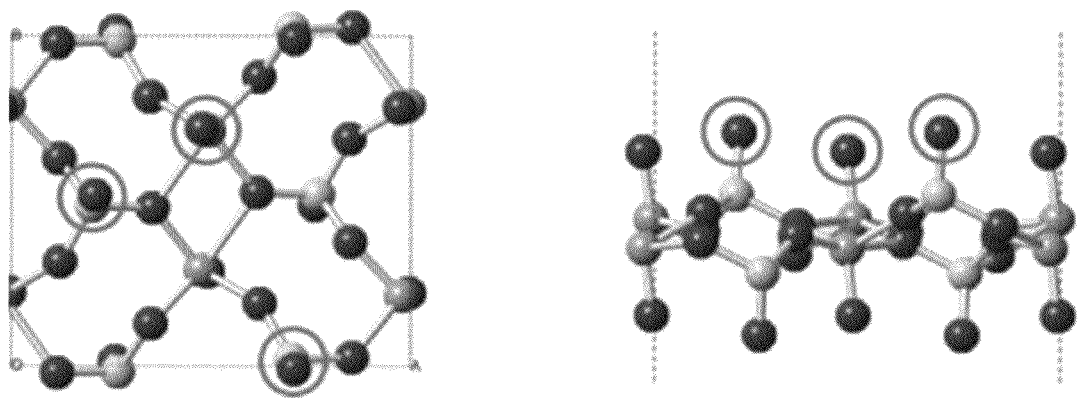
FIG. 8 shows one-layer X1-VOPO4 surface model (The circles mark the sites involved in n-butane to MA oxidation).

To demonstrate that the proposed highly reactive surface of X$_1$—VOPO$_4$ is able to convert n-butane all the way to MA, the subsequent steps of this oxidation reaction with a one-layer model were studied (FIG. 8). In this preliminary reaction mechanism study, the olefinic route mechanism, in which n-butane is first converted to butene, butadiene, dihydrofuran, crotonlactone, and finally MA [Ref 9, 51] was focused on. It should be noted that after each conversion, the product desorbs and then react with a fresh surface.

Figure 9:
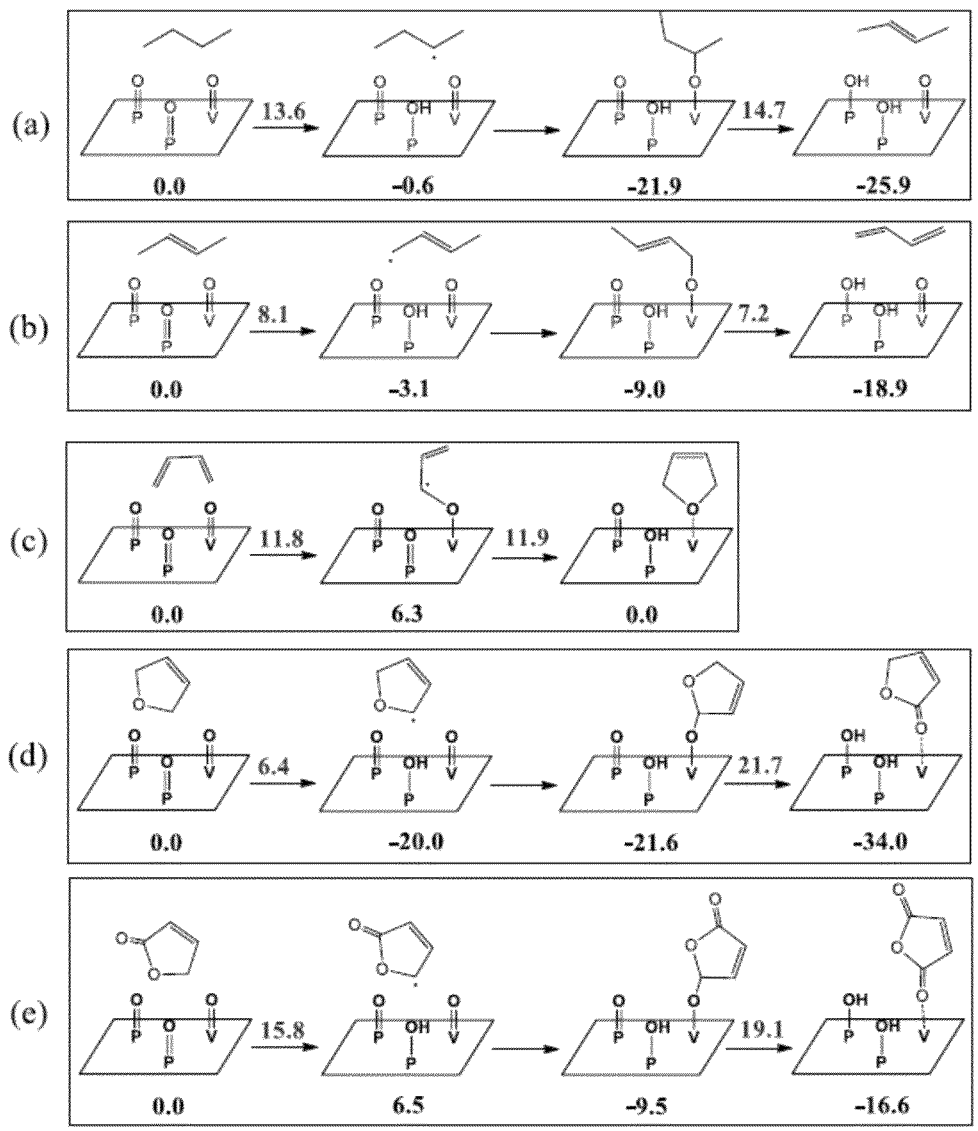
FIG. 9 shows schematic description of a pathway for n-butane oxidation all the way to MA. Each number at the bottom of each panel represents the potential energy in kcal/mol, while numbers over the arrows represent the reaction barriers.

The oxidative dehydrogenation of n-butane to 2-butene and 2-butene to butadiene (FIGS. 9 (a) and (b)), butadiene to 2,5-dihydrofuran (FIG. 9 (c)) and the oxidation of 2,5-dihydrofuran to crotonlactone and crotonlactone to MA ((d) and (e)) go through similar pathways: hydrogen abstraction by O(1)=P, with the hydrocarbyl radical trapped on O(1)=V, and then another hydrogen abstraction by another O(1)=P. The highest barriers are 14.7 kcal/mol for n-butane→2-butene and 8.1 kcal/mol for 2-butene→butadiene, while they are 21.7 kcal/mol for 2,5-dihydrofuran→crotonlactone and 19.1 kcal/mol for crotonlactone→MA. The conversion of butadiene to 2,5-dihydrofuran is through C—O formation and a ring-closing step, with the highest barrier of 18.2 kcal/mol. The overall reaction barrier for the oxidation of n-butane to MA is 21.7 kcal/mol, corresponding to hydrogen abstraction from adsorbed 2,5-dihydrofuran. This result is not consistent with current experimental interpretation which finds the rate-determining step to be activation of the methylene C—H bonds of n-butane with barriers ranging from 12.9 to 23.6 kcal/mol [Ref 33, 52]. This suggests that there may be alternative pathways for the subsequent steps of functionalizing n-butane to MA, with even lower barriers than the 21.7 kcal/mol that were calculated. It is also possible that entropic effects on the surface at operating temperatures might provide lower effective reaction barriers than found in QM pathways along minimum energy surfaces. However, the main goal of this preliminary mechanistic study is to demonstrate that the conversion of n-butane to MA at the P=O site on this surface is very facile with a barrier of not more than 21.7 kcal/mol.

Summarizing, DFT was used to determine the reaction mechanism for n-butane oxidation to MA on vanadium phosphorus oxide surfaces. In contrast to previous suggestions, it is found that surface O(1)=P (formed through the oxidation of pyrophosphate to two ortho-phosphates) is the center that activates n-butane (barrier of 13.5 kcal/mol). This high reactivity of O(1)=P is due to its strong basicity coupled with the large reduction potentials of nearby $V^V$ ions. A full reaction pathway on this surface for oxidizing n-butane all the way to maleic anhydride, with an overall barrier not exceeding 21.7 kcal/mol was also demonstrated. This is consistent with the reaction proceeding down to 673-723 K.

This study provides novel concepts for catalysis for both heterogeneous and homogeneous prospects. It suggests that pyrophosphate or phosphate is catalytically important and is critical to the function of the current VPO system and likely to play a similar role in other heterogeneous systems. It also provides a new concept for designing catalysts that use non-metal oxo bonds instead of metal oxo bonds or metals for homogeneous alkane C—H activation.

Example 2

Synthetic Strategies for General Catalysts Bearing Y=X-Z-M Motifs for C—H Activation The chemical synthesis of $X_1$—$VOPO_4$ as summarized in Example 1, "Synthesis and analysis of catalysts", is a specific case of the above where Y=Z=O, X=P, and M=V.

X can be generalized beyond P to, for example, S, Se, or Te by replacing the $NH_4H_2PO_4$ precursor with the corresponding sulfate, selenite, tellurate, etc. M can be generalized by V to a different transition metal by replacing $V_2O_5$ with the corresponding metal oxide.

Computational Analysis Strategies

Periodic structures may be calculated in the same was as example 1, "Computational Analysis", i.e. with PBE functional, USPPs, and electron smearing.

Small finite models may be calculated as in example 1, "Computational Analysis".

Computational Results

The strategies of the above section may be applied to any generalized catalyst in the same manner as example 1 "Computational Analysis".

The principles in example 1, "Study of bulk VOPO4 and the corresponding surfaces", are also useful Example 3

General Catalyst Structure and Mechanism

Figure 16:
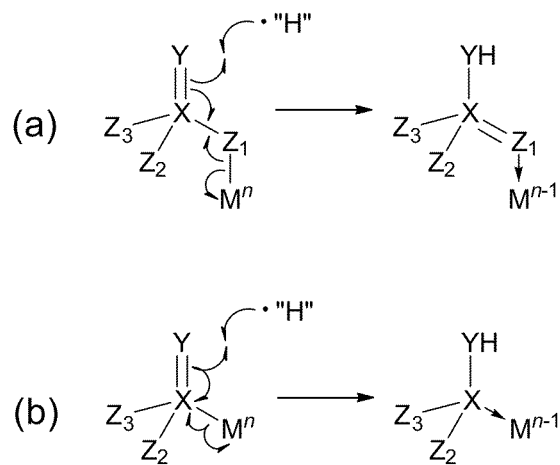
FIG. 16 shows valence bond description for the reduction-coupled oxo activation (ROA) principle.

The inventors have discovered a new mechanism for activating CH bonds, which the inventors call reduction-coupled oxo activation (ROA). The idea is illustrated in FIG. 16. Here, Y indicates an element (such as O, Se, NH, PH, $CH_2$, etc) that can form a double bond to a chemical entity X indicates an element (such as, for example, P, As, Sb, Bi, S, Se, Te, Po) which is coupled through an element Z (such as O or NH) to a metal M in oxidation state n (such as $V^{+5}$, $Mo^{+6}$, etc) that is reducible to oxidation state n−1

The general substrate is R—H, where R can be an substituted or unsubstituted alkyl, alkenyl, alkynyl, aryl, alkoxy, aryloxy, alkylamino, arylamino, or acyl group.

Computational Methods

The geometry optimizations were carried out using the B3LYP functional with the 6-31G** basis set for all atoms except the metals. For metals the small core angular momentum projected effective core potential (ECP) from Los Alamos was used, for which the outer core and valence electrons described explicitly using the double-ζ contraction of valence functions plus polarization. Thus a neural V, Nb, or Ta is described with 13 explicit electrons while Ni, Pd, Pt are described with 18 explicit electrons.

To obtain the most accurate energetics, the energy was calculated at the single optimum geometry-point using the same functional but with a larger basis set: metals were described with the triple-ζ contraction of valence functions augmented with two f-functions but with the core electrons described by the same small core ECP; while the other atoms were described with the 6-311++G** basis set.

The analytic Hessian was calculated for each local minimum and each transition state and used to calculate the vibrational frequencies. The calculated zero-point vibrational energy is not included in the potential energy surface. The discussion of energies in the manuscript is all based on the electronic energy. It was ensured that each local minimum had zero imaginary frequencies, while each transition state structure had exactly one imaginary frequency. All calculations were performed using the Jaguar 7.6 or Jaguar 7.9 program package.

Computational Procedures for Gauging Catalyst Effectiveness.

Computational analysis of the mechanism is expected to reveal the following:

(i) The electron on the "H" reacts with the electron in the orbital on Y previously involved with the pi bond X to form a Y-"H" bond.

(ii) Simultaneously, the X=Y double bond must change to a X—Y single bond since the electron in the pi on Y is bonded to "H", releasing the electron that was in the pi orbital on X.

(iii) Simultaneously, electron previously in the pi orbital on X now forms a pi bond to Z, changing the X—Z single bond to a X=Z double bond so that the X retains the same oxidation state as at the start.

(iv) Simultaneously since the electron in the orbital on Z that was involved in the Z-M bond is now used in the bond to X, the electron from the M that was in this Z-M bond remains on the M, reducing it from the n to the n−1 oxidation state.

It is useful to relate this to the valence bond picture:

Point 1: in Step 1 the "H" atom/group with its electron that previously was bonded to the R group, now forms a sigma bond with the electron in the orbital on Y that was previously in a pi bond to X.

Point 2: the electron in the orbital on X that was previously pi bonded to the electron on Y is now available to form a new bond.

Point 3: this electron now bonds to the electron in the orbital on Z that previously was covalently bonded to M.

Point 4: the electron in the orbital on M previously bonded to Z, now remains on the M, reducing it (becomes an $x^2$-$y^2$ orbital for the case of $V^V$ to $V^{IV}$ as in example 1).

General synthetic procedures: See example 2, "Synthetic strategies for general catalysts bearing Y=X-Z-M motifs for C—H activation".

Example 4

Figure 17:
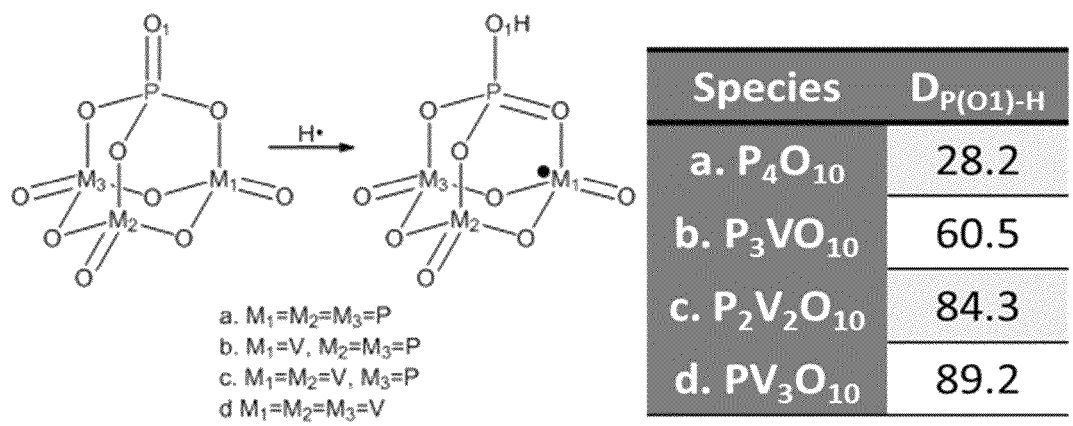
FIGS. 17(a), (b), (c) and (d) show illustration of the ROA principle.
Figure 18:
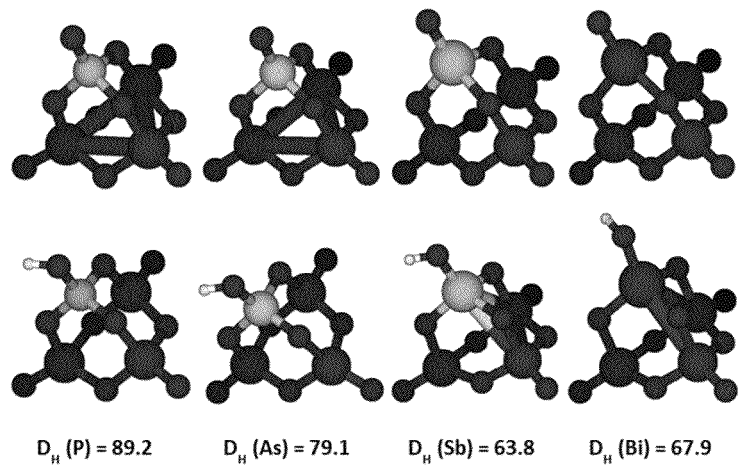
FIG. 18 shows and illustration of optimized structures of the XV3O10 species (first row) (X═P, As, Sb, Bi) and their monohydrogenated XV3O10H counterparts (second row) from activating RH. All numbers are in kcal/mol.

This is a specific case of example 3, to illustrate the mechanism described herein. The model system is as in FIG. 17. In this case, X in FIG. 16 is P in FIG. 17;
Y in FIG. 16 is $O_1$ in FIG. 17;
$Z_1$ in FIG. 16 is $O_2$ in FIG. 17;
"H" in FIG. 16 is H in FIG. 17;
M in FIG. 16 is $X_1$ in FIG. 17;
$Z_2$ and $Z_3$ in FIG. 16 are also O atoms in FIG. 17;

The additional atoms (additional O atoms as well as $X_2$ and $X_3$) in FIG. 17 represent other atoms attached to the template in FIG. 16 to provide for stability and structural support.

Consider the case in which $X_1 = X_2 = X_3 = P$.

It can be seen from FIG. 17 that this leads to $D(P=O_1)=28.2$ kcal/mol. Thus, if the bond energy of the H—R bond is $D(H—R)=100$ kcal/mol, the activation energy for activating RH is $E_{act}(R—H) > 100-28.2 = 71.8$ kcal/mol.

This is consistent with normal expectations that P=O bonds are very unreactive.

Now consider the case in which $X_1 = X_2 = X_3 = V$.

It can be seen from FIG. 17 that this leads to $D(P=O_1)=89.2$ kcal/mol

Thus if the bond energy of the H—R bond is $D(H—R)=100$ kcal/mol, the activation energy for activating RH is $E_{act}(R—H) > 100-89.2 = 10.8$ kcal/mol.

With such a low barrier this reaction would be rapid even at temperatures well below room temperature.

This is a completely unexpected result. It has never before been suggested that this coupling of P=O through an O two adjacent V=O entities could so dramatically enhance the reactivity. The explanation is the ROA principle discussed above.

Now consider the intermediate case of $X_1=X_2=V$ and $X_3=P$.

Figure 14:
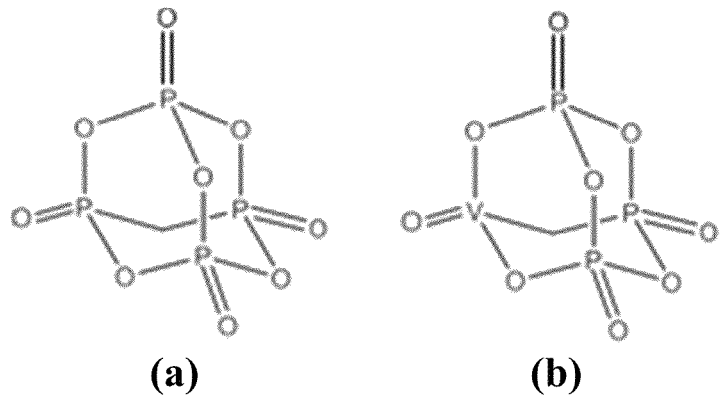
FIGS. 14(a) and (b) show alternative substitution patterns of models described herein.

It is seen In FIG. 14 that this case is also very reactive with $D(P=01)=84.3$ kcal/mol.

Thus if the bond energy of the H—R bond is $D(H—R)=100$ kcal/mol, the activation energy for activating RH is $E_{act}(R—H) > 100-84.3 = 15.7$ kcal/mol.

With such a low barrier this reaction would also be rapid at room temperature.

As indicated above, this is a completely unexpected result. It has never before been suggested that this coupling of P=O through an O to adjacent V=O entities could so dramatically enhance the reactivity. The explanation is the ROA principle discussed above.

This example also illustrates that the ROA principle can be used to titrate or adjust the activity of the P=O bond. This might be useful to avoid activating the products of the reaction or activating a different substrate also in the reaction mixture.

See example 2, "Synthetic strategies for general catalysts bearing Y=X-Z-M motifs for C—H activation", and example 3, "Computational methods", for synthetic and computational procedures, respectively.

Example 5

Figure 15:
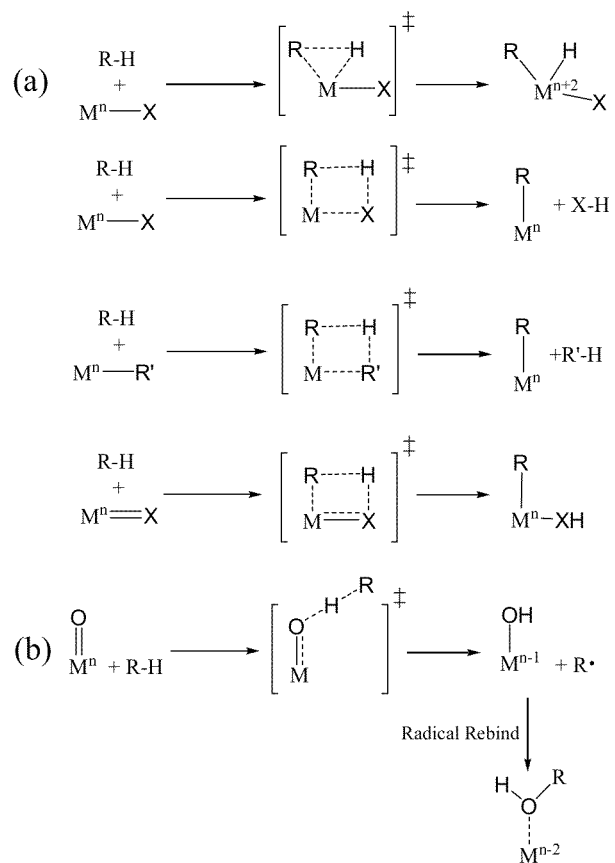
FIGS. 15(a) and (b) show existing approaches for activating alkane C—H bonds.

This is another specific case of example 3, to illustrate the ROA mechanism. The model system is as in FIG. 17. In this case, X in FIGS. 16 and 15 is P, As, Sb, or Bi;
Y in FIG. 16 is O1 in FIG. 17;
$Z_1$ in FIG. 16 is $O_2$ in FIG. 17;
"H" in FIG. 16 is H in FIG. 17;
M in FIG. 16 is V in FIG. 17
$Z_2$ and $Z_3$ in FIG. 16 are also O atoms in FIG. 17;

The additional atoms (additional O and V) in FIG. 17 represent other atoms attached to the template in FIG. 16 to provide for stability and structural support.

It can be seen that this leads to:
$D(P=O1)=89.2$ kcal/mol, as discussed above;
$D(As=O1)=79.1$ kcal/mol. Thus if the bond energy of the H—R bond is $D(H—R)=100$ kcal/mol, the activation energy for activating RH is $E_{act}(R—H) > 100-79.1 = 21.9$ kcal/mol
$D(Sb=O1)=63.8$ kcal/mol. Thus if the bond energy of the H—R bond is $D(H—R)=100$ kcal/mol, the activation energy for activating RH is $E_{act}(R—H) > 100-63.8 = 36.2$ kcal/mol
$D(Bi=O1)=67.9$ kcal/mol. Thus if the bond energy of the H—R bond is $D(H—R)=100$ kcal/mol, the activation energy for activating RH is $E_{act}(R—H) > 100-67.9 = 32.1$ kcal/mol Here the cases of X=Sb or Bi may not be effective in activating propane where $D(H-iPr) \sim 100$ kcal/mol; however they are expected to be just right for activating propene where $D(R—H) \sim 88$ kcal/mol, leading to $E_{act}(R—H) > 24.2$ and 20.1, respectively. Note in particular that Bi is better than Sb.

This is a completely unexpected result. It has never before been suggested that this coupling of P=O, As=O, Sb=O, or Bi=O through an O to adjacent V=O entities could so dramatically enhance the reactivity. The explanation is the ROA principle discussed above.

Indeed the most effective catalysts for selective oxidation of propene to acrolein or selective ammoxidation of propene to acrylonitrile are based on MoBiOx and variations. It is possible that this catalyst makes use of the ROA principle.

Although X=As is not as reactive as X=P, the activation energy is still suitable for reactions at room temperature and just above, and such systems can be preferred to X=P because they are less likely to reactive with intermediates and products that might lead to further oxidation (toward CO or $CO_2$).

See example 2, "Synthetic strategies for general catalysts bearing Y=X-Z-M motifs for C—H activation", and example 3, "Computational methods", for synthetic and computational procedures, respectively.

Example 6

Figure 19:
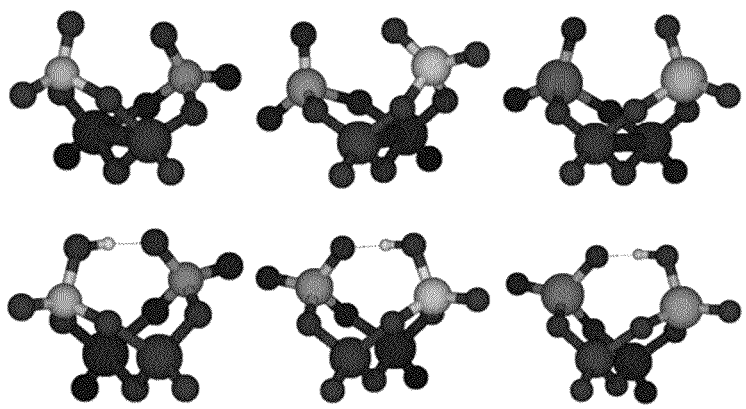
FIG. 19 shows an illustration of optimized structures of the Z2V2O11 species (first row) (Z═S, Se, Te) and their monohydrogenated Z2V2O11H counterparts (second row). All numbers are in kcal/mol.
Figure 20:
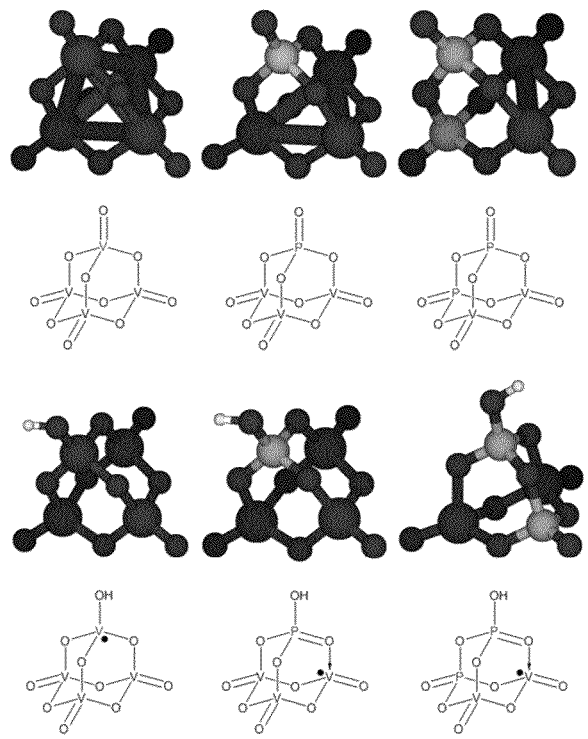
FIG. 20 shows an illustration of optimized structures of the initial species (first 2 rows) and their monohydrogenated counterparts (last 2 rows).
Figure 21:
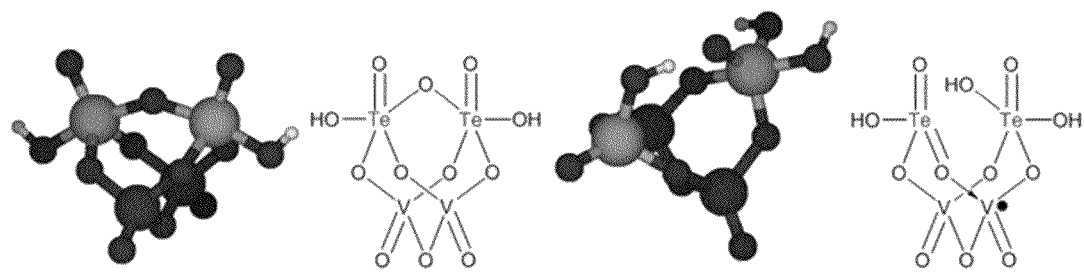
FIG. 21 shows optimized structures of the hydrated species Te2V2O12H2 and Te2V2O12H3, along with their schematic representations. Mulliken spin density was used to assign radical character. DH=92.0 kcal/mol.
Figure 22:
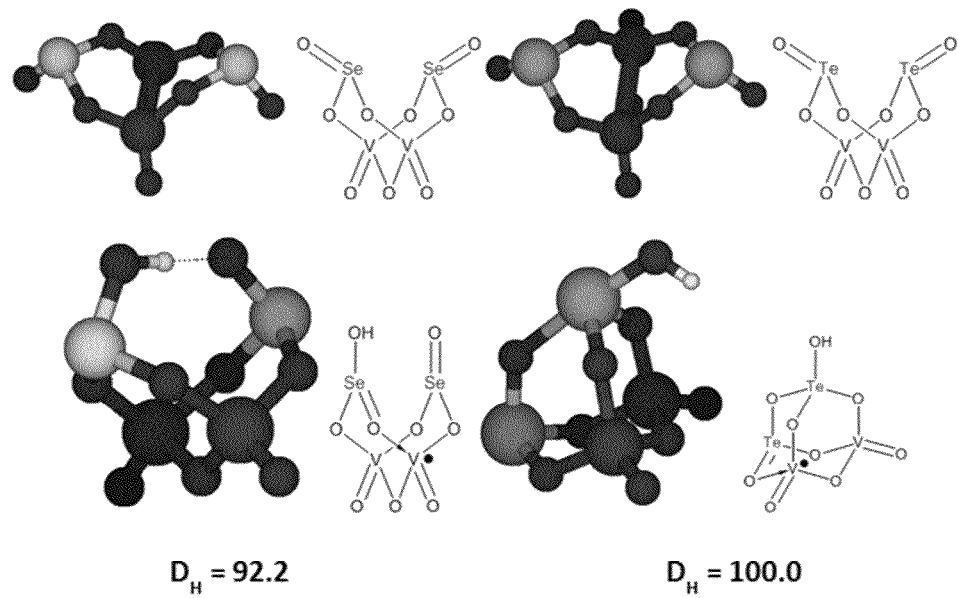
FIG. 22 shows optimized structures of Se2V2O9 and Te2V2O9 and their schematic representations (first row); optimized structures of the monohydrogenated Se2V2O9H and Te2V2O9H (second row). Mulliken spin density was used to assign radical character. All numbers are in kcal/mol.

This is another specific case of example 3, to illustrate the ROA mechanism. The model system is as in FIG. 17. In this case, X in FIG. 16 is S, Se, Te, or Po in FIG. 19;
Y in FIG. 16 is $O_1$ in FIG. 17;
$Z_1$ in FIG. 16 is $O_2$ in FIG. 17;
"H" in FIG. 16 is H in FIG. 17;
M in FIG. 16 is V in FIG. 17;
$Z_2$ and $Z_3$ in FIG. 16 are also O atoms in FIG. 17;

The additional O atoms in FIG. 17 represent other atoms attached to the template in FIG. 16 to provide for stability and structural support.

It is seen that this leads to:
$D(S=O1)=90.7$ kcal/mol,
$D(Se=O1)=90.0$ kcal/mol,
$D(Te=O1)=94.5$ kcal/mol.

Although Po=O would be favorable, the exact value was not calculated since Po is radioactive and not likely of much interest for catalysis.

Here, all 3 cases of X=S, Se, Te would be expected to be effective in activating propane leading to $E_{act}(R—H) > 9.3$, 10.0, 5.5. Indeed, they could be suitable for attacking much stronger bonds such as in benzene [$D(RH)=107$ kcal/mol], ethene [($D(RH)=118$) kcal/mol], and ethyne [$D(RH)=128$ kcal/mol].

This is a completely unexpected result. It has never before been suggested that this coupling of S=O, Se=O, or Te=O through an O to adjacent V=O entities could so dramatically enhance the reactivity. The explanation is the ROA principle discussed above.

In fact, catalysts for selective oxidation of propene to acrolein or selective ammoxidation of propene to acrylonitrile often involve Se or Te. It is possible that such catalysts may make use of the ROA principle.

See example 2 section 1 and example 3 section 2 for synthetic and computational procedures, respectively.

Example 7

This is another specific case of example 3, to illustrate the ROA mechanism. The model system is as in FIG. 17. In this case, X in FIG. 16 is Te in FIG. 17;
Y, $Z_1$, $Z_2$ and $Z_3$ in FIG. 13 are O atoms in FIG. 17;
"H" in FIG. 16 is H in FIG. 17;
M in FIG. 16 is V in FIG. 17;

The additional O atoms in FIG. 17 represent other atoms attached to the template in FIG. 16 to provide for stability and structural support.

It is seen that this leads to:

D(Te=O1)=92.0 kcal/mol. Which would be expected to be effective in activating propane leading to $E_{act}$(R—H)>8.0 kcal/mol. Indeed this could be suitable for attacking much stronger bonds such as in benzene [D(RH)=107 kcal/mol], ethene [(D(RH=118) kcal/mol], and ethyne [D(RH)=128 kcal/mol].

This is a completely unexpected result. It has never before been suggested that this coupling of Te=O through an O to adjacent V=O entities could so dramatically enhance the reactivity. The explanation is the ROA principle discussed above. Similar results are expected for S and Se in place of Te.

See example 2, "Synthetic strategies for general catalysts bearing Y=X-Z-M motifs for C—H activation", and example 3, "Computational methods", for synthetic and computational procedures, respectively.

Example 8

This is another specific case of example 3, to illustrate the ROA mechanism. The model system is as in FIG. 17. In this case, X in FIG. 16 is Se or Te in FIG. 17;
Y, $Z_1$, $Z_2$ and $Z_3$ in FIG. 16 are O atoms in FIG. 17;
"H" in FIG. 16 is H in FIG. 17;
M in FIG. 16 is V in FIG. 17;

The additional O atoms in FIG. 17 represent other atoms attached to the template in FIG. 16 to provide for stability and structural support.

It can be seen that this leads to:

D(Se=O1)=92.2 kcal/mol and D(Te=O1)=100.0 kcal/mol. Which would be effective in activating propane leading to $E_{act}$(R—H)>7.8 and O kcal/mol, respectively. Indeed, this could be suitable for attacking much stronger bonds such as in benzene [D(RH)=107 kcal/mol], ethene [(D(RH=118) kcal/mol], and ethyne [D(RH)=128 kcal/mol].

This is a completely unexpected result. It has never before been suggested that this coupling of Se=O or Te=O through an O to adjacent V=O entities could so dramatically enhance the reactivity. The explanation is the ROA principle discussed above. Similar results are expected for S in place of Te Comparing examples 6-8, it can be seen that the ROA principle applies to S, Se, and Te in both the IV and VI oxidation states.

See example 2, "Synthetic strategies for general catalysts bearing Y=X-Z-M motifs for C—H activation", and example 3, "Computational methods", for synthetic and computational procedures, respectively.

New Example 9

Figure 23:
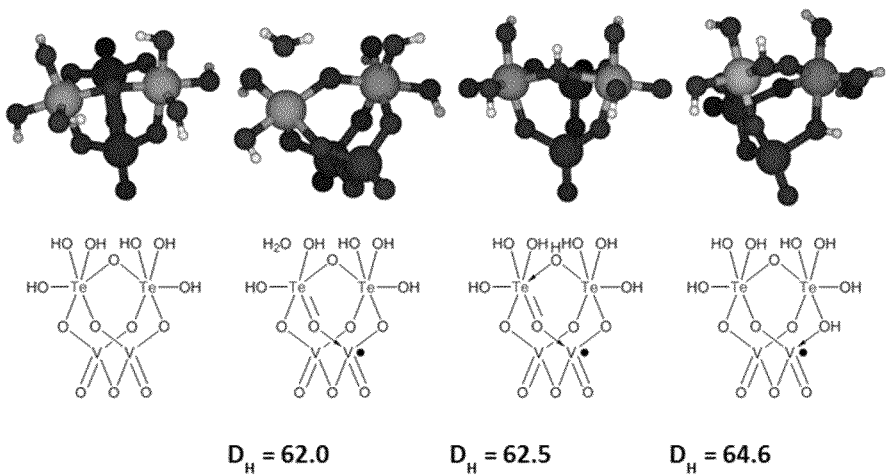
FIG. 23 shows optimized structures of the fully hydrated species Te2V2O14H6 (left) and the three products Te2V2O14H7 (right 3 cases), along with their schematic representations (second row). Mulliken spin density was used to assign radical character. All numbers are in kcal/mol.

For another illustration of the ROA mechanism, consider the model system in FIG. 23. In this case, X in FIG. 16 is Te in FIG. 17;
$Z_1$, $Z_2$ and $Z_3$ in FIG. 16 are O atoms in FIG. 17;
"H" in FIG. 16 is H in FIG. 17;
M in FIG. 16 is V in FIG. 17;

The additional O atoms in FIG. 17 represent other atoms attached to the template in FIG. 13 to provide for stability and structural support.

In this case the Te(VI) is fully hydrated, with no oxo bond (no Y). It can be seen that this fully hydrated species is much less effective at activating RH, leading to barriers of 38.0, 37.5, and 33.4 kcal/mol, respectively This shows the importance of having an oxo bond for the ROA principle.

See example 3, "Computational methods", for computational procedures.

Example 10

Figure 24:
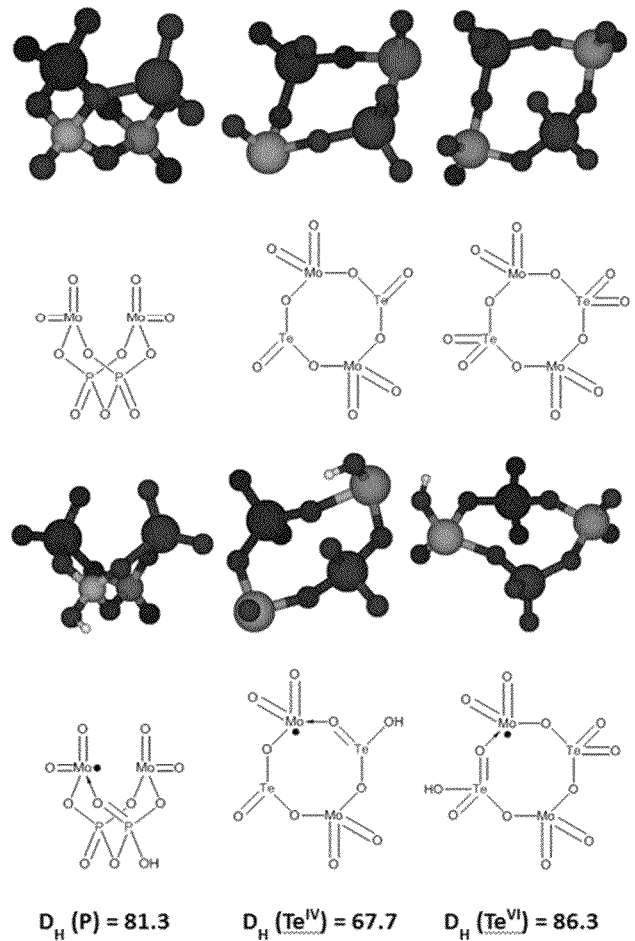
FIG. 24 shows optimized structures of the molybdenum-containing species $P_2Mo_2O_{11}$, $Te_2Mo_2O_{10}$, and $Te_2Mo_2O_{12}$ (first row), along with their schematic representations (second row); optimized structures of the corresponding monohydrogenated species (third row) and their schematic representations (fourth row). Mulliken spin density was used to assign radical character. All numbers are in kcal/mol.

For another illustration of the ROA mechanism, consider the model system in FIG. 24. In this example it is illustrated that the ROA principle applies equally to cases in which the V in oxidation state V is replaced with Mo in oxidation state VI. In this case, X in FIG. 16 is P or Te in FIG. 17;
Y, $Z_1$, $Z_2$ and $Z_3$ in FIG. 16 are O atoms in FIG. 17;
"H" in FIG. 16 is H in FIG. 17;
M in FIG. 16 is Mo in FIG. 17;

The additional O atoms in FIG. 17 represent other atoms attached to the template in FIG. 16 to provide for stability and structural support.

In this example that the ROA principle applies equally to cases in which the V in oxidation state V is replaced with Mo in oxidation state VI is illustrated.

The D(P=O1)=81.3 can be compared with 84.3 in example 4, the in the case where $X_1$=$X_2$=V and $X_3$=P.

The D(Te=O)=67.7 for Te in the IV oxidation state can be compared with D(Te=O) in example 7, where replacing V with Mo led to a geometry in which the bridging O between the Te is not favorable.

The D(Te=O)=86.3 for Te in the VI oxidation state can be compared with D(Te=O)=92.0 in example 7.

See example 2, "Synthetic strategies for general catalysts bearing Y=X-Z-M motifs for C—H activation", and example 3, "Computational methods", for synthetic and computational procedures, respectively.

Example 11

Figure 48:
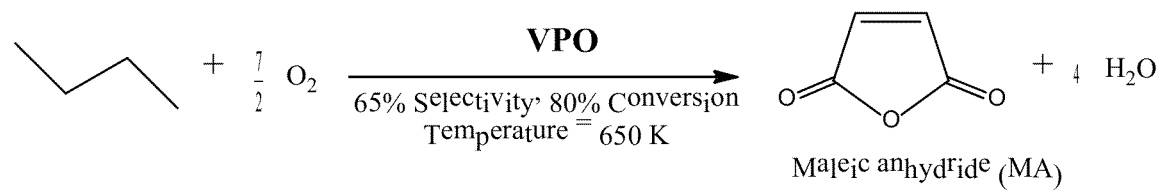
FIG. 48 shows a chemical equation for the oxidation of n-butane to maleic anhydride by VPO catalyst.

Application of the Reduction-Coupled Oxo Activation (ROA) Principle for Selective Oxidation to Complex Products: Investigation of V=O Moieties as the Activation Center in VPO Catalyst In example 1 above it was shown how catalysts provided with the methods herein described can be used to provide catalysts to activate very stable substrates. In this section it is shown how to use the methods herein described can be used to provide catalysts for a much more complex reaction, selective oxidation of butane to maleic anhydride, as in FIG. 48.

Indeed, the VOPO catalyst is well known to carry out this reaction, but the mechanism by which it works was unknown. It is found that the ROA principle explains all observed properties of this catalyst, providing now a basis to use the methods herein described to develop improved catalysts.

the Reduced Structure, $(VO)P_2O_7$

Figure 49:
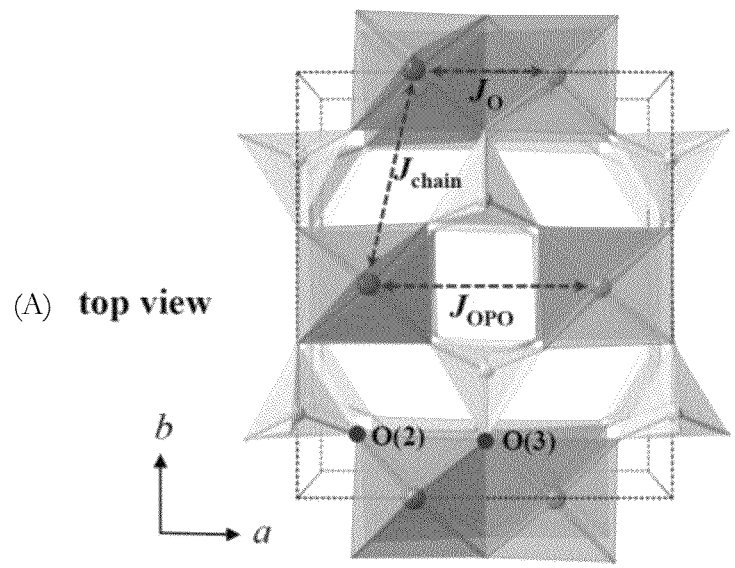
FIG. 49 shows a schematic representation of the top (FIG. 49A) and side (FIG. 49B) view of high pressure, high symmetry form of $(VO)_2P_2O_7$. Each V is in the IV oxidation state with a single unpaired d orbital. The 4 different types of spin coupling interactions between these d orbitals are indicated. The $J_{OPO}$ along the chain but across the 8 membered ring is the strongest (antiferromagnetic). The $J_O$ along the chain but across the 4 membered ring is weakly antiferromagnetic at the equilibrium geometry, but becomes weakly ferromagnetic upon compression by 5%. The interchain and interlayer couplings are very weak and ferromagnetic.
Figure 49:
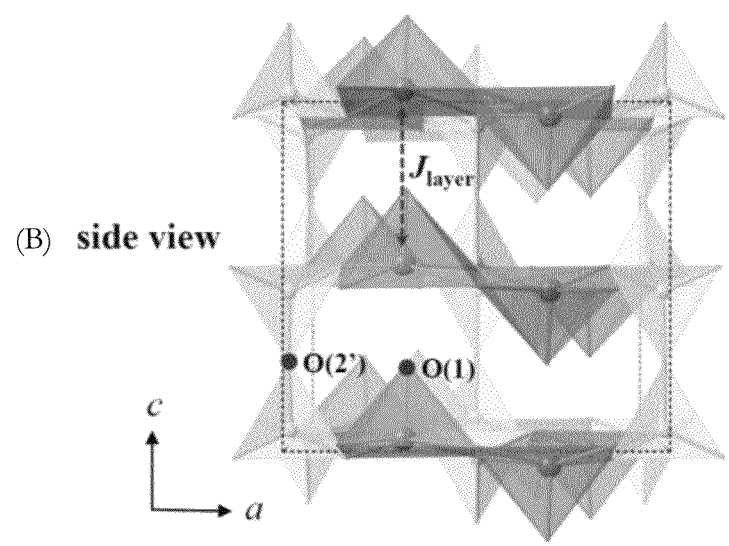
Figure 50:
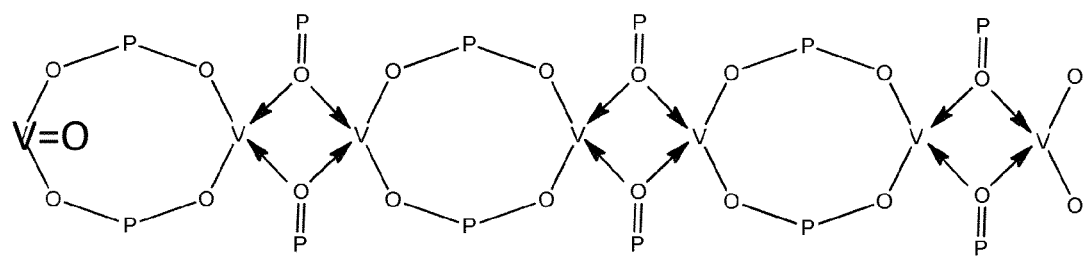
FIG. 50 shows schematic representation of the valence bond description of the $(VO)_2P_2O_7$ crystal. Note that each P shown here also has 3P—O single bonds that bridge to neighboring V atoms. Thus, the bond of the P═O oxygen with the V in the 4-membered ring is a dative donor-acceptor bond, leaving this unit very flexible. Each V shown here has also a V═O bond out of the plane, leading to a IV oxidation state with a singly occupied d orbital remaining on the V.

The starting structure for the $(VO)P_2O_7$ catalysts has been well characterized. As shown in FIG. 49 and FIG. 50, it has chains of V sites connected by O atoms shared with phosphates, plus a vanadium oxo bond, V=O, perpendicular to the sheet. This V has oxidation state +4, so that there is a $d_{xy}$ singly occupied orbital on each V, which is antiferromagnetically couple to its neighbors.

Figure 25:
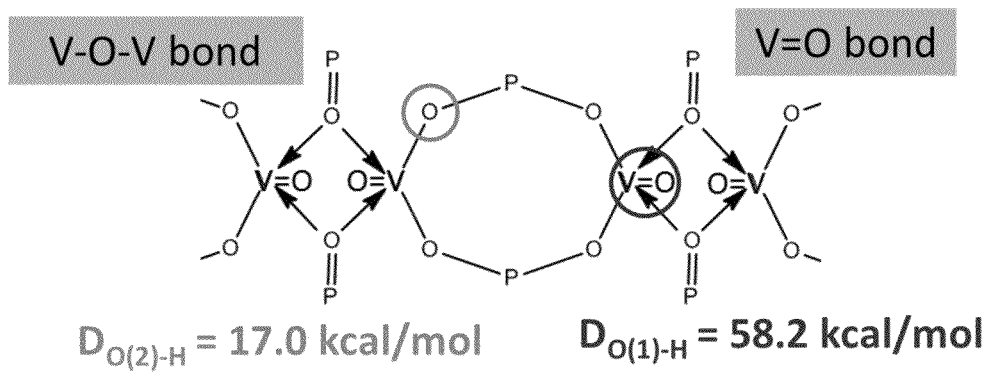
FIG. 25 shows O—H bond strength for oxygen atoms on the $(VO)_2P_2O_7$ surface bonded to V.

As shown in FIG. 25, the bond energy to the O(1)=V (vanadyl) group is calculated to be $D_{O(1)-H}$=58.2 kcal/mol, so that the activation energy is expected to be ~47 kcal/mol, far too high to explain the experiments. The 0 bridging between V and P was also examined, which was found to lead to $D_{O(2)-H}$=17 kcal/mol, extremely inactive as expected Thus it can be concluded that neither the V=O bond or the V—O—P bond of the reduced structure, $(VO)P_2O_7$, can be responsible for activating butane.

These results indicate clearly that neither oxygen on the VOPO surface is the active site for initial n-butane C—H activation. From experimental studies of the same oxidation reaction catalyzed on supported vanadia, Wachs et al. reached the same conclusion. Thus it was conclude that the reduced form of the VPO catalyst is not the active catalyst.

the Oxidized Surface $VOPO_4$

Figure 26:
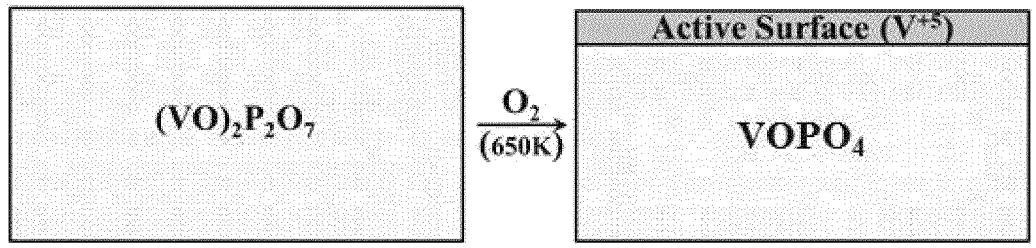
FIG. 26 shows oxidation of $(VO)_2P_2O_7$ leads to the formation of VOPO$_4$ on the surface layers.

Experiments show that the surface of the working VPO catalyst contains small amounts of various phases of $VOPO_4$ as in FIG. 26 This opens a possibility that $V^{+5}$, which is known to activate alkanes and furan, may form in layers at the surface of $VOPO_4$. There are five known phases of $VOPO_4$, with calculated energies as in FIG. 27.

Figure 28:
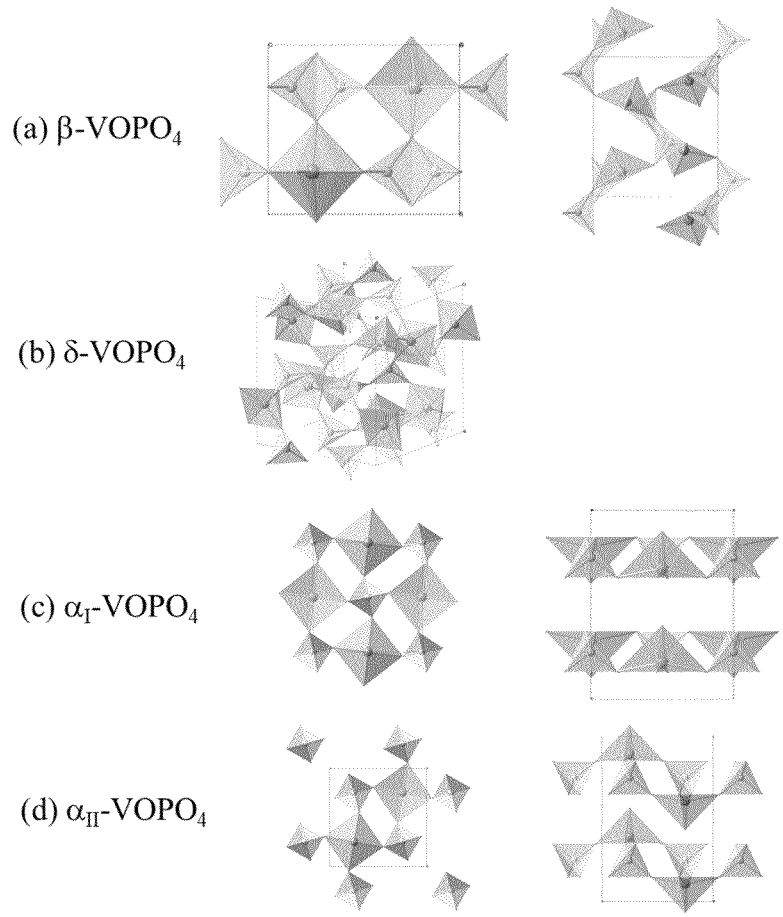

Comparing the structures of these well-defined $VOPO_4$ structures ($\alpha_I$, $\alpha_{II}$, $\delta$, and $\beta$ phases) to VOPO, no significant structural change at the V atoms is seen. Instead, the major changes are at phosphorus (FIG. 28). In VOPO, each phosphorus atom forms one O—P bond (the pyrophosphate P—O—P bond that links two adjacent layers) and three O—V bonds, whereas in these four cases of $VOPO_4$ phosphorus binds with four O—V motifs.

Figure 29:
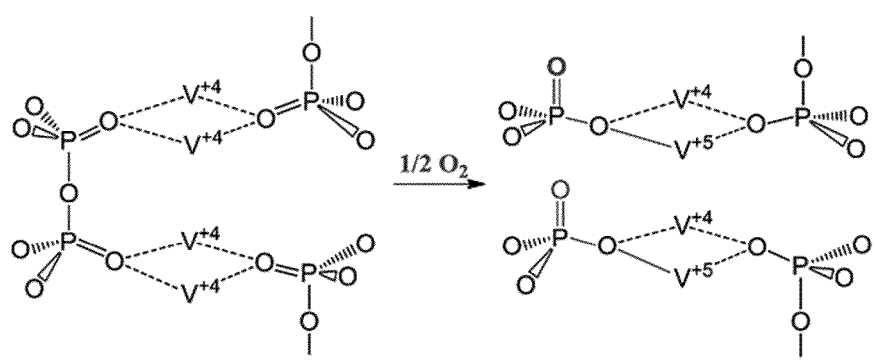
FIG. 29 shows valence bond description of pyrophosphate oxidation to phosphate.

This suggests that the oxidation of VOPO to $VOPO_4$ may occur by adding oxygen to phosphorus, converting one pyrophosphate into two ortho-phosphates (FIG. 29). In this way, two of the dative bonds in the V—(O)$_2$—V motif of VOPO become covalent, and concurrently, two $V^{+4}$ are oxidized to $V^{+5}$. This increase in the oxidation state for vanadium may enhance the reactivity of the surface oxygen toward n-butane C—H activation.

Figure 27:
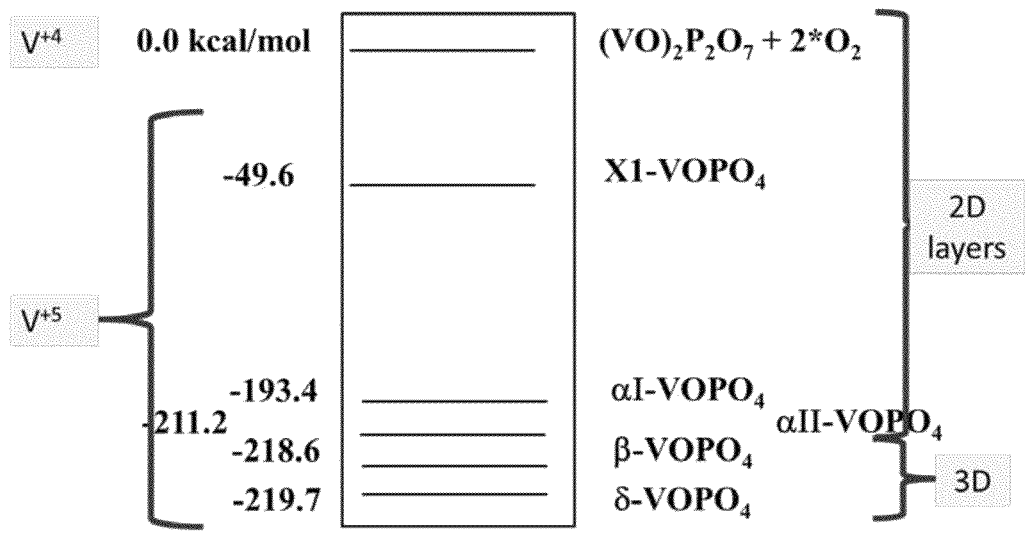
FIG. 27 shows phase stability (kcal/mol) of various phases of VOPO4 (referenced to (VO)2P2P7+O2). From PBE DFT calculations FIGS. 28(a), (b), (c) and (d) show 3D structures for β-, δ-, $\alpha_I$-, and $\alpha_{II}$-VOPO$_4$.

In order to verify this hypothesis, bulk $VOPO_4$ and the corresponding surfaces were studied (see tables 4-22). The cell parameters and atomic positions of these $VOPO_4$ phases were first optimized under orthorhombic symmetry. The relative energies of these phases are shown in FIG. 27 (from PBE DFT calculations).

TABLE 4

Coordinates (fractional) and Energies (Hartree)
$(VO)_2P_2O_7$ bulk
a = 8.445 Å; b = 9.661 Å; c = 7.624 Å
E = −1206.793002 hartree

| | | | |
|---|---|---|---|
| V | 0.309641239 | −0.002742885 | 0.036692923 |
| V | −0.190323969 | −0.497070037 | −0.036455426 |

TABLE 4-continued

Coordinates (fractional) and Energies (Hartree)
$(VO)_2P_2O_7$ bulk
a = 8.445 Å; b = 9.661 Å; c = 7.624 Å
E = −1206.793002 hartree

| | | | |
|---|---|---|---|
| V | 0.189537828 | −0.497309982 | −0.463833018 |
| V | −0.309794141 | −0.002943949 | 0.463231761 |
| V | −0.30969621 | 0.002762114 | −0.036693227 |
| V | 0.190312419 | 0.497083984 | 0.036376701 |
| V | −0.189552348 | 0.497292806 | 0.463783752 |
| V | 0.309860779 | 0.002933927 | −0.463162836 |
| P | −0.002237998 | −0.201920684 | 0.044216548 |
| P | −0.502299119 | −0.297930837 | −0.044204631 |
| P | 0.502165281 | −0.298169336 | −0.455718052 |
| P | 0.00237041 | −0.201528336 | 0.45550302 |
| P | 0.002154879 | 0.201929183 | −0.044224397 |
| P | 0.502262538 | 0.29793606 | 0.044220653 |
| P | −0.502133692 | 0.298148703 | 0.455728959 |
| P | −0.002298121 | 0.201532507 | −0.455509649 |
| O | −0.318399086 | −0.0254525 | 0.251723295 |
| O | 0.181236961 | −0.47481193 | −0.252291418 |
| O | −0.181829727 | −0.474353884 | −0.247886806 |
| O | 0.318251996 | −0.025200301 | 0.24818037 |
| O | 0.318370241 | 0.025413785 | −0.251648908 |
| O | −0.181310901 | 0.474765466 | 0.252304202 |
| O | 0.181736839 | 0.474373319 | 0.2478437 |
| O | −0.318303954 | 0.025233513 | −0.248176998 |
| O | 0.0000131 | −0.169456345 | 0.249827915 |
| O | −0.499651023 | −0.329798238 | −0.249909719 |
| O | −0.000122543 | 0.169460577 | −0.249832398 |
| O | −0.500320599 | 0.32977995 | 0.249923267 |
| O | −0.156157516 | −0.147163514 | −0.031463135 |
| O | 0.343663577 | −0.352901083 | 0.030823871 |
| O | −0.343993608 | −0.353399748 | 0.468844181 |
| O | 0.156373028 | −0.146805467 | −0.468975262 |
| O | 0.156131604 | 0.147196302 | 0.031458582 |
| O | −0.34362449 | 0.352886272 | −0.030835471 |
| O | 0.344074888 | 0.353493568 | −0.468823713 |
| O | −0.156214136 | 0.146715581 | 0.468825711 |
| O | −0.145754844 | −0.135295116 | −0.468172209 |
| O | 0.353747966 | −0.364536066 | 0.468485484 |
| O | −0.35430649 | −0.364495695 | 0.032231639 |
| O | 0.145857548 | −0.135473496 | −0.032057409 |
| O | 0.145925868 | 0.135415175 | 0.468281012 |
| O | −0.35367361 | 0.364438311 | −0.468481909 |
| O | 0.35434089 | 0.364502493 | −0.032217914 |
| O | −0.145879016 | 0.135457299 | 0.032082162 |
| O | −0.500084778 | −0.136171808 | −0.021229322 |
| O | 0.000042156 | −0.363724671 | 0.021648203 |
| O | 0.000194462 | −0.363180364 | 0.478065413 |
| O | 0.500005548 | −0.136384491 | −0.478752656 |
| O | 0.500051266 | 0.136173047 | 0.021253946 |
| O | −0.000113234 | 0.363737575 | −0.021690567 |
| O | −0.000167727 | 0.363192859 | −0.478095206 |
| O | −0.500080433 | 0.136366389 | 0.478784987 |

TABLE 5

$(VO)_2P_2O_7$ Surface
a = 8.362 Å; b = 9.536 Å; c = 19.994 Å
E(SCF) = −1241.25144541 hartree

| | | | |
|---|---|---|---|
| V | 0.305808114 | 0.011586039 | 0.403941808 |
| V | 0.18792653 | −0.496873926 | 0.598448283 |
| V | −0.307583601 | 0.010837797 | 0.634883364 |
| V | −0.189739445 | −0.495933378 | 0.439376462 |
| V | −0.311614839 | 0.003958437 | 0.439645815 |
| V | −0.19434411 | −0.489227697 | 0.634946086 |
| V | 0.309903605 | 0.003448509 | 0.598841681 |
| V | 0.192595121 | −0.488601481 | 0.402918945 |
| P | −0.008276904 | 0.209222092 | 0.392462452 |
| P | −0.496508973 | 0.302541651 | 0.598299499 |
| P | 0.006446869 | 0.208603989 | 0.646357717 |
| P | 0.494759037 | 0.303159619 | 0.439386603 |
| P | 0.003522296 | −0.197156947 | 0.439534049 |
| P | 0.491301275 | −0.291563057 | 0.645879824 |
| P | −0.005656955 | −0.197848919 | 0.598526756 |

TABLE 5-continued (VO)$_2$P$_2$O$_7$ Surface
a = 8.362 Å; b = 9.536 Å; c = 19.994 Å
E(SCF) = −1241.25144541 hartree

| | | | |
|---|---|---|---|
| P | −0.493316933 | −0.290465472 | 0.392287863 |
| O | −0.298440967 | 0.043714009 | 0.71365294 |
| O | −0.17560073 | 0.153794105 | 0.409693353 |
| O | −0.127488022 | 0.135394467 | 0.607664405 |
| O | −0.498368141 | 0.140056388 | 0.426730969 |
| O | −0.189189456 | 0.492153204 | 0.519767169 |
| O | −0.337357088 | 0.351688177 | 0.625723447 |
| O | −0.359965542 | 0.377790599 | 0.411094995 |
| O | 0.009070498 | 0.373437464 | 0.630111401 |
| O | 0.295779927 | 0.044684407 | 0.325203613 |
| O | 0.17375069 | 0.152755318 | 0.629365092 |
| O | 0.125639699 | 0.136646557 | 0.431443566 |
| O | 0.49696885 | 0.13952192 | 0.611319934 |
| O | 0.187182473 | 0.491267111 | 0.518042489 |
| O | 0.335851596 | 0.352191765 | 0.411692673 |
| O | 0.358222263 | 0.376983019 | 0.626776981 |
| O | −0.010877472 | 0.374413517 | 0.407967886 |
| O | 0.310233623 | −0.007927181 | 0.518409355 |
| O | 0.162886375 | −0.147590973 | 0.412578965 |
| O | 0.139739723 | −0.123196524 | 0.626715683 |
| O | −0.490945051 | −0.125658822 | 0.408577272 |
| O | 0.202454676 | −0.455925615 | 0.324160617 |
| O | 0.324369367 | −0.347049216 | 0.628141203 |
| O | 0.372363446 | −0.363981096 | 0.430587973 |
| O | 0.001149568 | −0.360796891 | 0.611757279 |
| O | −0.311804792 | −0.00835649 | 0.520030119 |
| O | −0.164448475 | −0.1484094 | 0.626223844 |
| O | −0.141394642 | −0.122178079 | 0.411122862 |
| O | 0.488923634 | −0.126462635 | 0.630061807 |
| O | −0.204459054 | −0.457129997 | 0.713754925 |
| O | −0.326167115 | −0.3461895 | 0.409472527 |
| O | −0.373985283 | −0.36432286 | 0.6074866 |
| O | −0.002902966 | −0.359992513 | 0.426109086 |
| O | −0.021772981 | 0.1975834 | 0.724521962 |
| O | 0.019809716 | 0.196979039 | 0.314333004 |
| O | −0.501286446 | 0.324523915 | 0.518881812 |
| O | −0.001975584 | −0.177051154 | 0.519066359 |
| O | −0.482025059 | −0.303480622 | 0.724123756 |
| O | 0.479314999 | −0.300974321 | 0.314027723 |
| H | −0.381823716 | −0.355726554 | 0.734782842 |
| H | 0.379421699 | −0.353504123 | 0.303242411 |
| H | −0.122018219 | 0.145159709 | 0.734956293 |
| H | 0.120427617 | 0.144789288 | 0.30409319 |

TABLE 6

Hydrogen binds with O(1) = V on (VO)$_2$P$_2$O$_7$ Surface
a = 8.362 Å; b = 9.536 Å; c = 19.994 Å
E(SCF) = −1241.843136 hartree

| | | | |
|---|---|---|---|
| V | 0.30309005 | 0.011853914 | 0.401544547 |
| V | 0.189473357 | 0.503866802 | 0.596603044 |
| V | 0.691178967 | 0.009562338 | 0.63338827 |
| V | 0.806963536 | 0.504726449 | 0.437601931 |
| V | 0.685157814 | 0.004127305 | 0.438288642 |
| V | 0.803577904 | 0.508872552 | 0.618134933 |
| V | 0.308167342 | 0.002302816 | 0.597978143 |
| V | 0.189179607 | 0.512402217 | 0.402236004 |
| P | 0.989697361 | 0.209875517 | 0.39208953 |
| P | 0.500306307 | 0.300110458 | 0.595872432 |
| P | 0.004714267 | 0.210197563 | 0.645037379 |
| P | 0.49165895 | 0.302961226 | 0.436895106 |
| P | −0.000098333 | 0.80476481 | 0.437712086 |
| P | 0.492167907 | 0.707601744 | 0.644442089 |
| P | 0.99334898 | 0.803121175 | 0.595952551 |
| P | 0.502389611 | 0.710339572 | 0.390776987 |
| O | 0.701705645 | 0.043706358 | 0.712084157 |
| O | 0.823345079 | 0.15451894 | 0.410711847 |
| O | 0.872424937 | 0.134779936 | 0.606155353 |
| O | 0.499078436 | 0.140076092 | 0.423692983 |
| O | 0.809280686 | 0.489641953 | 0.519747679 |
| O | 0.659861182 | 0.350557793 | 0.62237658 |
| O | 0.637986914 | 0.377703371 | 0.409594839 |

TABLE 6-continued

Hydrogen binds with O(1) = V on (VO)$_2$P$_2$O$_7$ Surface
a = 8.362 Å; b = 9.536 Å; c = 19.994 Å
E(SCF) = −1241.843136 hartree

| | | | |
|---|---|---|---|
| O | 0.012260015 | 0.373032407 | 0.626825292 |
| O | 0.292219204 | 0.04469112 | 0.322812717 |
| O | 0.171619376 | 0.148607561 | 0.632535281 |
| O | 0.125409637 | 0.137361557 | 0.429995858 |
| O | 0.49515002 | 0.13788679 | 0.609965879 |
| O | 0.190975168 | 0.491704369 | 0.51608377 |
| O | 0.334079528 | 0.353391198 | 0.408560777 |
| O | 0.355480814 | 0.37409718 | 0.624839664 |
| O | 0.987881427 | 0.374834782 | 0.407558763 |
| O | 0.307245401 | 0.99283673 | 0.517435504 |
| O | 0.158548946 | 0.853344713 | 0.409537354 |
| O | 0.139112852 | 0.874929878 | 0.625101278 |
| O | 0.505503451 | 0.875132083 | 0.406864519 |
| O | 0.196066564 | 0.547471034 | 0.323573405 |
| O | 0.322703609 | 0.651120077 | 0.63029716 |
| O | 0.368085547 | 0.637835245 | 0.429449638 |
| O | 0.001632596 | 0.639793662 | 0.606163246 |
| O | 0.684086956 | 0.99092868 | 0.518645491 |
| O | 0.83462762 | 0.85062359 | 0.624615835 |
| O | 0.854092536 | 0.877893384 | 0.40871458 |
| O | 0.486175296 | 0.873825485 | 0.629548799 |
| O | 0.791371883 | 0.545971614 | 0.709902603 |
| O | 0.669220804 | 0.653892259 | 0.407888165 |
| O | 0.619444415 | 0.63826333 | 0.600764493 |
| O | 0.993460065 | 0.641165727 | 0.426476421 |
| O | 0.965887162 | 0.20931127 | 0.723052323 |
| O | 0.01442323 | 0.197177889 | 0.313750372 |
| O | 0.493447276 | 0.321544483 | 0.516498236 |
| O | 0.99550165 | 0.830900226 | 0.51679284 |
| O | 0.533235206 | 0.692577219 | 0.720813742 |
| O | 0.474229278 | 0.699323086 | 0.312594139 |
| H | 0.637227848 | 0.635613724 | 0.726249612 |
| H | 0.372462615 | 0.64913896 | 0.30227892 |
| H | 0.872536999 | 0.146833282 | 0.7326096 |
| H | 0.114335243 | 0.144586413 | 0.302880126 |
| H | 0.835283081 | 0.477018092 | 0.741156486 |

TABLE 7

Hydrogen binds with O(2) on (VO)$_2$P$_2$O$_7$ Surface structure (a)
a = 8.362 Å; b = 9.536 Å; c = 19.994 Å
E(SCF) = −1241.783285 hartree

| | | | |
|---|---|---|---|
| V | 0.306065902 | 0.011940403 | 0.404406462 |
| V | 0.186117461 | 0.507794404 | 0.598823638 |
| V | 0.691855767 | 0.008741701 | 0.630188143 |
| V | 0.811039082 | 0.503451053 | 0.44034539 |
| V | 0.688321679 | 0.003206455 | 0.441349047 |
| V | 0.810508382 | 0.516370466 | 0.623550751 |
| V | 0.30630889 | −0.001602584 | 0.598279113 |
| V | 0.19177998 | 0.513371291 | 0.405317622 |
| P | 0.991864992 | 0.209206937 | 0.393727808 |
| P | 0.485920122 | 0.296295769 | 0.597365623 |
| P | 0.004391261 | 0.210058945 | 0.642129079 |
| P | 0.494952966 | 0.303494829 | 0.440221575 |
| P | 0.005161728 | 0.804383442 | 0.440975823 |
| P | 0.49479701 | 0.707712636 | 0.644052602 |
| P | 0.995650309 | 0.805482139 | 0.599543568 |
| P | 0.506978803 | 0.709975175 | 0.393416728 |
| O | 0.697337199 | 0.05797623 | 0.708189932 |
| O | 0.824927658 | 0.153611557 | 0.411624803 |
| O | 0.869414113 | 0.140082334 | 0.602654548 |
| O | 0.499117331 | 0.140480346 | 0.431301356 |
| O | 0.811087347 | 0.48712178 | 0.523429437 |
| O | 0.648652632 | 0.346219352 | 0.633562003 |
| O | 0.638169777 | 0.376959127 | 0.411248287 |
| O | 0.010028028 | 0.374674442 | 0.626778934 |
| O | 0.299904718 | 0.048355784 | 0.325854133 |
| O | 0.170610219 | 0.151757869 | 0.625337602 |
| O | 0.126553333 | 0.13650345 | 0.432224856 |
| O | 0.487399679 | 0.136765981 | 0.609944506 |
| O | 0.19085541 | 0.495276421 | 0.518451007 |
| O | 0.333379831 | 0.352722387 | 0.416758112 |

TABLE 7-continued

Hydrogen binds with O(2) on (VO)$_2$P$_2$O$_7$ Surface structure (a)
a = 8.362 Å; b = 9.536 Å; c = 19.994 Å
E(SCF) = −1241.783285 hartree

| | | | |
|---|---|---|---|
| O | 0.350721315 | 0.375621504 | 0.628863977 |
| O | 0.990040632 | 0.374333188 | 0.40913615 |
| O | 0.30710038 | 0.98364853 | 0.518006663 |
| O | 0.162024991 | 0.85363211 | 0.411423735 |
| O | 0.138989564 | 0.877749812 | 0.630711489 |
| O | 0.509827956 | 0.875376619 | 0.408832858 |
| O | 0.203617554 | 0.543161615 | 0.326252175 |
| O | 0.324825666 | 0.65283807 | 0.630551346 |
| O | 0.371692918 | 0.638606904 | 0.432043341 |
| O | 0.004781261 | 0.642735838 | 0.611216025 |
| O | 0.685021136 | 0.989545501 | 0.522786692 |
| O | 0.83632318 | 0.850972268 | 0.628185716 |
| O | 0.858151542 | 0.876901724 | 0.413376984 |
| O | 0.488465304 | 0.873364167 | 0.629784543 |
| O | 0.78554963 | 0.534831877 | 0.705426987 |
| O | 0.67323351 | 0.65355745 | 0.411095226 |
| O | 0.62063198 | 0.636409353 | 0.600106741 |
| O | 0.999868305 | 0.641261974 | 0.430458193 |
| O | 0.972872249 | 0.19864802 | 0.720135594 |
| O | 0.018171429 | 0.196343181 | 0.31546122 |
| O | 0.510792824 | 0.331045323 | 0.522096299 |
| O | 1.003407353 | 0.831059703 | 0.520719745 |
| O | 0.535829676 | 0.691673704 | 0.720575699 |
| O | 0.479723969 | 0.697873823 | 0.315174266 |
| H | 0.637892816 | 0.633661072 | 0.726149781 |
| H | 0.379478022 | 0.645477175 | 0.304758131 |
| H | 0.874215112 | 0.141630195 | 0.729407136 |
| H | 0.119824727 | 0.146324901 | 0.304819677 |
| H | 0.644553387 | 0.334154282 | 0.682642123 |

TABLE 8

Hydrogen binds with O(2) on (VO)$_2$P$_2$O$_7$ Surface structure (b)
a = 8.362 Å; b = 9.536 Å; c = 19.994 Å
E(SCF) = −1241.799212 hartree

| | | | |
|---|---|---|---|
| V | 0.307692717 | 0.014016841 | 0.40529307 |
| V | 0.188534419 | 0.507302917 | 0.598887561 |
| V | 0.695921413 | 0.007760595 | 0.629417751 |
| V | 0.812379423 | 0.50598163 | 0.44057474 |
| V | 0.690709964 | 0.00657755 | 0.440637182 |
| V | 0.806829437 | 0.515321688 | 0.631981608 |
| V | 0.314225583 | −0.002391406 | 0.599695943 |
| V | 0.193562172 | 0.514967952 | 0.404359319 |
| P | 0.994804132 | 0.212186861 | 0.393941013 |
| P | 0.509854483 | 0.300434575 | 0.596160549 |
| P | −0.003372659 | 0.214558953 | 0.651648765 |
| P | 0.497562354 | 0.306690343 | 0.437904579 |
| P | 0.004528954 | 0.806224067 | 0.438577944 |
| P | 0.495276542 | 0.707863904 | 0.646997315 |
| P | 0.996622354 | 0.804172383 | 0.597634226 |
| P | 0.507361731 | 0.712317477 | 0.394754882 |
| O | 0.704058973 | 0.050717596 | 0.709190693 |
| O | 0.827930214 | 0.15724041 | 0.412133917 |
| O | 0.888467877 | 0.132553765 | 0.605271422 |
| O | 0.504358208 | 0.143458426 | 0.428749224 |
| O | 0.814974085 | 0.48832231 | 0.521888874 |
| O | 0.66156218 | 0.353850143 | 0.627708103 |
| O | 0.643143159 | 0.380569137 | 0.409727911 |
| O | 0.012470294 | 0.37559664 | 0.633907607 |
| O | 0.30076375 | 0.050433868 | 0.326261544 |
| O | 0.179869083 | 0.160089473 | 0.643246563 |
| O | 0.128951403 | 0.140300995 | 0.433283895 |
| O | 0.499765483 | 0.138843905 | 0.607693605 |
| O | 0.191102456 | 0.490857739 | 0.517814234 |
| O | 0.338859015 | 0.355306381 | 0.410401556 |
| O | 0.353605047 | 0.362652866 | 0.627204915 |
| O | 0.992037882 | 0.377608079 | 0.408861921 |
| O | 0.308263144 | 0.991892018 | 0.518180867 |
| O | 0.162182925 | 0.854789149 | 0.409713347 |
| O | 0.139046806 | 0.879688818 | 0.628489952 |
| O | 0.509868047 | 0.877301705 | 0.410241316 |
| O | 0.203203918 | 0.550428379 | 0.325363235 |

TABLE 8-continued

Hydrogen binds with O(2) on (VO)$_2$P$_2$O$_7$ Surface structure (b)
a = 8.362 Å; b = 9.536 Å; c = 19.994 Å
E(SCF) = −1241.799212 hartree

| | | | |
|---|---|---|---|
| O | 0.32724674 | 0.649832515 | 0.632967944 |
| O | 0.371961129 | 0.640272009 | 0.433248101 |
| O | 0.004639807 | 0.641020326 | 0.608819365 |
| O | 0.691367567 | 0.992333831 | 0.522589396 |
| O | 0.837266189 | 0.84830983 | 0.6266902 |
| O | 0.858456488 | 0.879874735 | 0.41057205 |
| O | 0.490325088 | 0.872237587 | 0.629913587 |
| O | 0.799332269 | 0.551172597 | 0.711438093 |
| O | 0.673610783 | 0.656521931 | 0.413485605 |
| O | 0.624221719 | 0.635595045 | 0.60510122 |
| O | 0.997210279 | 0.642861499 | 0.427799605 |
| O | 0.951530664 | 0.199798032 | 0.727242389 |
| O | 0.022228751 | 0.197859398 | 0.315580487 |
| O | 0.502178422 | 0.334603963 | 0.518612083 |
| O | 1.00309515 | 0.831317045 | 0.518698662 |
| O | 0.530943887 | 0.698181399 | 0.724649749 |
| O | 0.482034909 | 0.699027306 | 0.316191581 |
| H | 0.634455598 | 0.647136881 | 0.733212069 |
| H | 0.379498878 | 0.649924978 | 0.305553229 |
| H | 0.847899827 | 0.139494581 | 0.731209792 |
| H | 0.124322908 | 0.147348141 | 0.305540246 |
| H | 0.258045978 | 0.249488241 | 0.641633852 |

TABLE 9

O$_2$ binds with vanadium on (VO)$_2$P$_2$O$_7$ Surface
a = 8.362 Å; b = 9.536 Å; c = 19.994 Å
E(SCF) = −1273.179616 hartree

| | | | |
|---|---|---|---|
| V | 0.30556057 | 0.013311515 | 0.403289119 |
| V | 0.197943505 | 0.513859471 | 0.615152029 |
| V | 0.690547678 | 0.020833991 | 0.642767923 |
| V | 0.809371675 | 0.510180641 | 0.440677459 |
| V | 0.688009891 | 0.002245531 | 0.440726135 |
| V | 0.807728573 | 0.521610296 | 0.639046962 |
| V | 0.309384657 | 0.01456886 | 0.601495607 |
| V | 0.202495982 | 0.510134324 | 0.431704665 |
| P | 0.992518714 | 0.214291334 | 0.400361334 |
| P | 0.517937868 | 0.302969229 | 0.593509875 |
| P | 0.997809263 | 0.218528709 | 0.646749611 |
| P | 0.517475494 | 0.297370244 | 0.443391054 |
| P | 0.001142021 | 0.808500655 | 0.443233126 |
| P | 0.499912434 | 0.720755442 | 0.644096059 |
| P | 0.992431928 | 0.814080998 | 0.601030689 |
| P | 0.500643493 | 0.709513346 | 0.398596457 |
| O | 0.700279526 | 0.050032733 | 0.72152905 |
| O | 0.829772163 | 0.154159108 | 0.421134032 |
| O | 0.855562688 | 0.146002595 | 0.611798508 |
| O | 0.508474499 | 0.139661595 | 0.41894884 |
| O | 0.794694094 | 0.501225076 | 0.520321171 |
| O | 0.648722013 | 0.372158672 | 0.634144296 |
| O | 0.644960354 | 0.381483797 | 0.406331549 |
| O | 0.992151373 | 0.378160157 | 0.627014604 |
| O | 0.286732401 | 0.041372104 | 0.324695233 |
| O | 0.162125465 | 0.159870238 | 0.626598754 |
| O | 0.134725741 | 0.139770185 | 0.433139699 |
| O | 0.499086178 | 0.146747022 | 0.619551247 |
| O | 0.160641159 | 0.515616938 | 0.529075271 |
| O | 0.349601752 | 0.354904989 | 0.440852051 |
| O | 0.359155844 | 0.373815316 | 0.587808321 |
| O | 0.990507854 | 0.374570378 | 0.421142332 |
| O | 0.319093023 | 0.004436944 | 0.52138202 |
| O | 0.163238355 | 0.856325248 | 0.417557915 |
| O | 0.146264384 | 0.881157006 | 0.626825348 |
| O | 0.50632438 | 0.876128102 | 0.409093684 |
| O | 0.20940756 | 0.528599575 | 0.350316911 |
| O | 0.346568996 | 0.66406717 | 0.612593914 |
| O | 0.379988092 | 0.642775141 | 0.447087924 |
| O | 0.989966161 | 0.65372416 | 0.613367998 |
| O | 0.680688893 | 0.985486553 | 0.520469858 |
| O | 0.841728414 | 0.873177191 | 0.632590741 |
| O | 0.858734415 | 0.881773026 | 0.410745405 |
| O | 0.49295766 | 0.886541171 | 0.63366009 |

TABLE 9-continued

O₂ binds with vanadium on (VO)₂P₂O₇ Surface
a = 8.362 Å; b = 9.536 Å; c = 19.994 Å
E(SCF) = −1273.179616 hartree

| | | | |
|---|---|---|---|
| O | 0.794495578 | 0.549825475 | 0.717743743 |
| O | 0.672382017 | 0.657545669 | 0.409984645 |
| O | 0.647385078 | 0.657732211 | 0.610272138 |
| O | 0.992731374 | 0.646665011 | 0.43223851 |
| O | 0.981589539 | 0.205586212 | 0.725463624 |
| O | 0.008449506 | 0.207990592 | 0.321345326 |
| O | 0.583601639 | 0.282945116 | 0.518450444 |
| O | 0.987586146 | 0.841189971 | 0.521753483 |
| O | 0.505929404 | 0.698155558 | 0.722388566 |
| O | 0.450471794 | 0.687759376 | 0.323449694 |
| H | 0.601676709 | 0.643781544 | 0.736529643 |
| H | 0.352016242 | 0.625346468 | 0.32069006 |
| H | 0.882259351 | 0.156284779 | 0.739248564 |
| H | 0.104909621 | 0.154878517 | 0.3071923 |
| O | 0.151494358 | 0.551866402 | 0.705472585 |
| O | 0.262384462 | 0.445830324 | 0.698581802 |

TABLE 10

O₂H binds with vanadium on (VO)₂P₂O₇ Surface
a = 8.362 Å; b = 9.536 Å; c = 19.994 Å
E(SCF) = −1273.790463 hartree

| | | | |
|---|---|---|---|
| V | 0.307572091 | 0.014163252 | 0.401691318 |
| V | 0.188668879 | 0.513416454 | 0.610959062 |
| V | 0.688415538 | 0.021240716 | 0.642018978 |
| V | 0.81127043 | 0.510672309 | 0.44119417 |
| V | 0.688234622 | 0.002537751 | 0.441612306 |
| V | 0.801505168 | 0.523211145 | 0.639784734 |
| V | 0.306056075 | 0.018707542 | 0.602463897 |
| V | 0.200954529 | 0.508984061 | 0.42516313 |
| P | 0.992578991 | 0.213844934 | 0.399128884 |
| P | 0.516748538 | 0.304177999 | 0.592691483 |
| P | 0.995228182 | 0.221581557 | 0.648410126 |
| P | 0.518173502 | 0.298383892 | 0.44282586 |
| P | 0.004877153 | 0.807830684 | 0.443845404 |
| P | 0.490250858 | 0.721605831 | 0.642616238 |
| P | 0.992766309 | 0.814116222 | 0.602773833 |
| P | 0.502637766 | 0.709850463 | 0.397713113 |
| O | 0.699095651 | 0.048246184 | 0.7211014 |
| O | 0.831124516 | 0.154144567 | 0.421630574 |
| O | 0.856387538 | 0.147363143 | 0.612190876 |
| O | 0.508961259 | 0.140020353 | 0.4186774 |
| O | 0.798402084 | 0.503715027 | 0.521234397 |
| O | 0.648019151 | 0.371927161 | 0.633907548 |
| O | 0.646064186 | 0.382138382 | 0.405988147 |
| O | 0.988330495 | 0.383357888 | 0.630394019 |
| O | 0.288494129 | 0.040461493 | 0.323001727 |
| O | 0.160923119 | 0.166358993 | 0.628417493 |
| O | 0.136964684 | 0.141203788 | 0.430987084 |
| O | 0.49728452 | 0.148457384 | 0.619397777 |
| O | 0.156880881 | 0.511908249 | 0.527625745 |
| O | 0.350391454 | 0.355911562 | 0.439925661 |
| O | 0.359617186 | 0.37652325 | 0.585597029 |
| O | 0.991597244 | 0.374957346 | 0.418661554 |
| O | 0.313527425 | 0.006194092 | 0.522464211 |
| O | 0.164952087 | 0.857826315 | 0.41716371 |
| O | 0.140967676 | 0.887205614 | 0.630473738 |
| O | 0.507485404 | 0.876698105 | 0.408751567 |
| O | 0.212428649 | 0.52565004 | 0.344388408 |
| O | 0.333700109 | 0.668864955 | 0.612771972 |
| O | 0.378138063 | 0.642414767 | 0.443873449 |
| O | 0.99338559 | 0.653628061 | 0.618070705 |
| O | 0.678187183 | 0.986812298 | 0.521456106 |
| O | 0.836872875 | 0.870158148 | 0.630704463 |
| O | 0.860441862 | 0.881427033 | 0.413504391 |
| O | 0.488359104 | 0.88745121 | 0.634419335 |
| O | 0.785640026 | 0.5539487 | 0.71835675 |
| O | 0.673946251 | 0.658526381 | 0.410364071 |
| O | 0.637772315 | 0.657158098 | 0.609958591 |
| O | 0.997154498 | 0.646231243 | 0.430807493 |
| O | 0.975509927 | 0.207741107 | 0.726948972 |
| O | 0.004427793 | 0.205538504 | 0.319923535 |

TABLE 10-continued

O₂H binds with vanadium on (VO)₂P₂O₇ Surface
a = 8.362 Å; b = 9.536 Å; c = 19.994 Å
E(SCF) = −1273.790463 hartree

| | | | |
|---|---|---|---|
| O | 0.584558814 | 0.283046663 | 0.517987607 |
| O | 0.996448396 | 0.834421285 | 0.523090134 |
| O | 0.491217482 | 0.692638779 | 0.721490827 |
| O | 0.458002544 | 0.690164778 | 0.321593516 |
| H | 0.590515409 | 0.64240999 | 0.735390631 |
| H | 0.361286236 | 0.627689119 | 0.316795586 |
| H | 0.877024763 | 0.155286927 | 0.739334656 |
| H | 0.101407462 | 0.154114482 | 0.305212516 |
| O | 0.172572473 | 0.547852473 | 0.724464398 |
| O | 0.268011312 | 0.438417689 | 0.693259713 |
| H | 0.257651544 | 0.614533562 | 0.73814618 |

TABLE 11

O₂ dissociatively binds with vanadium atoms on (VO)₂P₂O₇ Surface
a = 8.362 Å; b = 9.536 Å; c = 19.994 Å
E(SCF) = −1273.245865 hartree

| | | | |
|---|---|---|---|
| V | 0.211081787 | 0.017049479 | 0.449294666 |
| V | 0.198725213 | 0.515900249 | 0.626627866 |
| V | 0.688794903 | 0.021644562 | 0.645018979 |
| V | 0.796121857 | 0.50923136 | 0.422512119 |
| V | 0.699685979 | 0.0074933 | 0.424150897 |
| V | 0.809025912 | 0.521894658 | 0.646887388 |
| V | 0.298752195 | 0.016063627 | 0.626159489 |
| V | 0.286025143 | 0.51799254 | 0.448604621 |
| P | 0.973456423 | 0.217067262 | 0.383268475 |
| P | 0.51850846 | 0.305599325 | 0.597340577 |
| P | 0.991209791 | 0.22413941 | 0.642230131 |
| P | 0.521348473 | 0.28597093 | 0.447320664 |
| P | −0.022650204 | 0.785555111 | 0.446946806 |
| P | 0.505627794 | 0.724263506 | 0.64274586 |
| P | 0.979744121 | 0.804667093 | 0.597009969 |
| P | 0.523100251 | 0.71672159 | 0.380741483 |
| O | 0.698302419 | 0.046880673 | 0.723755506 |
| O | 0.81628076 | 0.139421679 | 0.369848777 |
| O | 0.843534665 | 0.152650841 | 0.611491128 |
| O | 0.536905914 | 0.142196483 | 0.416476015 |
| O | 0.778264213 | 0.514916313 | 0.501902735 |
| O | 0.649647933 | 0.375271683 | 0.637879529 |
| O | 0.616600244 | 0.390753516 | 0.405591494 |
| O | 0.988304983 | 0.385540638 | 0.623812212 |
| O | 0.285666734 | 0.035182303 | 0.374767518 |
| O | 0.148664727 | 0.16771991 | 0.614473014 |
| O | 0.053163608 | 0.151701589 | 0.447666108 |
| O | 0.497266361 | 0.151017549 | 0.623273245 |
| O | 0.159121149 | 0.540684062 | 0.511097092 |
| O | 0.344456949 | 0.329366889 | 0.451333911 |
| O | 0.361114948 | 0.383106956 | 0.592883822 |
| O | 0.941109675 | 0.373070738 | 0.396527288 |
| O | 0.338413112 | 0.039072192 | 0.511680915 |
| O | 0.154614673 | 0.82772962 | 0.450840536 |
| O | 0.136915983 | 0.882580462 | 0.59246441 |
| O | 0.557834394 | 0.872478139 | 0.393755402 |
| O | 0.211048695 | 0.534718029 | 0.374031691 |
| O | 0.348758786 | 0.667269439 | 0.614696638 |
| O | 0.444853034 | 0.651899646 | 0.44565765 |
| O | 1.000347515 | 0.650760327 | 0.623953377 |
| O | 0.713707618 | 1.008269631 | 0.503857932 |
| O | 0.848454993 | 0.875221938 | 0.637042626 |
| O | 0.882834401 | 0.893565853 | 0.406801816 |
| O | 0.508802626 | 0.88516489 | 0.623560315 |
| O | 0.799484465 | 0.54695521 | 0.725612036 |
| O | 0.678932425 | 0.637430074 | 0.366446822 |
| O | 0.654248079 | 0.652381315 | 0.613095972 |
| O | 0.95914456 | 0.643760904 | 0.414266134 |
| O | 0.986872874 | 0.211944117 | 0.721225921 |
| O | 0.087358711 | 0.21032294 | 0.321205894 |
| O | 0.589162165 | 0.287282994 | 0.522317443 |
| O | 0.91026162 | 0.783973389 | 0.522004506 |
| O | 0.50791572 | 0.7137475 | 0.721832039 |
| O | 0.406906276 | 0.710619556 | 0.319413018 |
| H | 0.599346572 | 0.65970483 | 0.739644735 |

TABLE 11-continued

O₂ dissociatively binds with vanadium atoms on (VO)₂P₂O₇ Surface
a = 8.362 Å; b = 9.536 Å; c = 19.994 Å
E(SCF) = −1273.245865 hartree

| | | | |
|---|---|---|---|
| H | 0.318097292 | 0.640052221 | 0.327266668 |
| H | 0.89350779 | 0.159252281 | 0.738358471 |
| H | 0.176497451 | 0.139896458 | 0.328348866 |
| O | 0.21713819 | 0.49348635 | 0.704874601 |
| O | 0.280256599 | −0.006766123 | 0.704394181 |

TABLE 12

α₁-VOPO₄ bulk
a = 6.246 Å; b = 6.246 Å; c = 4.423 Å
E(SCF) = −317.7416348 hartree

| | | | |
|---|---|---|---|
| O | 0.500119279 | 0.70184149 | 0.294012908 |
| O | 0.499892484 | 0.298155581 | 0.294010938 |
| O | 0.798169418 | 0.000119597 | 0.294012991 |
| O | 0.201852375 | 0.99988 | 0.294023159 |
| O | 0.999880324 | 0.798158286 | 0.705990845 |
| O | 0.000107337 | 0.201844669 | 0.705992728 |
| O | 0.701831151 | 0.499880471 | 0.705989792 |
| O | 0.298147185 | 0.500120046 | 0.705980117 |
| V | −0.000011721 | 0.500000729 | 0.616318385 |
| O | −0.000011666 | 0.49999925 | 0.257530309 |
| V | 0.500011912 | −0.000000813 | 0.383631246 |
| O | 0.500011969 | 0.000000678 | 0.74251224 |
| P | −0.000002121 | −0.000001648 | 0.499996915 |
| P | 0.500002079 | 0.500001664 | 0.499997429 |

TABLE 13

α₁-VOPO₄ surface
a = 6.246 Å; b = 6.246 Å; c = 12.145 Å
E(SCF) = −317.742408 hartree

| | | | |
|---|---|---|---|
| O | 0.51703 | 0.69205 | 0.26513 |
| P | 0.51691 | 0.49021 | 0.340540063 |
| O | 0.51681 | 0.289128078 | 0.264538423 |
| O | 0.815373757 | −0.009527628 | 0.264412379 |
| O | 0.218447604 | 0.990263792 | 0.264426199 |
| O | 1.01679867 | 0.788762089 | 0.415813665 |
| O | 0.01700568 | 0.19171999 | 0.415879008 |
| O | 0.71854932 | 0.489879447 | 0.416141462 |
| O | 0.315265241 | 0.490088737 | 0.416136517 |
| V | 1.016903519 | 0.490235723 | 0.380757531 |
| O | 1.016899287 | 0.49021389 | 0.25094447 |
| V | 0.51690567 | −0.009462075 | 0.299744854 |
| O | 0.516924593 | −0.009329028 | 0.429542922 |
| P | 1.016895479 | 0.990327894 | 0.340127806 |

TABLE 14

Hydrogen binds with O(1) on the α₁-VOPO₄ surface
a = 6.246 Å; b = 6.246 Å; c = 12.145 Å
E(SCF) = −318.3201147 hartree

| | | | |
|---|---|---|---|
| O | 0.51703 | 0.69205 | 0.26513 |
| P | 0.51691 | 0.49021 | 0.341091692 |
| O | 0.51681 | 0.291696613 | 0.266138636 |
| O | 0.815444487 | −0.006521128 | 0.261107703 |
| O | 0.217237951 | 0.994340466 | 0.258391377 |
| O | 1.021515126 | 0.797662761 | 0.413263034 |
| O | 0.020777772 | 0.197795181 | 0.41107865 |
| O | 0.720454286 | 0.495413993 | 0.415968336 |
| O | 0.317385012 | 0.499155906 | 0.418130354 |
| V | 1.016785944 | 0.49720681 | 0.378025239 |
| O | 1.017885687 | 0.498581387 | 0.248123541 |
| V1 | 0.515123142 | −0.011565179 | 0.288877908 |

TABLE 14-continued

Hydrogen binds with O(1) on the α₁-VOPO₄ surface
a = 6.246 Å; b = 6.246 Å; c = 12.145 Å
E(SCF) = −318.3201147 hartree

| | | | |
|---|---|---|---|
| O | 0.506228888 | −0.019007684 | 0.433849241 |
| P | 1.017671513 | 0.996674705 | 0.335554889 |
| H | 0.433644987 | 0.857606114 | 0.468699539 |

TABLE 15

Hydrogen binds with O(2) on the α₁-VOPO₄ surface
a = 6.246 Å; b = 6.246 Å; c = 12.145 Å
E(SCF) = −318.319053 hartree

| | | | |
|---|---|---|---|
| O | 0.505643439 | 0.690127267 | 0.259189723 |
| P | 0.527108514 | 0.490552202 | 0.32983648 |
| O | 0.505358259 | 0.291154403 | 0.258927573 |
| O | 0.80903262 | −0.009184882 | 0.270479776 |
| O | 0.209847958 | 0.990192148 | 0.265451413 |
| O | 1.016886434 | 0.788515017 | 0.420050114 |
| O | 0.018016773 | 0.192237663 | 0.420144507 |
| O | 0.710132588 | 0.489654105 | 0.414366729 |
| O | 0.326491818 | 0.491619658 | 0.419463558 |
| V | 1.005775348 | 0.490334977 | 0.377970747 |
| O | 1.01777112 | 0.490345106 | 0.247987146 |
| V | 0.50846666 | −0.009208863 | 0.301994807 |
| O | 0.503403122 | −0.008535912 | 0.432533423 |
| P | 1.013059159 | 0.990381769 | 0.344177063 |
| H | 0.378616186 | 0.482125342 | 0.495276943 |

TABLE 16

α₂-VOPO₄
a = 6.111 Å; b = 6.111 Å; c = 4.623 Å
E(SCF) = −317.748731 hartree

| | | | |
|---|---|---|---|
| O | 0.209587036 | 0.951127905 | 0.304388019 |
| O | 0.290412814 | 0.548875489 | 0.304385244 |
| O | 0.548875757 | 0.209589539 | 0.304387012 |
| O | 0.951123994 | 0.290414974 | 0.304387571 |
| O | 0.790413405 | 0.048868588 | 0.695615293 |
| O | 0.709586741 | 0.451128043 | 0.69561808 |
| O | 0.451127681 | 0.790410875 | 0.695616517 |
| O | 0.048872655 | 0.709584597 | 0.695615941 |
| V | 0.250001831 | 0.250004546 | 0.221315823 |
| O | 0.249999979 | 0.250003141 | 0.87681897 |
| V | 0.749998176 | 0.749995463 | 0.778718219 |
| O | 0.750000016 | 0.749996843 | 0.123149282 |
| P | 0.249999513 | 0.750000677 | 0.499998478 |
| P | 0.750000481 | 0.249999319 | 0.49998555 |

TABLE 17

α₂-VOPO₄ surface
a = 6.111 Å; b = 6.111 Å; c = 15.762 Å
E(SCF) = −317.7462076 hartree

| | | | |
|---|---|---|---|
| O | 0.16903 | 0.9185 | 0.42414 |
| P | 0.20945 | 0.71738 | 0.481563908 |
| O | 0.24986 | 0.516299167 | 0.424024376 |
| O | 0.508456892 | 0.175038668 | 0.424115167 |
| O | 0.910424157 | 0.25981842 | 0.424117023 |
| O | 0.752145478 | 0.016363713 | 0.538907556 |
| O | 0.666730306 | 0.418396848 | 0.538905308 |
| O | 0.410538895 | 0.759785134 | 0.538901178 |
| O | 0.008331813 | 0.675057947 | 0.538895851 |
| V | 0.2094446 | 0.217397084 | 0.397045016 |
| O | 0.209419727 | 0.217433764 | 0.296873152 |
| V | 0.709433473 | 0.717354899 | 0.565985052 |
| O | 0.709411957 | 0.71738802 | 0.666138703 |
| P | 0.709454889 | 0.217355214 | 0.481485178 |

TABLE 18

Hydrogen binds with O(1) on the $\alpha_2$-VOPO$_4$ surface
a = 6.111 Å; b = 6.111 Å; c = 15.762 Å
E(SCF) = −318.3285407 hartree

| | | | |
|---|---|---|---|
| O | 0.16903 | 0.9185 | 0.42414 |
| P | 0.20945 | 0.71738 | 0.481725757 |
| O | 0.24986 | 0.517463251 | 0.423409802 |
| O | 0.510011335 | 0.174445219 | 0.426038162 |
| O | 0.910345296 | 0.260523237 | 0.426587811 |
| O | 0.755261056 | 0.017723283 | 0.542735992 |
| O | 0.662899367 | 0.417683413 | 0.541705784 |
| O | 0.410068084 | 0.762297225 | 0.539156523 |
| O | 0.007330934 | 0.670676568 | 0.538199946 |
| V | 0.209973454 | 0.217884538 | 0.397833913 |
| O | 0.209613189 | 0.218006707 | 0.297517493 |
| V | 0.7091985 | 0.716182726 | 0.56874838 |
| O | 0.709449531 | 0.713222474 | 0.679789754 |
| P | 0.709959278 | 0.216350499 | 0.483894744 |
| H | 0.68659707 | 0.574831617 | 0.709964435 |

TABLE 19

Hydrogen binds with O(2) on the $\alpha_2$-VOPO$_4$ surface
a = 6.111 Å; b = 6.111 Å; c = 4.623 Å
E(SCF) = −318.3175941 hartree

| | | | |
|---|---|---|---|
| O | 0.16903 | 0.9185 | 0.42414 |
| P | 0.20945 | 0.71738 | 0.477798066 |
| O | 0.24986 | 0.523249352 | 0.421131576 |
| O | 0.510801383 | 0.177007257 | 0.423471902 |
| O | 0.913891403 | 0.26272538 | 0.420667849 |
| O | 0.761382608 | 0.015608304 | 0.534903451 |
| O | 0.671635573 | 0.422763277 | 0.535807612 |
| O | 0.407017347 | 0.770227628 | 0.54662132 |
| O | 0.033745468 | 0.668118796 | 0.545112265 |
| V | 0.212763223 | 0.218707109 | 0.391855003 |
| O | 0.212775716 | 0.215160568 | 0.291628555 |
| V | 0.736316044 | 0.716668372 | 0.570443145 |
| O | 0.72077673 | 0.718842454 | 0.671098893 |
| P | 0.715219431 | 0.219490394 | 0.4791041 |
| H | 0.336781021 | 0.764307913 | 0.602761146 |

TABLE 20

β-VOPO4
a = 7.911 Å; b = 6.212 Å; c = 7.189 Å
E(SCF) = −635.5033472 hartree

| | | | |
|---|---|---|---|
| O | 0.129034516 | 0.550386121 | 0.240617852 |
| O | 0.370626487 | 0.44963591 | 0.740725304 |
| O | 0.870853143 | 0.050394042 | 0.759369529 |
| O | 0.629278329 | 0.949649363 | 0.259285709 |
| O | 0.870853146 | 0.449605975 | 0.759369529 |
| O | 0.629278326 | 0.550350662 | 0.259285709 |
| O | 0.129034516 | 0.949613893 | 0.240617855 |
| O | 0.370626489 | 0.050364112 | 0.740725307 |
| V | 0.174705151 | 0.250000007 | 0.227521187 |
| P | 0.878698548 | 0.250000008 | 0.887622469 |
| O | 0.720538994 | 0.250000012 | 0.019879261 |
| O | 0.044429719 | 0.250000007 | 1.000468565 |
| O | 0.362022466 | 0.250000007 | 0.146293867 |
| V | 0.325118087 | 0.750000011 | 0.727336747 |
| P | 0.62158928 | 0.750000012 | 0.387457884 |
| O | 0.77974856 | 0.750000009 | 0.51960787 |
| O | 0.455848108 | 0.750000013 | 0.50054115 |
| O | 0.137914718 | 0.750000013 | 0.645948661 |
| V | 0.825237259 | 0.750000008 | 0.772455191 |
| P | 0.121227622 | 0.750000008 | 0.112373417 |
| O | 0.279418823 | 0.750000001 | 0.980157724 |
| O | 0.955517111 | 0.750000009 | −0.00051998 |
| O | 0.637920536 | 0.750000008 | 0.853697213 |
| V | 0.674848397 | 0.250000013 | 0.272694199 |

TABLE 20-continued

β-VOPO4
a = 7.911 Å; b = 6.212 Å; c = 7.189 Å
E(SCF) = −635.5033472 hartree

| | | | |
|---|---|---|---|
| P | 0.37834625 | 0.25000001 | 0.61253865 |
| O | 0.220205676 | 0.250000008 | 0.480364586 |
| O | 0.544107788 | 0.250000012 | 0.499483974 |
| O | 0.862064867 | 0.250000013 | 0.354061843 |

TABLE 21

X$_1$-VOPO$_4$ bulk
a = 9.730 Å; b = 9.525 Å; c = 7.860 Å
E = −1270.737274 hartree

| | | | |
|---|---|---|---|
| V | 0.03871603 | 0.011352013 | 0.298320072 |
| P | 0.07786125 | 0.220516024 | −0.014864081 |
| O | 0.284673759 | 0.001667515 | 0.703976768 |
| O | 1.013826981 | 0.146199333 | 0.824703862 |
| O | 0.513502591 | 0.14297754 | 0.822281233 |
| O | 0.975653837 | 0.132695681 | 0.485731967 |
| V | 0.537085934 | 0.509822736 | 0.203153112 |
| P | 0.406174179 | 0.285307117 | 0.481226434 |
| O | 0.786805324 | 0.502753648 | 0.797535585 |
| O | 0.48106375 | 0.365714411 | 0.636171437 |
| O | −0.014734137 | 0.368991811 | 0.637865112 |
| O | 0.510358834 | 0.373463389 | 0.983895343 |
| V | 0.446907427 | −0.006307189 | 0.703854983 |
| P | 0.576926489 | 0.217899546 | 0.982703653 |
| O | 0.200998226 | 0.00334941 | 0.296851728 |
| O | 0.50215599 | 0.137110662 | 0.136847495 |
| O | 1.002644474 | 0.140177217 | 0.139181067 |
| O | 0.4729895 | 0.130050162 | 0.483986968 |
| V | 0.949088501 | 0.496651835 | 0.797983006 |
| P | 0.909993473 | 0.288525605 | 0.483380482 |
| O | 0.699362777 | 0.502280201 | 0.202607522 |
| O | −0.026472131 | 0.363617621 | 0.323418018 |
| O | 0.470300326 | 0.360695288 | 0.321849378 |
| O | 0.012179009 | 0.37640132 | −0.013735584 |
| V | 0.948678095 | 0.997345611 | 0.704379318 |
| P | 0.909105103 | 0.788147915 | 1.01752105 |
| O | 0.699730907 | 1.001875921 | 0.297787171 |
| O | −0.028089406 | 0.863157366 | 0.178274288 |
| O | 0.470124021 | 0.860693898 | 0.178507227 |
| O | 0.011820956 | 0.876470602 | 0.516577366 |
| V | 0.44655742 | 0.493276078 | 0.796299955 |
| P | 0.57718834 | 0.717794918 | 0.518527302 |
| O | 0.202018831 | 0.504536141 | 0.205032692 |
| O | 0.502192932 | 0.637205801 | 0.363943637 |
| O | 1.00389211 | 0.640727294 | 0.363461869 |
| O | 0.472635643 | 0.630229488 | 0.01629401 |
| V | 0.537413295 | 1.009397959 | 0.297410475 |
| P | 0.40622363 | 0.785723211 | 0.01834048 |
| O | 0.786427338 | 1.003956907 | 0.70431445 |
| O | 0.481619247 | 0.866082729 | 0.864129051 |
| O | −0.0154682 | 0.869185147 | 0.864059829 |
| O | 0.510891032 | 0.873445585 | 0.516692087 |
| V | 0.039741823 | 0.512385248 | 0.20401379 |
| P | 0.078261916 | 0.72093348 | 0.518771179 |
| O | 0.284298912 | 0.501334843 | 0.796059065 |
| O | 1.013758986 | 0.646020072 | 0.678109244 |
| O | 0.513683617 | 0.642637152 | 0.678474961 |
| O | 0.975957161 | 0.632807407 | 1.016175474 |
| O | 0.229213579 | 0.222678893 | −0.003395144 |
| O | 0.255012448 | 0.282686109 | 0.492458494 |
| O | 0.255017955 | 0.783395102 | 0.00670879 |
| O | 0.229620806 | 0.723705593 | 0.508236947 |
| O | 0.728181725 | 0.221238281 | 0.994434885 |
| O | 0.728500081 | 0.720785178 | 0.506917379 |
| O | −0.241356974 | 0.285869372 | 0.494362557 |
| O | −0.242115722 | 0.784787794 | 1.004874563 |

TABLE 22

Hydrogen binds with O(1) = P on the $X_1$-VOPO$_4$ bulk
a = 9.525 Å; b = 7.860 Å; c = 14.607 Å
E = −635.9855629 hartree

| | | | |
|---|---|---|---|
| O | −0.00353 | 0.72082 | 0.26274 |
| V | 0.97624 | 0.71344 | 0.369718967 |
| O | 0.85002 | 0.879882072 | 0.389463194 |
| O | 0.117934899 | 0.827783673 | 0.427159745 |
| V | 0.486333165 | 0.19313312 | 0.436208753 |
| P | 0.268965976 | 0.469116163 | 0.359448257 |
| O | 0.33762083 | 0.645817851 | 0.388404439 |
| O | 0.346796982 | 0.995406644 | 0.411368139 |
| P | 0.189986628 | 0.999184085 | 0.457307015 |
| O | 0.10986969 | 0.137913011 | 0.395123696 |
| O | 0.103570974 | 0.488829455 | 0.393331106 |
| O | 0.531424495 | 0.187928889 | 0.541056594 |
| O | 0.334757264 | 0.342596326 | 0.432329833 |
| O | −0.058574569 | 0.274368749 | 0.519849711 |
| O | 0.83781867 | 0.186759733 | 0.34970992 |
| V | 0.461666986 | 0.812684244 | 0.3540216 |
| P | 0.682313666 | 0.520888241 | 0.428968931 |
| O | 0.609198107 | 0.363395849 | 0.389478224 |
| O | 0.607152579 | 0.019256143 | 0.373486957 |
| V | −0.024643522 | 0.294501361 | 0.414401021 |
| P | 0.761642464 | 0.012349304 | 0.326125342 |
| O | 0.843134523 | 0.522061927 | 0.400205378 |
| O | 0.451568471 | 0.814523127 | 0.246473138 |
| O | 0.618515107 | 0.68539448 | 0.39260616 |
| O | 0.280365125 | 0.419699352 | 0.262365076 |
| O | 0.75673916 | −0.031236946 | 0.228234842 |
| O | 0.193748371 | 1.033293365 | 0.556292688 |
| O | 0.676792876 | 0.521934873 | 0.537043964 |
| H | 0.64262998 | 0.415413139 | 0.565116627 |

The β and δ phases of VOPO$_4$. The β and δ phases are the most stable phases, but as shown in FIG. 28, they do not lead to layers that could form stable surfaces for the reactions. The O—H bond strength for β- and δ-VOPO$_4$ were did calculated, because they do not have layered structures, making it difficult to decide which surface is stable and how to saturate the surface (remove broken bonds). These structures do not lead to P=o bonds. Instead all P are connected through o to four vanadium atoms. However, the vanadium 3s core orbital energy (chemical shift) for bulk β-VOPO$_4$ was calculated and compared to those from $\alpha_I$- and $\alpha_{II}$-VOPO$_4$ (using B3LYP/Crystal). It was found that the 3s core orbital energies and net charge on the O(1) are similar, and hence their VO—H bond strengths are expected to be similar.

The $\alpha_I$ and $\alpha_{II}$ Phases of VOPO$_4$.

The $\alpha_I$ and $\alpha_{II}$ phases lead to layered structures (FIG. 28) and are nearly as stable as β and δ (FIG. 27). For the DFT calculations the surfaces was prepared by cleaving parallel to the layer direction in such a way that only van der Waals bonds are broken.

Figure 30:
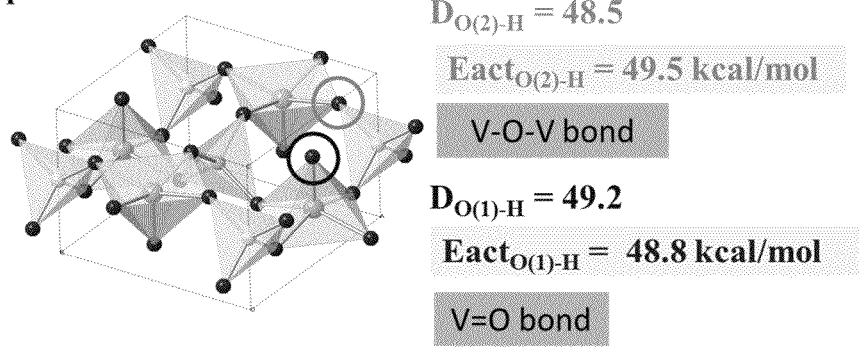
FIGS. 30(a) and (b) show O—H bond strength for oxygen on the $\alpha_I$- and $\alpha_{II}$-VOPO$_4$ surfaces bonded to V atoms and the corresponding lower bound on the activation for n-butane C—H cleavage. None of these oxygens are believed to be responsible for the observed activation of butane.
Figure 30:
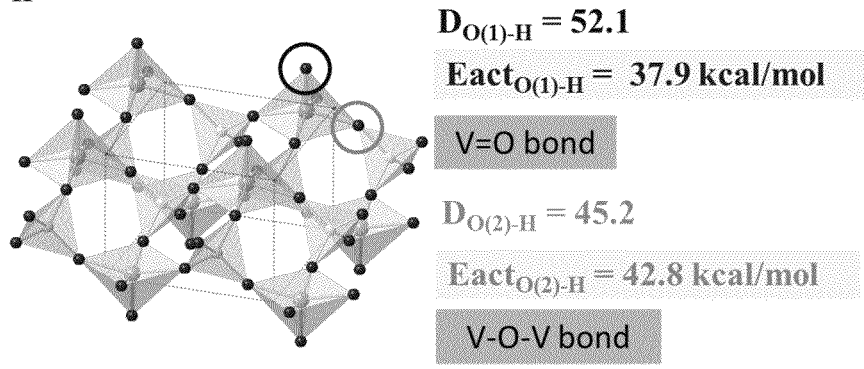

The results are shown in FIG. 30. For the $\alpha_I$ surface, it is found $D_{O(1)-H}$=49.2 and $D_{O(2)-H}$=48.5 kcal/mol, far too weak to activate butane.

For the $\alpha_{II}$-surface, it is found $D_{O(1)-H}$=52.1 and $D_{O(2)-H}$=45.2 kcal/mol, also far too weak to activate butane.

This indicates that none of the vanadium oxygen sites on the $\alpha_I$- or $\alpha_{II}$-surfaces can be the reactive center for VPO chemistry.

the X1 Phase of VOPO4

Figure 31:
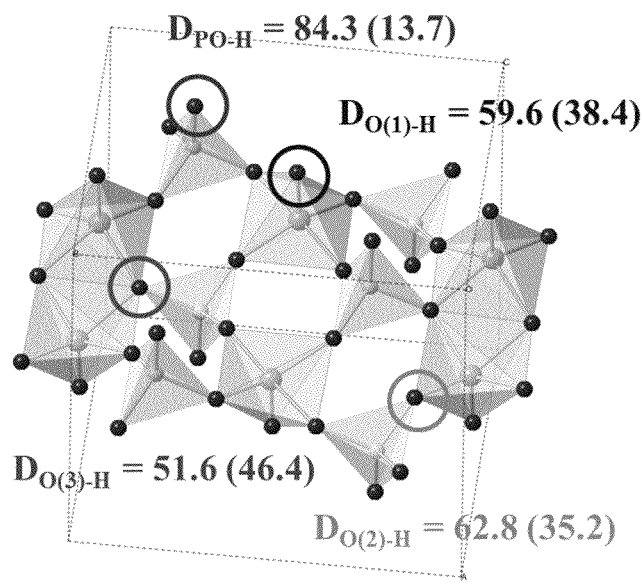
FIG. 31 shows O—H bond strengths for oxygen on the X1-VOPO$_4$ surface, but now including the possibility of bonding to the P═O bond. Each number in parentheses is the corresponding lower bound on the activation for n-butane C—H cleavage. The O—H bond strength of 84.3 kcal/mol to the P═O bond leads to a lower bound on the activation energy of 13.7 kcal/mol, which is the first candidate site whose minimum activation energy is compatible with experiment.

Having eliminated the β, δ, $\alpha_I$- or $\alpha_{II}$-surfaces, the X1 phase was turned to despite it being much less stable (FIG. 27). The results are shown in FIG. 31 where it is seen that $D_{O(1)-H}$=59.6, $D_{O(2)-H}$=62.8 and $D_{O(2)-H}$=51.6 kcal/mol. Thus none of the V—O bonds on the X1 phase are believed to be responsible for activating butane.

To summarize, the reduced surface (VO)P$_2$O$_7$ and the surfaces of all five known phases of the oxidized form VOPO$_4$ have been examined, and it has been found that none has a surface V—O site capable of activating butane. Yet the experiments show that there must be a site that can do this and it must lead to bond of at least $D_{SS-H}$=84 kcal/mol. A possible explanation is provided in the next Example (Example 12).

Example 12

Application of the Reduction-Coupled Oxo Activation (ROA) Principle for Selective Oxidation to Complex Products: Investigation of P=O Moieties as the Activation Center in VPO Catalyst The P=O Bond It is the P=O bond that the inventors believe responsible for activating butane. This does not appear to the inventors to have been considered by anyone. The results are shown on FIG. 32, where it is find that $D_{PO(1)-H}$=84.3 kcal/mol. P=O bonds are normally far less reactive. For example, for P$_4$O$_{10}$ (FIG. 17a) $D_{PO(1)-H}$=28.2 kcal/mol was calculated. In contrast, replacing an adjacent P=O with V=O increases the P=O bond to $D_{PO(1)-H}$=60.5 kcal/mol (FIG. 17b), while replacing two P=O with V=O increases the P=O bond to $D_{PO(1)-H}$=84.3 kcal/mol (FIG. 17c).

Figure 32:
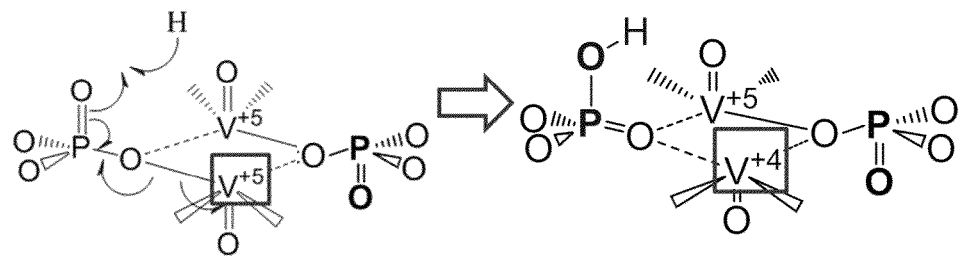
FIG. 32 shows valence bond description of the hydrogen abstraction process by P═O. This illustrates the new Reduction-Coupled Oxo Activation (ROA) reaction mechanism.

The ROA principle believed by the inventors to underlying the unexpected ability of the P=O bond of the X1 phase of VOPO$_4$ to active butane is shown in FIG. 32.

In FIG. 32, the P is initially $P^{+5}$ with one P=O bond and three single bonds bridging to adjacent V atoms.

Also in FIG. 32, the $V^{+5}$ has one V=O bond with 3 electrons shared between the remaining 4 bonds to the four O that bridge to the other P or V. Since this V started with five valence electrons, The Valence Bond view is that there are 3 covalent V—O bonds and one donor-acceptor V . . . O bond.

As further shown in FIG. 32, reacting the H to the P=O leads to P—O—H but instead of this leaving an unpaired spin on a $P^{+4}$, the P now forms a P=O bond to one of the V, reaming $P^{+5}$.

This converts what had been a V—O—P unit with single bonds to both V and P to V . . . O=P with a donor acceptor bond to the V, leaving the V with an extra electron in the $d_{xy}$ orbital, and hence $V^{+4}$, as can also be seen in FIG. 32.

It is the ability of the $V^{+5}$ to accept this electron that the inventors believe makes the $D_{PO(1)-H}$ bond so strong.

Figure 33:
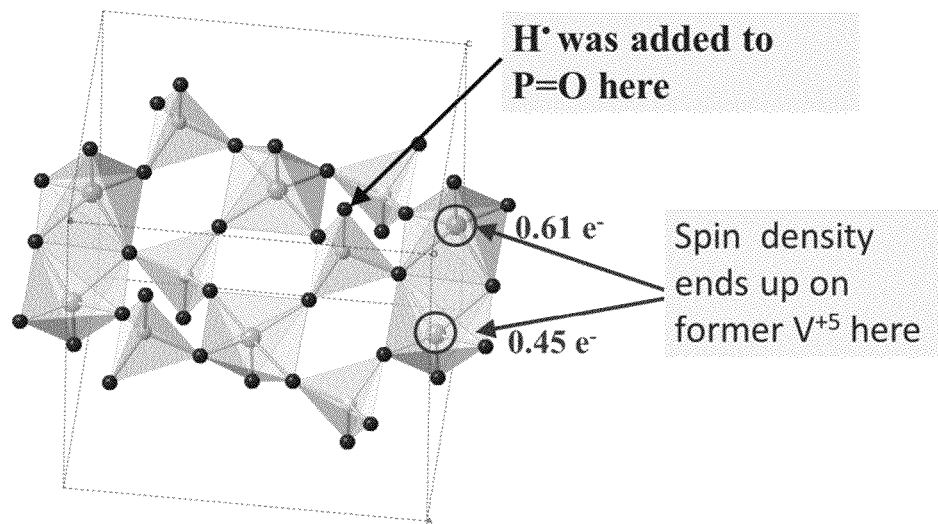
FIG. 33 shows spin density analysis shows that the electron and proton from hydrogen atom abstracted from butane are decoupled. The proton binds with O═P, whereas the electron is transferred to vanadium (in this case partially on two vanadium atoms).

Indeed, the spin analysis after bonding the H to P=O of the X1 phase shows 0.61 e on one neighboring V and 0.45 e on the other. (FIG. 33)

Figure 34:
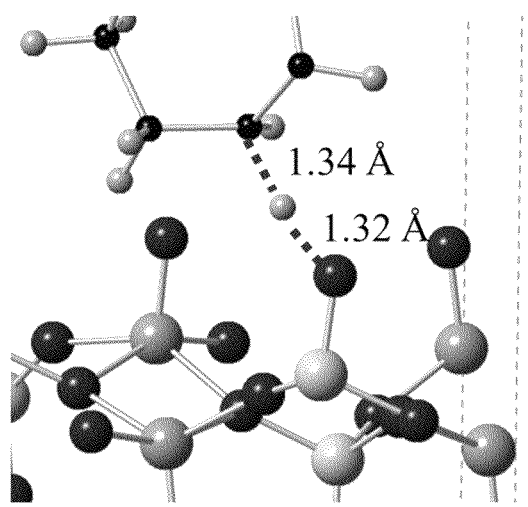
FIG. 34 shows transition state structure for the first n-butane C—H cleavage by O═P. The calculated activation barrier is 13.6 kcal/mol.

FIG. 34 shows the translation state calculated for activating butane on the X1 surface of VOPO$_4$. An activation energy of 13.5 kcal/mol was find, which is consistent with the range of experimental results of 12.9 to 23.6 kcal/mol.

Thus it was concluded that O(1)=P on the metastable $X_1$—VOPO$_4$ surface is the active center for initiating the VPO chemistry. This conclusion is in stark contrast to the common assumption that pyrophosphate or phosphate is a linking ligand and catalytically inactive.

The above conclusion is in contrast to all previous speculations of the mechanism based on experimental and theoretical studies, which suggested that the reactive center is either a V—O bond or chemisorbed O$_2$ on vanadium.

Plausibility of the X1 Phase as the Catalytically Significant Phase.

Figure 51:
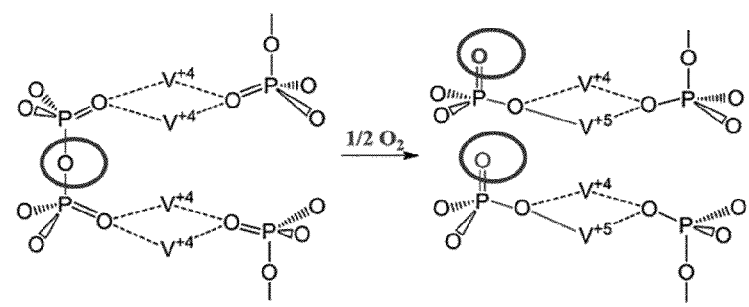
FIG. 51 shows a schematic representation of direct oxidation of $(V+4O)2P2O7$ by O2 involves oxidizing one P2O7 to two PO4, leading directly to the $X1$-$V^{+5}OPO_4$ phase. Converting butane to maleic anhydride converts the surface back to the reduced form.
Figure 51:
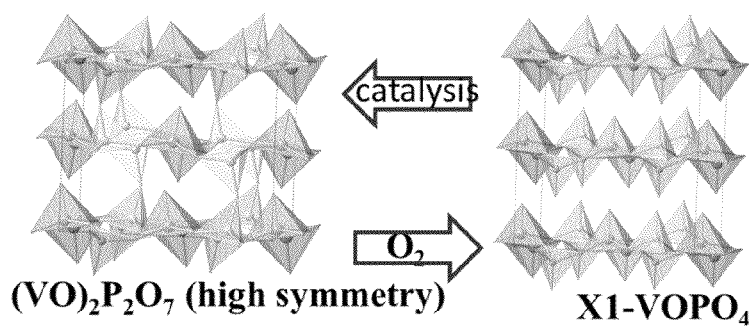

As can be seen in FIG. 51, it can be visualized that the chemistry (reduction and oxidation) is proceeding rapidly in the top view layers where X1 regions catalyze conversion of butane to MA while simultaneously reducing the local region toward the reduced form (VO)$_2$P$_2$O$_7$, which in turn gets reoxidized by O$_2$ to form the X1 phase. Thus, at any one time parts of the top few layers are coupled via pyrophosphate bonds (reduced) while at other times they are oxidized and separated, allowing them to react with butane. It is plausible to the inventors that this dynamic equilibrium with constant conversion between $(VO)_2P_2O_7$ and $X1$-$VOPO_4$ would maintain the oxidized form in the X1 phase because massive atomic rearrangements would be necessary to convert to the other four phases of $VOPO_4$. It is expected that such conversion of X1 into these other phases would lead to catalyst deactivation, requiring a more massive reduction to convert back to $(VO)_2P_2O_7$, which be oxidized by $O_2$ to X1 and then continue the selective catalysis.

Figure 52:
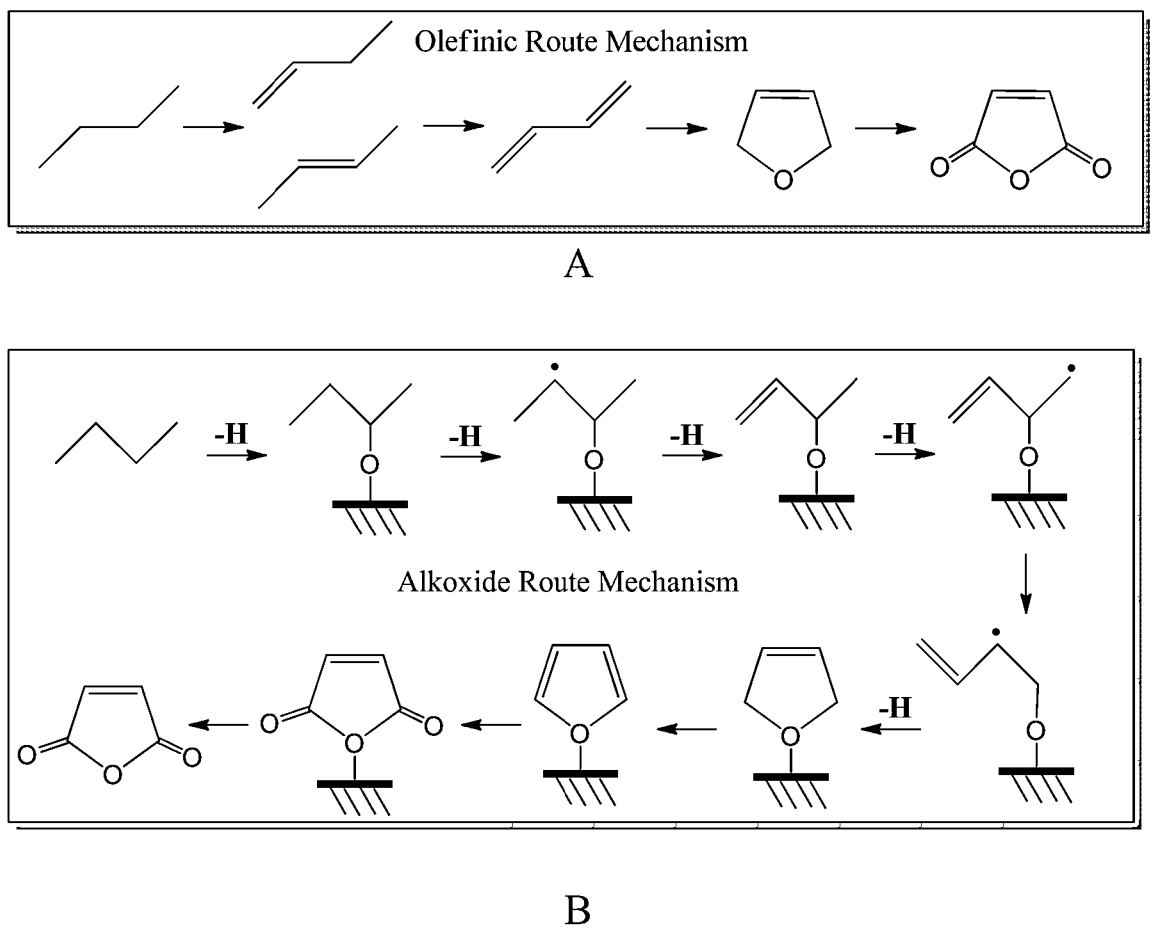
FIG. 52 shows two proposed mechanisms for VPO-catalyzed n-butane to maleic anhydride.

Demonstration that the X1 phase can continue to complete the many reaction steps to form MA product without high activation barriers To demonstrate that the proposed highly reactive surface of $X_1$—$VOPO_4$ is able to convert n-butane all the way to MA, the subsequent steps of this oxidation reaction were studied, considering two mechanisms proposed in the literature (see FIG. 52).

The olefinic route mechanism (FIG. 52A), in which n-butane is first converted to butene, butadiene, dihydrofuran, crotonlactone, and finally MA. The mechanism was established for low pressure conditions by Gleaves using a TAP reactor to determine the intermediates desorbing to the gas phase.

The alkoxide route mechanism (FIG. 52B) in which the intermediates stay on the surface without going into the gas phase. This mechanism is consistent with the high selectivity observed in practice, with little gas phase intermediates observed.

Figure 35:
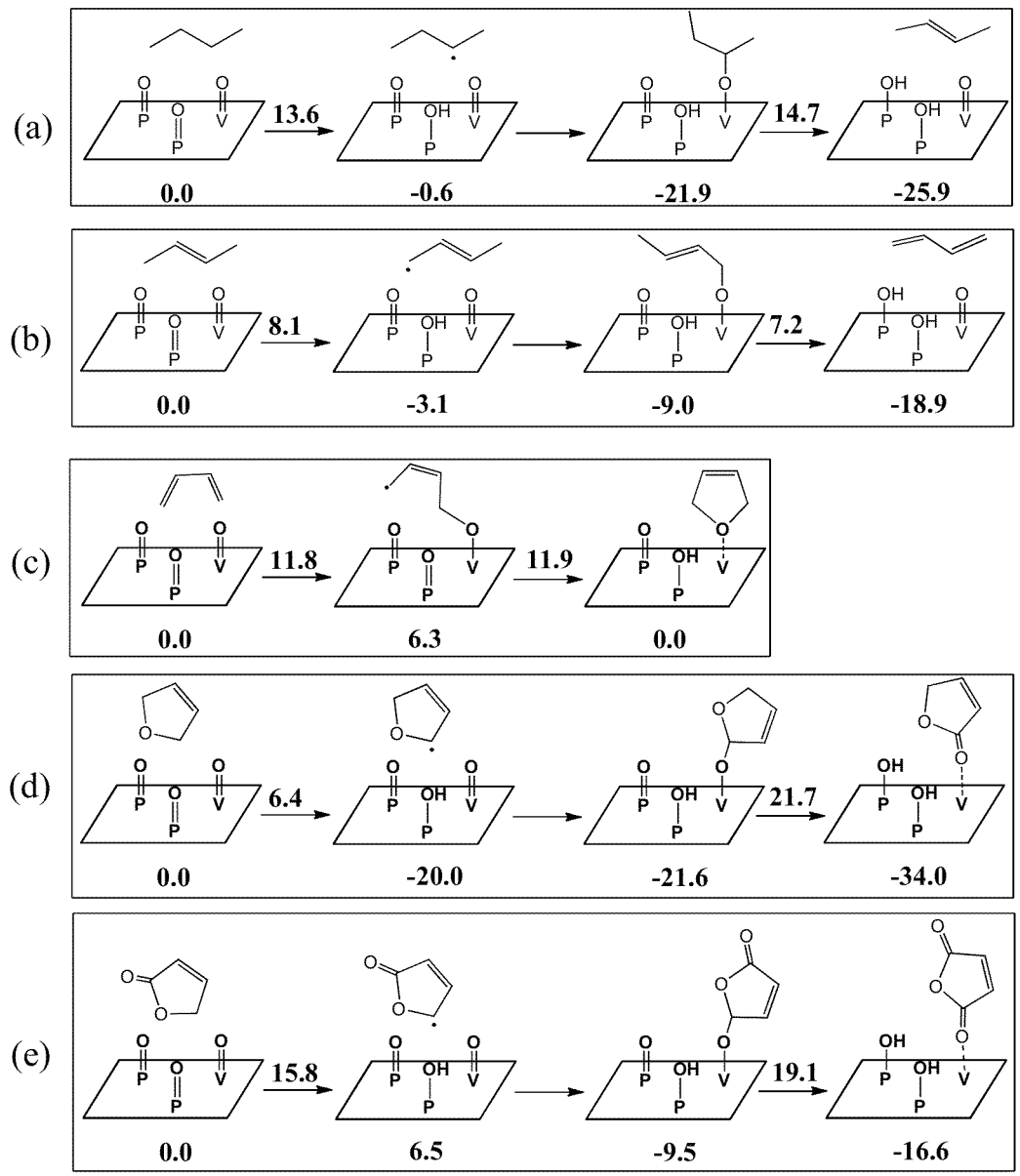
FIGS. 35(a), (b), (c), (d) and (e) show DFT-PBE calculated energetics based on the olefinic-route mechanism. The activation energies are shown above the arrows. Energies in kcal/mol.

The results for the olefinic route mechanism (calculated using a one-layer computational model for the QM calculations) are summarized in FIG. 35. It is found that the highest barrier in the conversion of butane to MA is 21.7 kcal/mol, quite consistent with experiment, which leads to $E_{act}$=12.9 to 22 kcal/mol.

In this reaction sequence, eight surface P=O sites react with the substrate to form eight POH, each reducing one $V^{+5}$=O to $V^{+4}$=O. In addition 3 V=O sites were converted to $V^{+3}$ which in turn reacted with the subsurface $V^{+5}$=O to form $V^{+4}$—O—$V^{+4}$. Thus the net result is to form 14 $V^{+4}$ sites with three V—O—V pairs coupling between the two layers.

It is assumed that subsequent reactions with $O_2$ can recover the oxidized surface states. This overall reaction is summarized in FIG. 35. All steps are consistent with QM (quantum mechanics) and experiment, but there could be other processes as good or better.

Zhang-Lin et al. performed a kinetic study of the oxidation of n-butane, butadiene, and furan catalyzed by VPO. By measuring the reactant conversion rate and MA formation rate from those oxidation reactions, they suggested a direct route from n-butane to MA. In this route, the activated n-butane forms an alkoxide intermediate on the surface and remains covalently bonded with the catalyst surface while all the subsequent oxidations step occur until final MA product release. Importantly, there is no desorption until the final product MA is formed A version of this alkoxide route mechanism proposed by the inventors is in FIG. 36, where Zhang-Lin is depart from by assuming that butadiene can be formed, but reacts rapidly to form a bound 2,5-dihydrofuran. Key assumptions in the proposed mechanism are shown in FIG. 36, namely: hydrogen abstraction by O=P; carbon radical rebound with OH; and hydrogen abstraction by HO—P.

In order to construct the potential energy surface of the proposed mechanism, the following information was needed: the binding energy between O=P and a hydrogen atom, the binding energy between HO—P and a hydrogen atom to form $H_2O$, the energy cost to break off the OH bound to P, and the C—H bond strength and C—OH bond strength of the cyclic intermediates.

Figure 37:
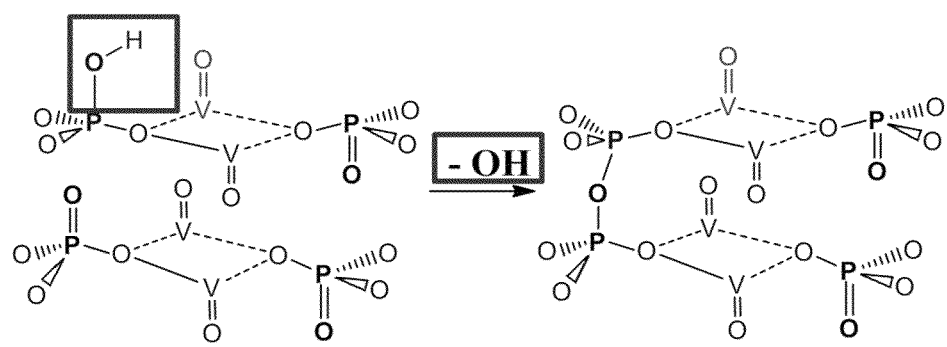
FIG. 37 shows computed P—OH bond strength.

FIG. 37 uses a two layer model in QM calculations to determine the strength of the OP bond at the surface P. It is found that the second layer plays a key role. Instead of leaving a radical on the surface P after removal of the O, the P radical reacts with the P=O bond of a subsurface P to form a pyrophosphate bond and reduces a V in the second layer bridged to the second layer P. As a result of this stabilization, the energy to break the OH from the top P is only 69.7 kcal/mol.

Figure 36:
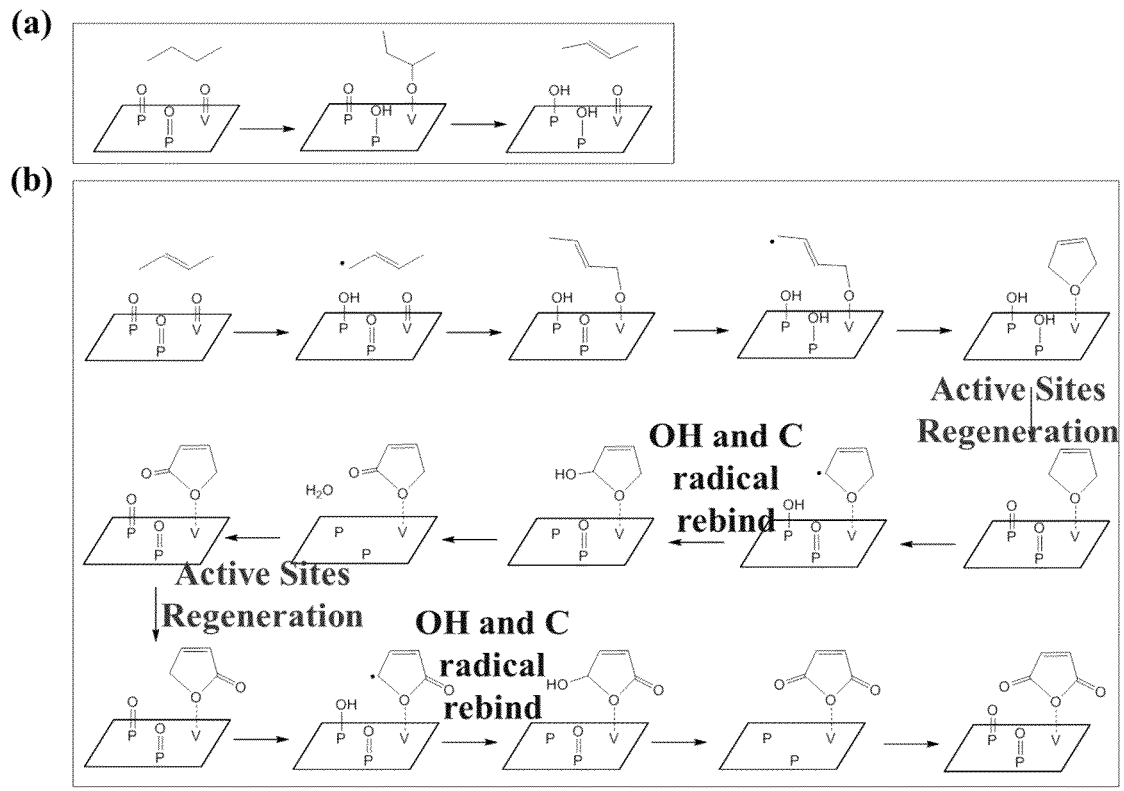
FIGS. 36(a) and (b) show DFT based mechanism following the alkoxide-route.
Figure 38:
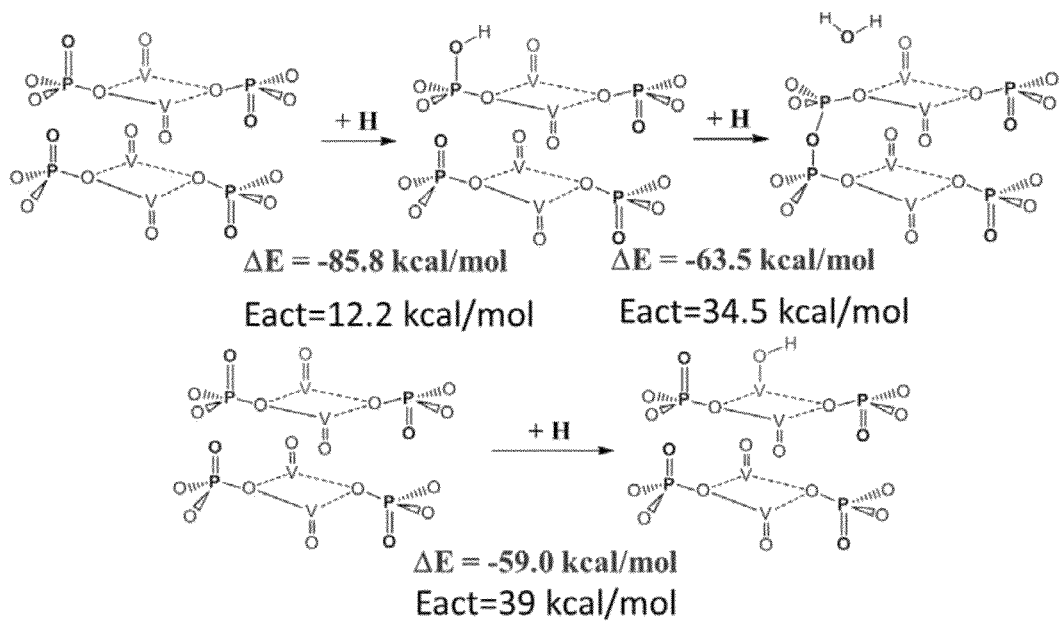
FIG. 38 shows computed O—H Bond Formation Energies (using the PBE-D2 Functional).

FIG. 38 compares the energy for a surface P—OH bond to extract a H to form $H_2O$, while stabilizing the surface P as in FIG. 36. Here it can be seen that forming the H—OH bond is exothermic by only 63.4 kcal/mol (compared to 119 kcal/mol for a free OH), so that surface POH is not expected to activate the alkane C—H bond (unless perhaps aided by allylic stabilization of the substrate). In addition it can be seen that the surface V=O bond is not adequate to activate alkanes.

Figure 39:
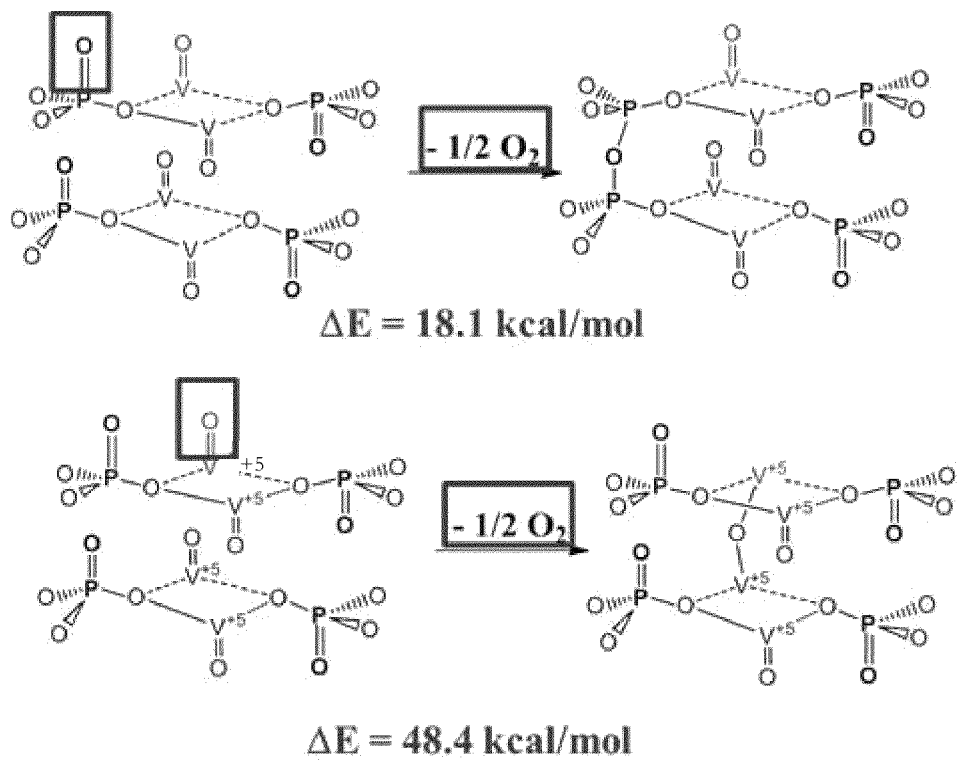
FIG. 39 shows computed Oxygen Vacancy Formation Energies (Two-Layer Model).

FIG. 39 examines how the second layer can stabilize formation of a surface vacancy. This indicates that addition of O into the substrate is more likely to come from P=O rather than V=O. Thus the steps that assume the substrate R forms V—O—R bonds may instead involve P—O—R bonds.

Figure 40:
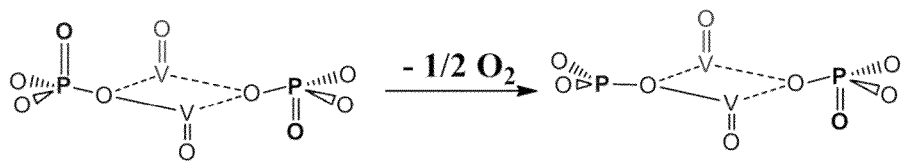
FIG. 40 shows computed Oxygen Vacancy Formation Energies (One-Layer Model). Comparing to the two-layer model these results show that the $2^{nd}$ layer bonding decreases the energy to remove the O (for adding to the product) by 59.0 kcal/mol for O(1)=P and by 20.4 kcal for O(1)=V. This shows the importance of the layer structure for the catalysis in some embodiments herein described.
Figure 40:
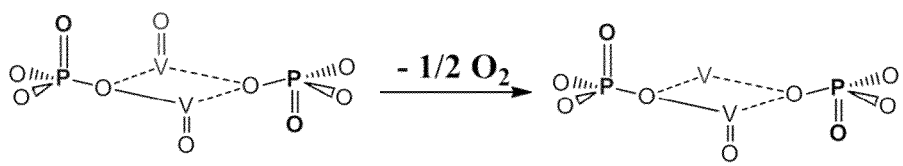

FIG. 40 compares these energetics from the two-layer model with the ones obtained with the one-layer model. Comparing the vacancy formation energy from two-layer and one-layer models, it is computed that the strength of interlayer P—O—P bond, as 59.0 kcal/mol and the V—O—V bond as 20.4 kcal/mol.

Figure 41:
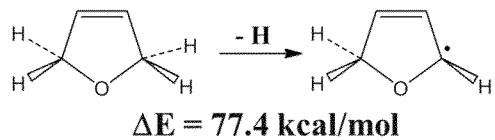
FIG. 41 shows C—H Bond Strength of the Possible Intermediates from DFT-PBE.
Figure 41:
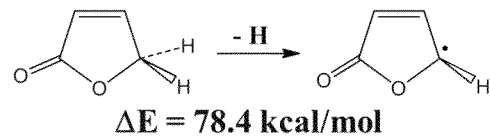
Figure 41:
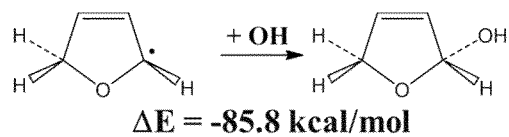
Figure 41:
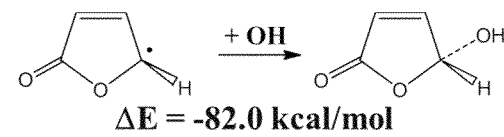
Figure 41:
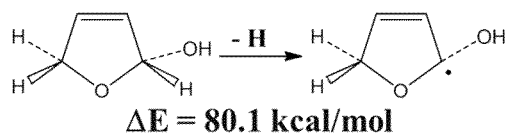
Figure 41:
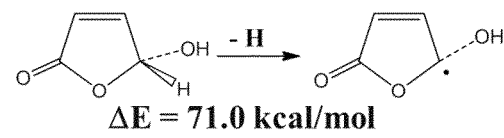
Figure 41:
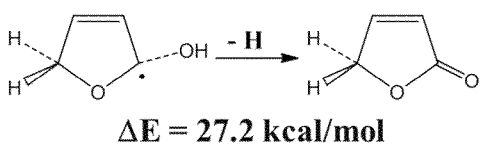
Figure 41:
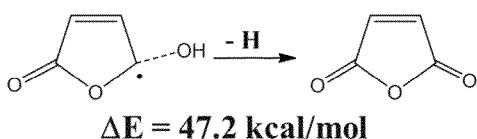

FIG. 41 reports the various bond energies for reactions with the 2,5-dihydrofuran intermediate.

Figure 42:
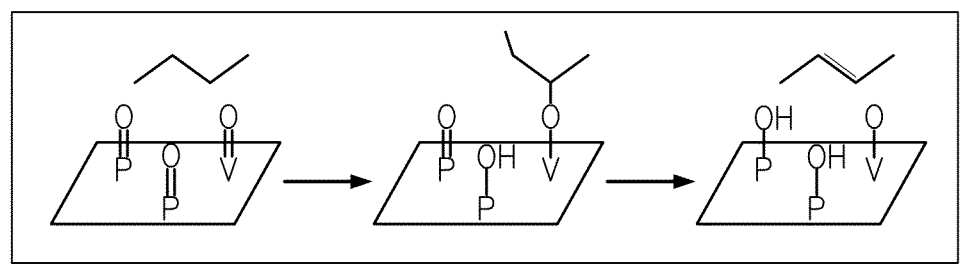
FIG. 42 shows DFT-PBE-calculated potential energy surface based on the alkoxide route mechanism. No activation energies have been calculated, but it is expected that they will be less than 23 kcal/mol, indicating that this mechanism is also compatible with experiment.

Combining these energetics together leads to the results in FIG. 42 for the various steps in the alkoxide route mechanism. Barriers for these steps were have not calculated since the two layer periodic calculations are far more demanding. However given that every step is exothermic by 8 to 42 kcal/mol and the likely barriers are less than 20 kcal/mol for most steps, it is considered that the alkoxide route is plausible with no major issues.

Summary of the ROA Mechanism for VPO Catalytic Selective Oxidation of Butane to MA.

Summarizing, DFT was used to validate that the ROA to explain how the vanadium phosphorus oxide surfaces convert n-butane selectively to MA on. In contrast to all previous suggestions, it was found that surface O(1)=P (formed through the oxidation of pyrophosphate to two ortho-phosphates) is the site that activates n-butane (barrier of 13.5 kcal/mol). This high reactivity of O(1)=P is due to its strong basicity coupled with the large reduction potentials of nearby $V^{+5}$ ions.

A full reaction pathway on this surface for oxidizing n-butane all the way to maleic anhydride, with an overall barrier not exceeding 21.7 kcal/mol was also demonstrated. This is consistent with the reaction proceeding down to 673-723 K.

Thus, the inventors have found that O(1)=P on the $VOPO_4$ surface is the active center for initiating the VPO chemistry, by extracting H from the alkane C—H bonds.

Two complete pathways for the subsequent functionalization of n-butane to maleic anhydride were examined in some detail and found the overall barrier to not exceed 21.7 kcal/mol.

The second layer plays an essential important role in the chemistry. In the reduced form the system forms P—O—P bridges which upon oxidation by gas phase $O_2$ generate the surface P=O bonds that activate the butane. Then in some steps as in FIG. 35 and FIG. 42, reforming the P—O—P bridges to the second layer activates the chemistry at the surface. Similarly O—V—O bridges between the layers may play the role of converting a surface $V^{3+}$ to a $V^{4+}$—O—$V^{4+}$ bridge that activates a step at the surface.

This example considers the VOPO catalyst for the reaction mechanism for the highly selective direct oxidation of n-butane to maleic anhydride by the vanadium phosphate oxide (VPO) catalyst, in which $O_2$ is the oxidant. The inventors have found that the strong C—H bonds of n-butane are activated through a unique mechanism involving the O=P rather than the O=V moieties to cleave the butane C—H bond in a homolytic manner. This is most favorable because the proton transfers to O=P while the electron transfers simultaneously to the neighboring vanadium (which is coupled to the P through oxygen), reducing it from $V^V$ to $V^{IV}$ (FIG. 13(a), M=V, n=5, X=P, Y=Z=O, "H"=H). This PO—H bond is sufficiently strong that the reaction barrier to extract an H from n-butane is less than 14.0 kcal/mol. For the VPO catalyst the butyl radical gets trapped on an adjacent V=O site and subsequent C—H bond breaking occurs through successive activation by additional P=O bonds, eventually producing maleic anhydride.

Activating C—H bonds in this way is expected to decrease the likelihood of unwanted side reactions on the transition metal center, since the metal is not adjacent to the active center. Moreover, the C—H activation power ($D_{PO—H}$, the binding energy of the P=O to a hydrogen atom) of the substrate depends on both the $pK_a$ of the protonated oxo and on the reduction potential of the transition metal [Ref 53], and their separation from each other by two atoms (—PO—) provides some freedom to tune $D_{PO—H}$ for selective activation.

Example 13

Application of the Reduction-Coupled Oxo Activation (ROA) Principle to New Heterogeneous Catalysts for Selective Oxidation: Use of V=O Moieties is Optional In Example 12, 8P=O bonds and 3 V=O bonds were used to complete this complex rearrangement, which ultimately led to reducing 14 V5+ to V4+. However all these steps could have been completed using just P=O bonds, assuming that they were coupled through O to sites, like V+5, that are easily reduced. This suggests that it can now be possible build structures based on this concept to discover completely new catalysts capable of such processes.

Example 14

Application of the Reduction-Coupled Oxo Activation (ROA) Principle for Selective Oxidation to Complex Products: M1 Phase of $MoVNbTeO_x$ as a Propane (Amm)Oxidation Catalyst Overview In this Example it is shown how the ROA principle can explain another very complex reaction, selective (amm)oxidation of propane to acrylonitrile by mixed metal catalysts, MMO, based on $MoVNbTeO_x$. Based on this, the methods and catalysts described herein can be used to improve similar reactions (see Example 17).

For many years very effective catalysts (based on $BiMoO_x$ with many additives) for (amm)oxidation of propene to acrylonitrile have been used to produce of 10 billion pounds of acrylonitrile annually [Ref 54]. A major breakthroughs was made in the 1990's by BP-America [Ref 55] (formerly SOHIO) and Mitsubishi [Ref 56] in discovering catalysts (e.g. $MoVNbTeO_x$) that convert propane (not propene) directly to acrylonitrile.

However these have not yet led to commercially viable catalysts because despite nearly 20 years of experiments the selectivity remains too low. The inventors believe that the essential reason for the lack of progress is that there has not been an atomistic mechanism proposed for how the catalysts works. It has been established that the M1 phase of the $MoVNbTeO_x$ catalyst is responsible for the propane activation step, but it is not known this happens.

Synthetic Procedure

The synthetic procedure is described in [Ref 57]. In short, the catalyst can be prepared by mixing aqueous solutions of $(NH_4)Mo_7O_{24}$, $NH_4VO_3$, and $H_6TeO_6$ with $Nb_2O_5.nH_2O$ dissolved in aqueous oxalic acid and calcining the mixture at 600-650° C. under Ar flow.

Generalized catalysts may be prepared in a similar fashion, with ammonium salts or oxalate complexes of the desired metal oxides.

See example 3, "Computational methods", for computational procedures.

Figure 43:
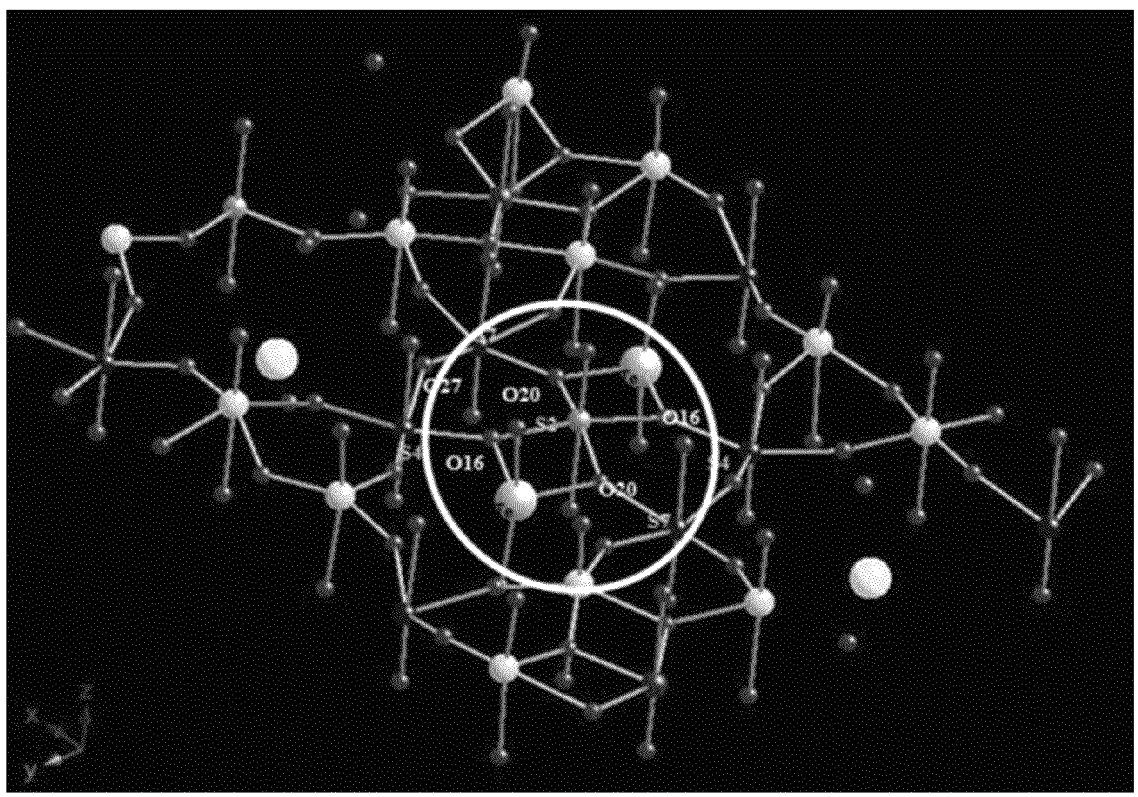
FIG. 43 shows the composition of various sites of the M1 phase from x-ray.
Figure 53:
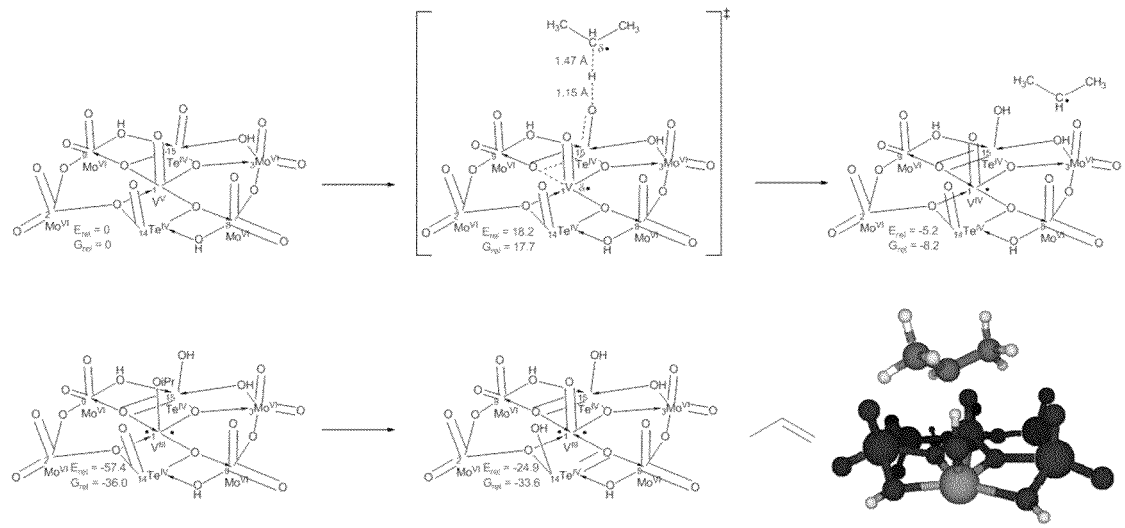
FIG. 53 shows a schematic illustration of a proposed mechanism for the M1 surface to activate propane and convert to propene. The first Te═O extracts the H from propane to form iPr radical which is trapped on a nearby V═O or Mo═O center, perhaps the V═O at site S2. Then the $2^{nd}$ Te═O extracts an H from CH3 to form propene.

Based on the ROA principle the inventors suggest that the sites responsible for activating the CH bond of propane are Te=O bonds coupled through bridging O atoms to $V^V$ and $Mo^{VI}$ sites. These are illustrated in FIG. 43. It will be show below that the site responsible for activating propane and converting it to propene is the site S12 identified in the xray studies to be 70% Te. There are two such Te which are bridged by the S2 site, identified to be 80% V. No one had ever suggested that the Te was responsible. However FIG. 53 shows that this site is quite capable of activating propane and converting to propene with barriers of 100–90=10 kcal/mol.

This propene produced by M1 is widely believed to migrate to the M2 phase, where previous studies concluded that propene is activated by hypervalent Te=O . . . Te=O chains where each Te is bridged via O to either $V^V$ or $Mo^{VI}$.

Example 15

Application of the Reduction-Coupled Oxo Activation (ROA) Principle to Homogenous Catalysts for Selective Oxidation: Homogeneous Organometallic/Inorganic Complexes The methods and catalysts described herein are expected to be useful in designing new organometallic catalysts for alkane C—H activation and functionalization and other related cases.

In particular, it is proposed to have a transition metal atom is bound directly to O=P, so that after hydrogen binds with O=P, the P-M σ-bond becomes a donor-acceptor bond to reduce the metal by one electron. Organometallic complexes featuring such a structure have been synthesized recently [Ref 58-65], but they are not optimal for increased activity. Application of the methods described herein are expected to provide organometallic molecules expected to exhibit activation of alkane C—H bonds with low barriers.

In this Example, the effect of the metallic center on $D_{PO—H}$ was investigated. Considering the trianionic pincer-type phosphinito $[OP(O)O]^{3-}$ group 5 transition metal dichloride complexes (1-V, -Nb, and -Ta, FIG. 41(b) left) in which the metal is in the +5 oxidation state.

$D_{PO—H}$ values of 85.6 (V), 66.0 (Nb), and 59.3 (Ta) kcal/mol were predict. This indicates that the vanadium case is expected to be quite active.

Figure 44:
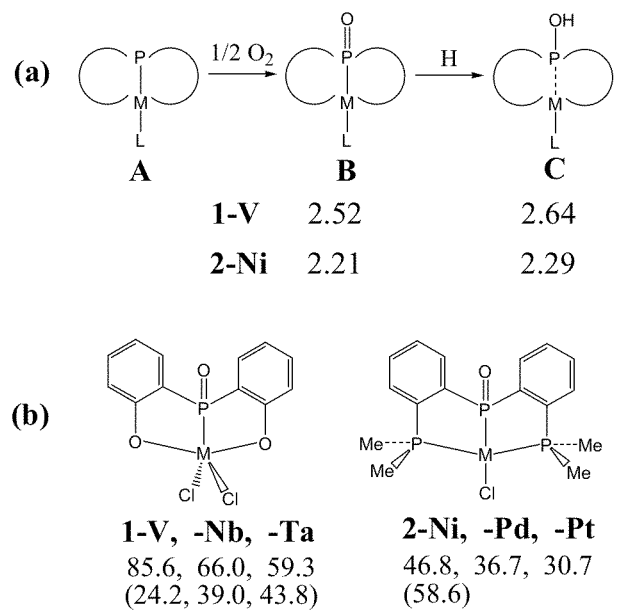
FIG. 44 shows (a) scheme for generating the active molecule B from its precursor A, and its monohydrogenation to C. The number below each species is the M-P bond distance in Å; and (b) The actual structures investigated for group 5 and 10 metals. The number below each species is the $D_{PO—H}$ energy and the reaction barrier ($E_a$) for n-butane methylene C—H bond cleavage (in parentheses) in kcal/mol.

Indeed, it was found that using 1-V to activate n-butane methylene C—H bonds leads to a barrier of $E_a$=24.2 kcal/mol, much lower than that using 1-Nb (39.0 kcal/mol) or 1-Ta (43.8 kcal/mol) (see FIG. 44).

The $D_{PO-H}$'s of the monoanionic pincer-type phosphinito [PP(O)P]$^{1-}$ group 10 transition metal monochloride complexes (2-Ni, -Pd, and -Pt, FIG. 44(b) right), in which the metal is at the +2 oxidation state was also calculated.

This leads to $D_{PO-H}$ values of 46.8 (Ni), 36.7 (Pd), and 30.7 (Pt) kcal/mol, none of which are capable of breaking alkane C—H bonds. This is further supported by the high $E_a$ of 58.6 kcal/mol for 2-Ni.

Methods for synthesizing these complexes [Ref 59-61, 64, 65] or their precursors [Ref 58, 62, 63] (A, FIG. 44(a)) are known, and oxidation of the precursors (A→B) [Ref 61, 64, 65] leads to the target molecules (DFT predicts the reaction energy from A to B to be downhill by 57.3, 58.6, and 59.8 kcal/mol for 2-Ni, -Pd, and -Pt, respectively).

Trends Observed

According to the valence bond description, the M-P bond distance should increase by half a bond order or ~0.1 Å after hydrogen abstraction since it changes from a covalent bond to a donor-acceptor bond. This is consistent with previous calculated results (FIG. 45) showing $R_{M-P}$, values of B at 2.52 and 2.21 Å for 1-V and 2-Ni, respectively, which are lengthened in C to 2.64 and 2.29 Å, respectively Evidently, as the metal changes from a 1$^{st}$- to 2$^{nd}$- to 3$^{rd}$-row transition metal, the $D_{PO-H}$ decreases significantly, with vanadium and nickel representing the best choices of the metallic center for groups 5 and 10, respectively. This trend is believed to be due to the decrease in the reduction potential going down the periodic table, since the role that the metallic ion plays in the hydrogen abstraction is to host the added electron.

The Mulliken analysis shows that the spin density on the metal of the hydrogenated complex C decreases from 1.06 and 0.78 for 1-V and 2-Ni to 0.87 and 0.36 for 1-Nb and 2-Pd, and further to 0.79 and 0.26 for 1-Ta and 2-Pt, indicating that as the metal changes from a 1$^{st}$- to 2$^{nd}$-, to 3$^{rd}$-row transition metal, its reduction potential decreases. Moreover, calculations show that group 5 early transition metals possesses a much larger $D_{PO-H}$ (and as a result a lower $E_a$) than does group 10 of late transition metals, clearly indicating that it is more beneficial to have an early transition metal with a high oxidation state as the metallic center.

Figure 45:
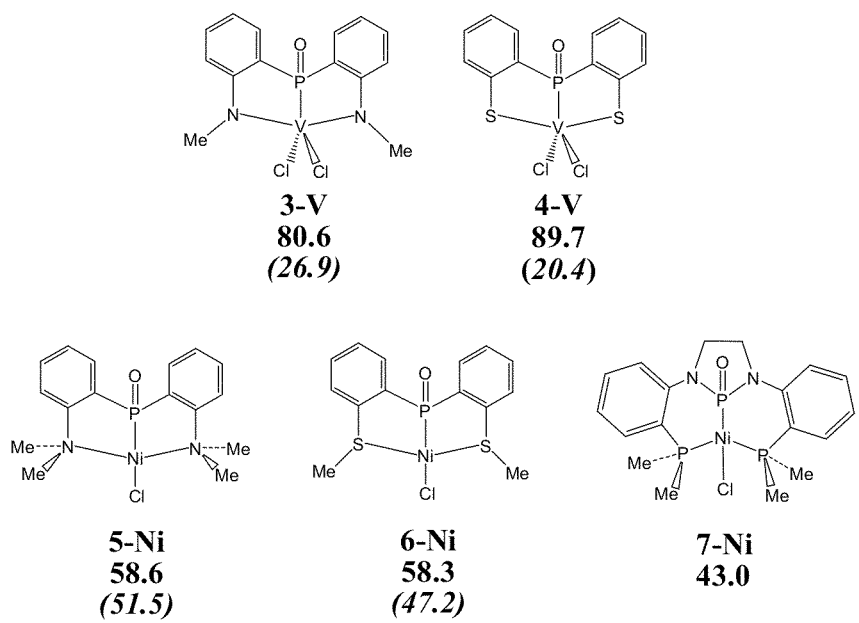
FIG. 45 shows proposed early and late transition metal complexes for evaluating the C—H activation power. The numbers below the notations are $D_{PO—H}$ values and $E_a$ values in parentheses.

The influence of organic ligands on $D_{PO-H}$ was then studied. Two additional ligands were chosen for vanadium (FIG. 45).

$D_{PO-H}$=80.6 and $E_a$=26.9 kcal/mol for 3-V, and $D_{PO-H}$=89.7 and $E_a$=20.4 kcal/mol for 4-V were predict. For the nickel complexes, $D_{PO-H}$=58.6, 58.3 and 43.0 kcal/mol for 5-Ni, 6-Ni, and 7-Ni, and $E_a$=51.5 and 47.2 kcal/mol for 5-Ni and 6-Ni, respectively, were predict.

Figure 46:
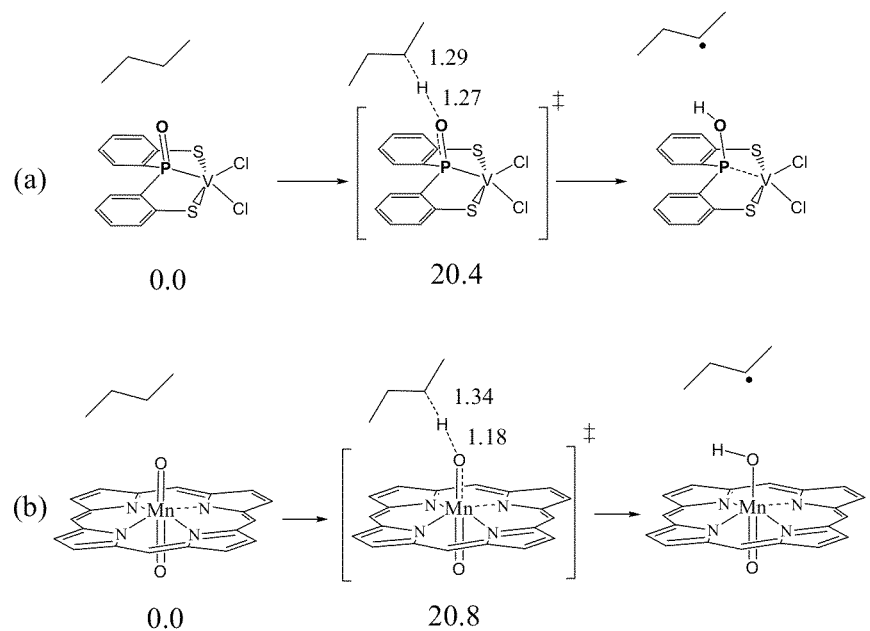
FIG. 46 shows potential energy surface of using (a) 4-V and (b) the Mn dioxo porphyrin complex to activate n-butane secondary C—H bonds. Energies are in kcal/mol, and bond distances are in Å.
Figure 47:
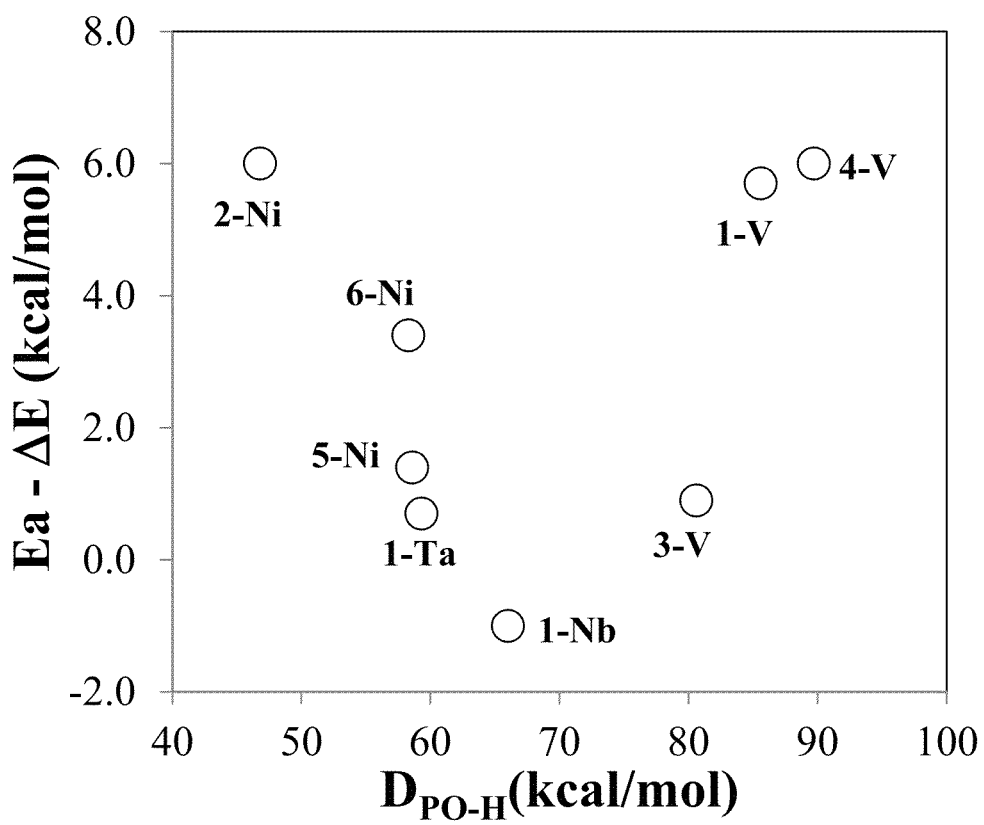
FIG. 47 shows illustrates that a rapid assay for good catalysts can focus on $D_{PO—H}$. This shows that magnitude of the barrier height above the reaction energy, $\Delta E = D_{C—H} - D_{PO—H}$, is between −1 and +6 kcal/mol.

Thus, the vanadium complexes appear to be more favorable for cleaving C—H bonds than the nickel complexes. Nevertheless, it was found the replacement of the [PP(O)P] ligand significantly affects $D_{PO-H}$ as well as $E_a$ Next the $E_a$ of 4-V was compared to that of the Mn$^V$ trans-dioxo porphyrin complex (FIG. 46), a known catalyst for alkane C—H activation [Ref 37].

The two barriers were found to be nearly identical (20.4 versus 20.8 kcal/mol). This suggests that the C—H activation ability of the molecules proposed in this study is similar to that of existing catalysts.

Figure 54:
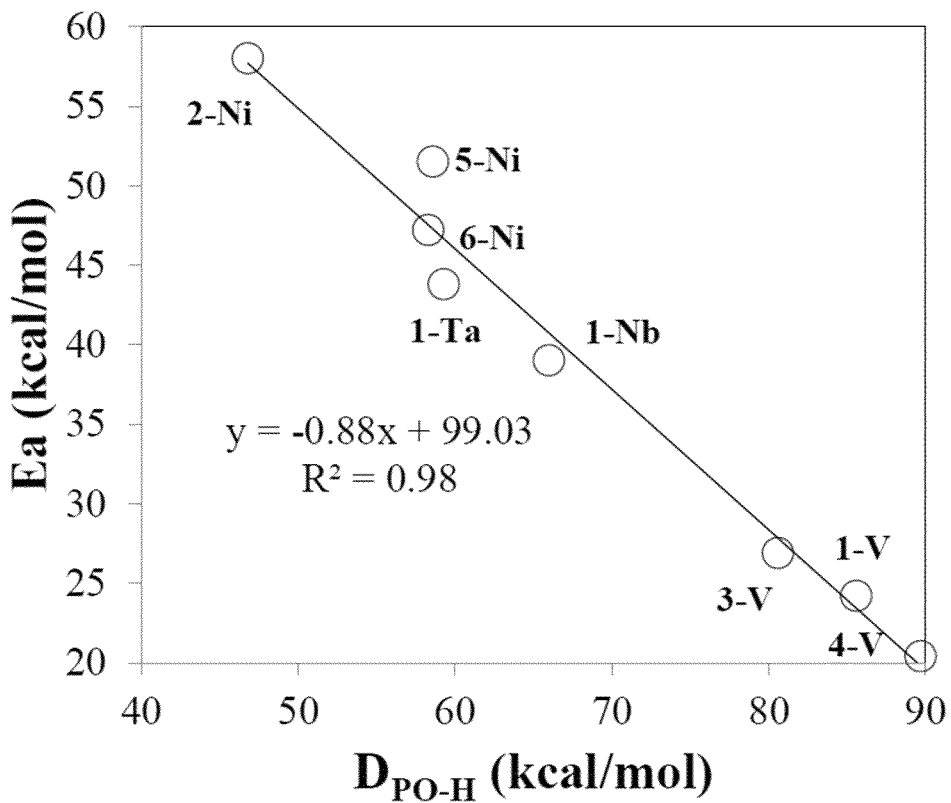
FIG. 54 shows calculated C—H activation barriers for various organometallic complexes calculated according to methods herein described.

As expected the calculated C—H activation barriers correlate well with $D_{PO-H}$ ($R^2$=0.98) (FIG. 54). This suggests that C—H activation barriers of this type of organometallic complexes can be estimated accurately by their $D_{PO-H}$'s The C—H activation power of these proposed molecules can be further increased by using those high oxidation state metals having the largest reduction potentials. This is expected to be accomplished by modifying the organic ligand to make the metal more electron-deficient. Another way expected to enhance the C—H activation ability is to replace O═P with other motifs with higher basicity, such as RN═P See example 3, "Computational methods", for computational procedures.

These complexes can be synthesized by methods for synthesizing similar complexes known to a skilled person. For examples on ligand synthesis see, e.g. [Ref 66, 67]. For examples on metal installation see, e.g. [Ref 68-71] Kurmaev et al. *Inorg. Chim. Acta* 2013, 396, 136; Villanneau et al. *Eur. J. Inorg. Chem.* 2013, 1815; Tong et al. *Inorg. Chim. Acta* 2012, 383, 91; North et al. *Tetrahedron: Asymmetry* 2012, 23, 1218.

New Example 16

Construct Model (i.e. Construct Specific Example of Formula (II))

First, X, Y, Z, M are selected.

A is designed in such a way that typical bond lengths, angles, and valences of Y1=X-Z-M=Y2 (if Z and Y2 chosen) core is preserved, and that the overall charge is neutral, where by "typical" it is meant numbers readily referenced by any introductory chemistry textbook.

For examples, see Examples 4-10 above.

The general principle is to attach additional oxos to M as necessary to bring it to maximum valence, Z linkers to M and X, and additional M and or X to bridge the additional Z linkers (with the choice depending on the parity of the valences of M and X)

Thev the molecule's initial guess geometry is constructed using Cartesian coordinates or Z-matrix using typical bond lengths and angles.

As an example of an initial guess, see example 4 FIG. 17d, $PV_3O_{10}$. Z-matrix:

P1
O2 P1 1.43
O3 P1 1.60 O2 116.2
O4 P1 1.60 O2 116.2 O3 120
O5 P1 1.60 O2 116.2 O3 −120
V6 O3 1.60 P1 130.3 O2 180
V7 O4 1.60 P1 130.3 O2 180
V8 O5 1.60 P1 130.3 O2 180
O9 V6 1.60 O3 116.2 P1 180
O10 V7 1.60 O4 116.2 P1 180
O11 V8 1.60 O5 116.2 P1 180
O12 V6 2.00 O3 102.0 P1 60
O13 V7 2.00 O4 102.0 P1 60
O14 V8 2.00 O5 102.0 P1 60

First Calculation on Model:

An initial energy calculation is performed, and then the geometry is optimized

Initial Energy Calculation on Model

A basis set is chosen, as are pseudopotential (if necessary) and method. Keywords are basis and dftname.

As an example, LACVP basis set/pseudopotential[1] (6-31G basis set for light atoms[2]), and B3LYP-D3 (a hybrid DFT[3] with dispersion correction[4]) can be used as the method, although other combinations (for example LACV3P**++ and M06) could be used as well.

Geometry optimization (keyword igeopt) requires initial Hessian matrix; as an example a Schlegel Hessian [Ref 25] can be generated, although others could be used as well.

A sample input deck (this is for the Jaguar 7.9 software package) is:
&gen
basis=lacvp**
dftname=b3lyp-d3
igeopt=1
&

The output comprises a) the mostly optimized geometry of the model system, and b) the electronic wavefunction.

Second Calculation on Model:

Using the output of the first calculation, the parameters are adjusted to get a finer optimization of the geometry, and to calculate the frequencies in order to ensure that a thermodynamic minimum has been found.

The geometry optimization in the first calculation is fast but coarse. A finer optimization can then performed by using Cartesian coordinates (keyword intopt), adjusting the trust radius using Culot/Fletcher heuristic [Ref 72] (keyword itradj), and restricting the maximum allowed trust radius (keyword tradmx). An ultrafine grid (keyword gdftgrad) can be used for highest accuracy.

Frequencies (keyword ifreq) may be calculated analytically using the second derivatives of the energy of the system versus various coordinate perturbations (Coupled perturbed Hartree-Fock equations, CPHF [Ref 73]). An ultrafine grid (keyword gdftcphf) was used for highest accuracy. The number of CPHF iterations (keyword maxitcp) may be increased if necessary to ensure convergence.

A sample input deck (this is for the Jaguar 7.9 software package) is:
&gen
basis=lacvp**
dftname=b3lyp-d3
igeopt=1
intopt=0
itradj=1
tradmx=0.08
gdftgrad=-13
ifreq=1
gdftcphf=-13
maxitcp=200
&

The calculated frequencies of the output should be checked to ensure that all frequencies are positive—this ensures that the model's final structure is geometrically an energy minimum. Sometimes the geometry optimization may not be fully successful and one or two small negative frequencies remain. In this case, the following strategies may be employed:

Tightening geometry convergence parameters: adding the following to the input deck. The parameters may be further tightened as necessary.
gconv1=0.0003
gconv2=0.0002
gconv5=0.0012
gconv6=0.0008

Traveling forward and backward along the negative frequency.

The energy of the model system may now be extracted.

Monohydrogenated Model Procedures

A monohydrogenated model is constructed, with the hydrogen bound to the catalytic site, starting with final geometry of model system acquired above. By adding the extra hydrogen 1 Å from Y; H—Y—X angle 180° (done to avoid having to specify a H—Y—X—Z dihedral).

A first calculation on monohydrogenated model is performed as was performed with the non-hydrogenated model. The geometry optimization algorithm will automatically adjust the H—Y—X angle to a more physical number and the H—Y—X—Z dihedral to its proper value.

A second calculation on monohydrogenated is performed as was performed with the non-hydrogenated model. The energy of the monohydrogenated model system may now be obtained.

Determination of Y1-H Bond Enthalpy

The energy difference between the monohydrogenated model and its plain version is the measure $D_H$ of activation ability.

Example 17

As an example, the ammoxidation of propane to acrylonitrile is proposed as a reaction using the catalysts and methods described herein. In particular, such a transformation is expected to be accomplished using a catalytic matrix as described herein, where the catalytic matrix comprises several catalytic cores, as described herein.

Specifically, the reaction is $C_3H_8+1.5O_2 \rightarrow C_3H_4O+2H_2O$ or $C_3H_8+2O_2+NH_3 \rightarrow C_3H_3N+4H_2O$, respectively. This transformation may be broken down into three steps:

Activation of propane: $C_3H_8+cat^1 \rightarrow C_3H_7.+cat^1H$, which ultimately leads to dehydrogenation to form propylene: $C_3H.+cat^1 \rightarrow C_3H_6+cat^1H$ ($cat^1$ is a first catalytic core);

Activation of propylene: $C_3H_6+cat^2 \rightarrow C_3H_5.+cat^2H$, which creates an ally radical $C_3H_5.$ ($cat^2$ is a second catalytic core);

Adsorption of allyl radical and further oxidation to the final products: $C_3H_5.+cat^3 \rightarrow C_3H_5cat^3 \rightarrow \rightarrow C_3H_4O$ or $C_3H_3N$.

In this case, for the first step (activation of propane) the first catalytic core should have sufficient strength to activate propane (BDE ~100 kcal/mol); for the second step (activation of propylene) the second catalytic core should have sufficient strength to active propylene (BDE ~88 kcal/mol), and for the third step (adsorption of allyl radical and further oxidation to the final products) the catalyst does not require a catalytic core as herein described, but should have a metal such at Mo bonded to an O or an NH, such as Mo=O or Mo=NH, which after several steps can form $C_3H_4O$ or $C_3H_3N$.

For the first catalytic core, Y1=O, X=Te, M=V, Y2=O; i=j=k=1. Such a catalytic core is based on the model system of example 8, in which the model system with the same parameters has a very large DH of 100 kcal/mol.

For the second catalytic core, Y1=O, X=Te, M=Mo, Y2=O; i=1 or 2, j=1, k=2. Such a catalytic core is based on the model system of example 10, in which the model system with the same parameters has a smaller DH of 68-86 kcal/mol, depending on i.

For such a catalytic matrix of the type described above, the layers should be structured in such a way to maximize selectivity and yield. Towards this end, the initial substrate, propane, which is the hardest to activate, should be exposed to the first catalytic core only briefly so as to minimize the potential for unwanted side reactions (which can arise when the step 1 product, propylene, continues to react with core 1 instead of moving onto core 2). Therefore there should be an orderly flow of substrate and intermediates from an initial region contain catalytic core 1 to second region with core 2 and ultimate to the final region containing core 3.

Such a configuration of a catalytic matrix to accomplish the above transformations with the maximized yield and selectivity can be accomplished by configuring the catalytic matrix to have between 0.1 and 10% of the first catalytic core (to prevent excess reaction with the propene or allyl products), between 10 and 50% of the second catalytic core (enough such that the propene reacts with the second core before encountering a second presentation of the first core), at least 40% of the third catalytic core (enough such that the allyl will find one of the third core before encountering a second presentation of the second core).

A skilled person will realize, upon a reading of the present disclosure, that the above method can be generalized to other reactions. The method can be generalized by determining the R—H bond enthalpies of the R—H bonds to be activated at various steps of a chemical transformation, and selecting appropriate elements and/or functional groups for the catalytic cores to provide Y1-H bond enthalpies equal or less than the respective R—H bond enthalpies.

In summary, in several embodiments, described herein are methods for providing catalysts and in particular to methods for providing bond activation catalysts and related catalysts, matrices, systems, and methods.

The examples set forth above are provided to give those of ordinary skill in the art a complete disclosure and description of how to make and use the embodiments of the catalyst, and related, compositions, methods and systems of the disclosure, and are not intended to limit the scope of what the Applicants regard as their disclosure. Modifications of the above-described modes for carrying out the disclosure can be used by persons of skill in the art, and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting.

The term "alkyl" as used herein refers to a linear, branched, or cyclic saturated hydrocarbon group typically although not necessarily containing 1 to about 10 carbon atoms, preferably 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 6 carbon atoms. The term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "heteroatom-containing" as in a "heteroatom-containing alky group" refers to a alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "alkylamino" as used herein intents an alkyl group bound through a single amine linkage, wherein the amine nitrogen can have an optional additional substituent.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "arylamino" as used herein intents an aryl group bound through a single amine linkage, wherein the amine nitrogen can have an optional additional substituent.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

The term "polyether" as used herein indicates a structure containing multiple carbon-oxygen-carbon covalent linkages.

The term "olefins" as used herein indicates two carbons covalently bound to one another that contain a double bond ($sp^2$-hybridized bond) between them. The other functional groups bound to each of these two carbons can be additional carbons, hydrogen atoms, or heteroatoms.

By "substituted" as in "substituted alkyl," "substituted aryl," and the like, as alluded to in some of the aforementioned definitions, is meant that in the, alkyl, aryl, or other moiety, at least one hydrogen atom bound to a carbon (or other) atom is replaced with one or more non-hydrogen substituents.

Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano (—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$), phospho (—PO$_2$), phosphino (—PH$_2$), silyl (—SiR$_3$ wherein R is hydrogen or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

The term "distal" as used herein indicates substitution in the para-position (aryl rings), or at the farthest possible point of attachment from the point of origin (cyclic alkyl ring).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken line indicates that the group in question is below the general plane of the molecule as drawn, and a bond indicated by a bold line indicates that the group at the position in question is above the general plane of the molecule as drawn.

The term "carbon chain" as used herein indicates a linear or branched line of connected carbon atoms.

A same identifier in one or more formulas is intended to identify the same chemical entity, such as elements groups and moieties, unless indicated otherwise. For example, if identifier X is intended to identify X in Formula (II) as "a column 15 or column 16 element capable of forming a double bond to Y1", use of identifier X in a same or other formula should be intended to cover "a column 15 or column 16 element capable of forming a double bond to Y1" unless indicated otherwise As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Ballarini, N., et al., "VPO catalyst for n-butane oxidation to maleic anhydride: A goal achieved, or a still open challenge?" *Topics in catalysis* 2006 38(1-3): 147-156.
2. Hodnett, B. K., "Heterogeneous catalytic oxidation: fundamental and technological aspects of the selective and total oxidation of organic compounds". 2000: Wiley New York.
3. Centi, G., et al., "Mechanistic aspects of maleic anhydride synthesis from C4 hydrocarbons over phosphorus vanadium oxide." *Chemical Reviews* 1988 88(1): 55-80.
4. Cheng, M. J., et al., "The magnetic and electronic structure of vanadyl pyrophosphate from density functional theory." *Phys Chem Chem Phys* 2011 13(20): 9831-9838.
5. Thompson, D. J., et al., "Modelling the active sites in vanadyl pyrophosphate." *Journal of Molecular Catalysis A: Chemical* 2003 198(1): 125-137.
6. Haras, A., et al., "Changes of local electronic structure of perfect $(VO)_2 P_2 O_7$(100) surface in response to oxygen vacancy formation: effect of electron trapping." *Surface science* 2002 513(2): 367-380.
7. Robert, V., et al., "Role of mixed-valence state in vanadium phosphates catalysts." *Journal of Molecular Catalysis A: Chemical* 1997 119(1): 327-333.
8. Schioett, B., et al., "Formation of maleic anhydride on a vanadyl pyrophosphate surface: a theoretical study of the mechanism." *The Journal of Physical Chemistry* 1991 95(6): 2297-2307.
9. Gleaves, J., et al., "Temporal analysis of products (TAP)—a unique catalyst evaluation system with submillisecond time resolution." *Catalysis Reviews Science and Engineering* 1988 30(1): 49-116.
10. Zhanglin, Y., et al., "On the Mechanism of *n*-Butane Oxidation to Maleic Anhydride on VPO Catalysts: I. A Kinetics Study on a VPO Catalyst as Compared to VPO Reference Phases." *Journal of Catalysis* 1994 145(2): 256-266.
11. Agaskar, P. A., et al., "A molecular level mechanism of n-butane oxidation to maleic anhydride over vanadyl pyrophosphate." *Catalysis letters* 1994 23(3-4): 339-351.
12. Tran, T., et al., "Differing Reactions of Functionalized Hydrocarbons with Cp* M (NO)(alkyl)(η3-allyl) Complexes of Molybdenum and Tungsten." *Organometallics* 2011 30(4): 738-751.
13. Blanksby, S. J., et al., "Bond dissociation energies of organic molecules." *Acc Chem Res* 2003 36(4): 255-263.
14. Volta, J.-C., "Dynamic processes on vanadium phosphorous oxides for selective alkane oxidation." *Catalysis today* 1996 32(1): 29-36.
15. Hutchings, G. J., et al., "Role of the product in the transformation of a catalyst to its active state." *Nature* 1994 368(6466): 41-45.
16. Shimoda, T., et al., "Preparation of Vanadium-Phosphorus Mixed Oxide (P/V=1) Catalysts and Their Application to Oxidation of Butane to Maleic Anhydride." *Bulletin of the Chemical Society of Japan* 1985 58(8): 2163-2171.

17. Koyano, G., et al., "Structural Changes of Surface Layer of Vanadyl Pyrophosphate Catalysts by Oxidation—Reduction and Their Relationships with Selective Oxidation of n-Butane." *Journal of the American Chemical Society* 1998 120(4): 767-774.

18. Perdew, J. P., et al., "Generalized gradient approximation made simple." *Physical review letters* 1996 77(18): 3865.

19. Vanderbilt, D., "Soft self-consistent pseudopotentials in a generalized eigenvalue formalism." *Phys Rev B Condens Matter* 1990 41(11): 7892-7895.

20. Monkhorst, H. J., et al., "Special points for Brillouin-zone integrations." *Physical Review B* 1976 13(12): 5188-5192.

21. Henkelman, G., et al., "Improved tangent estimate in the nudged elastic band method for finding minimum energy paths and saddle points." *The Journal of Chemical Physics* 2000 113(22): 9978.

22. Henkelman, G., et al., "A climbing image nudged elastic band method for finding saddle points and minimum energy paths." *The Journal of Chemical Physics* 2000 113 (22): 9901.

23. Saito, T., et al., "Single Crystal Growth of the High Pressure Phase of (VO)2P2O7 at 3 GPa." *Journal of Solid State Chemistry* 2000 153(1): 124-131.

24. Geupel, S., et al., "Synchrotron-radiation study of the two-leg spin ladder (VO)2P2O7 at 120 K. Erratum." *Acta Crystallographica Section C Crystal Structure Communications* 2002 58(4): e10-e10.

25. Grimme, S., "Semiempirical GGA-type density functional constructed with a long-range dispersion correction." *J Comput Chem* 2006 27(15): 1787-1799.

26. Hehre, W. J., "Self-Consistent Molecular Orbital Methods. XII. Further Extensions of Gaussian-Type Basis Sets for Use in Molecular Orbital Studies of Organic Molecules." *The Journal of Chemical Physics* 1972 56(5): 2257.

27. Francl, M. M., "Self-consistent molecular orbital methods. XXIII A polarization-type basis set for second-row elements." *The Journal of Chemical Physics* 1982 77(7): 3654.

28. Hay, P. J., et al., "Ab initio effective core potentials for molecular calculations. Potentials for K to Au including the outermost core orbitals." *The Journal of Chemical Physics* 1985 82(1): 299.

29. Busca, G., et al., "Surface acidity of vanadyl pyrophosphate, active phase in n-butane selective oxidation." *The Journal of Physical Chemistry* 1986 90(7): 1337-1344.

30. Yin, X., et al., "Reactivity of lattice oxygens present in V2O5 (010): A periodic first-principles investigation." *The Journal of Physical Chemistry B* 1999 103(8): 1263-1269.

31. Calatayud, M., et al., "Reactivity of the oxygen sites in the V2O5/TiO2 anatase catalyst." *The Journal of Physical Chemistry B* 2004 108(40): 15679-15685.

32. Lide, D. R., "CRC handbook of chemistry and physics". 2011: CRC press.

33. Schuurman, Y., et al., "Activation of vanadium phosphorus oxide catalysts for alkane oxidation. The influence of the oxidation state on catalyst selectivity." *Industrial & engineering chemistry research* 1994 33(12): 2935-2941.

34. Kung, H. H., "Desirable catalyst properties in selective oxidation reactions." *Industrial & engineering chemistry product research and development* 1986 25(2): 171-178.

35. Joly, J., et al., "TPD study of labile oxygen on a (VO) 2P2O7 catalyst active in n-butane partial oxidation." *Applied Catalysis A: General* 1998 169(1): 55-63.

36. Ballhausen, C. J., et al., "The electronic structure of the vanadyl ion." *Inorganic Chemistry* 1962 1(1): 111-122.

37. Jin, N., et al., "Trans-dioxo manganese(V) porphyrins." *J Am Chem Soc* 2007 129(41): 12416-12417.

38. Wachs, I. E., et al., "In situ Raman spectroscopy studies of bulk and surface metal oxide phases during oxidation reactions." *Catalysis today* 1996 32(1): 47-55.

39. Wachs, I. E., et al., "Fundamental studies of butane oxidation over model-supported vanadium oxide catalysts: Molecular structure-reactivity relationships." *Journal of Catalysis* 1997 170(1): 75-88.

40. Coulston, G. W., et al., "The Kinetic Significance of V5 in n-Butane Oxidation Catalyzed by Vanadium Phosphates." *Science* 1997 275(5297): 191-193.

41. Xue, Z.-Y., et al., "In Situ Laser Raman Spectroscopy Studies of VPO Catalyst Transformations." *The Journal of Physical Chemistry B* 1999 103(44): 9459-9467.

42. Guliants, V., et al., "Evolution of the active surface of the vanadyl pyrophosphate catalysts." *Catalysis letters* 1995 32(3-4): 379-386.

43. Ganduglia-Pirovano, M. V., et al., "Role of ceria in oxidative dehydrogenation on supported vanadia catalysts." *J Am Chem Soc* 2010 132(7): 2345-2349.

44. Alptekin, G. O., et al., "Methane partial oxidation by unsupported and silica supported iron phosphate catalysts: Influence of reaction conditions and co-feeding of water on activity and selectivity." *Journal of Catalysis* 1999 181(1): 104-112.

45. Marcu, I.-C., et al., "Effects of the method of preparing titanium pyrophosphate catalyst on the structure and catalytic activity in oxidative dehydrogenation of <i> n</i>- butane." *Journal of Molecular Catalysis A: Chemical* 2003 203(1): 241-250.

46. Arnold III, E. W., et al., "Effect of water vapor on the activity and selectivity characteristics of a vanadium phosphate catalyst towards butane oxidation." *Applied catalysis* 1988 41: 225-239.

47. Hutchings, G. J., "Promotion in heterogeneous catalysis: a topic requiring a new approach?" *Catalysis letters* 2001 75(1-2): 1-12.

48. Shilov, A. E., et al., "Activation of CH bonds by metal complexes." *Chemical Reviews* 1997 97(8): 2879-2932.

49. Dietl, N., et al., "Room-Temperature C—H Bond Activation of Methane by Bare [P4O10].+." *Angewandte Chemie International Edition* 2009 48(26): 4861-4863.

50. de Petris, G., et al., "Methane Activation by Metal-Free Radical Cations: Experimental Insight into the Reaction Intermediate." *Chemistry—A European Journal* 2009 15(17): 4248-4252.

51. Kubias, B., et al., "The reaction network of the selective oxidation of n-butane on (VO)<sub> 2</sub> P<sub> 2</sub> O<sub> 7</sub> catalysts: Nature of oxygen containing intermediates." *Catalysis today* 1996 32(1): 243-253.

52. Pepera, M. A., et al., "Fundamental study of the oxidation of butane over vanadyl pyrophosphate." *Journal of the American Chemical Society* 1985 107(17): 4883-4892.

53. Gardner, K. A., et al., "Understanding CH bond oxidations: H. and H-transfer in the oxidation of toluene by permanganate." *Science* 1995 269(5232): 1849-1851.

54. Grasselli, R. K., et al., "Multifunctionality of active centers in (amm)oxidation catalysts: from Bi—Mo—O-x to Mo—V—Nb-(Te, Sb)—O-x." *Topics in Catalysis* 2003 23(1-4): 5-22.

55. Wang, C. M., et al., "Neutral nickel(II)-based catalysts for ethylene polymerization." *Organometallics* 1998 17(15): 3149-3151.

56. Ushikubo, T., et al. U.S. Pat. No. 5,281,745,
57. Li, X., et al., "Improvement of the Structural Model for the M1 Phase Mo—V—Nb—Te—O Propane (Amm)oxidation Catalyst." *Topics in Catalysis* 2011 54(10-12): 614-626.
58. Bauer, R. C., et al., "Pincer ligands with an all-phosphorus donor set: subtle differences between rhodium and palladium." *Dalton Trans.* 2011 40(35): 8822-8829.
59. Derrah, E. J., et al., "Original phenyl-P(0) bond cleavage at palladium(0): a combined experimental and computational study." *Chem. Commun.* 2011 47(30): 8611-8613.
60. Derrah, E. J., et al., "Chelating Assistance of P—C and P—H Bond Activation at Palladium and Nickel: Straightforward Access to Diverse Pincer Complexes from a Diphosphine-Phosphine Oxide." *Organometallics* 2013 32(4): 1121-1128.
61. Gloaguen, Y., et al., "Reactivity of a mononuclear iridium (I) species bearing a terminal phosphido fragment embedded in a triphosphorus ligand." *Inorg. Chem.* 2013 52(4): 1682-1684.
62. Mazzeo, M., et al., "Phosphido Pincer Complexes of Palladium as New Efficient Catalysts for Allylation of Aldehydes." *Organometallics* 2008 27(22): 5741-5743.
63. Mazzeo, M., et al., "Phosphido pincer complexes of platinum: synthesis, structure and reactivity." *Dalton Trans* 2011 40(35): 9026-9033.
64. Pan, B. F., et al., "Coordination of an N-Heterocyclic Phosphenium Containing Pincer Ligand to a Co(CO)(2) Fragment Allows Oxidation To Form an Unusual N-Heterocyclic Phosphinito Species." *Organometallics* 2011 30(21): 5560-5563.
65. Pan, B., et al., "Heterolytic addition of E-H bonds across Pt—P bonds in Pt N-heterocyclic phosphenium/phosphido complexes." *Dalton Trans* 2012 41(30): 9083-9090.
66. Wife, R. L., et al., "Phosphine Oxide Anions in the Synthesis of Phosphine Ligands." *Synthesis* 1983 1983(01): 71-73.
67. Baccolini, G., et al., "A New Performance of the Reaction of PCl3/AlCl3 with Anisoles—One-Pot and Multi-Step Syntheses of a New Fused-Ring System [1,2,3]Benzoxadiphospholo[2,3-b][1,2,3]benzoxadiphosphole." *European Journal of Organic Chemistry* 2001 2001(12): 2229-2233.
68. Kurmaev, D. A., et al., "Coordination compounds of chromium (+3) and vanadium (+3) and (+5) with 2,6-bis(diphenylhydroxymethyl)pyridyl ligand: Synthesis and study of catalytic activity in the polymerization of ethylene." *Inorganica Chimica Acta* 2013 396(0): 136-143.
69. Villanneau, R., et al., "Bisorganophosphonyl and -Organoarsenyl Derivatives of Heteropolytungstates as Hard Ligands for Early-Transition-Metal and Lanthanide Cations." *European Journal of Inorganic Chemistry* 2013 2013(10-11): 1815-1820.
70. Tong, L. H., et al., "The coordination chemistry of unsymmetric N-capped tripodal NO3 ligands with iron(III), oxovanadium(V) and dioxo-molybdenum(VI) metal centres." *Inorganica Chimica Acta* 2012 383(0): 91-97.
71. North, M., et al., "Asymmetric cyanohydrin synthesis using an aluminium(salan) complex." *Tetrahedron: Asymmetry* 2012 23(15-16): 1218-1225.
72. Fletcher, R., "Practical Methods of Optimization". 1987, New York: Wiley.
73. Cao, Y., et al., "Molecular (hyper)polarizabilities computed by pseudospectral methods." *J Chem Phys* 2005 122(10): 104102.

The invention claimed is:

1. A catalytic matrix for activation of a R—H bond in a R—H substrate wherein R is an alkyl group, the R—H bond having an R—H bond enthalpy, the catalytic matrix comprising a plurality of catalytic cores of Formula (III):

(III)

wherein:
Y1 is NH, Y1 being capable of forming a Y1-H single bond with the H from the R—H substrate, and the Y1-H single bond having a Y1-H enthalpy;
X is P;
Z is NH;
Y2 is NH;
M is V;
i is 1-2;
j is 0-1; and
k is 0-1;
wherein Y1, X, Z, M, and Y2 are selected such that the Y1-H single bond enthalpy is equal or lower than the R—H single bond enthalpy;
and wherein the M and X of each catalytic core of the plurality of the catalytic cores of Formula (III) are connected to a supporting moiety A, wherein the supporting moiety A links the M and the X of each catalytic core of the plurality of the catalytic cores of Formula (III), the supporting moiety A configured to form a framework presenting Y1 of each catalytic core of the plurality of the catalytic cores for reaction with a substrate R—H wherein A is a moiety of formula (IV):

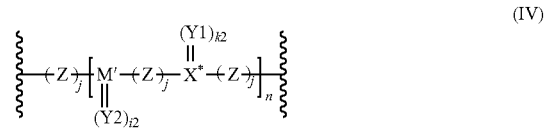

(IV)

in which:

is an α and/or β bond;
M' is V;
Y1 is NH;
Y2 is NH;
Z is NH; and
X* is P,
and wherein n is 1-6, and j, i2, and k2 are independently 0 or 1, and wherein a terminal Z of the moiety of Formula IV is linked to an M or an X element of a catalytic core of Formula III.

2. The catalytic matrix of claim 1, wherein the matrix comprises at least 5% of a first catalytic core, at least 30-50% of a second catalytic core, at least 45-65% of a third catalytic core.

3. The catalytic matrix of claim 1, wherein the framework comprises a plurality of layers, each layer of the plurality of layer presenting one or more catalytic cores configured to activate one or more R—H substrate.

4. The catalytic matrix of claim 3, wherein each layer of the plurality of layers presents between 0.1 and 10% of a first catalytic core, between 10 and 50% of a second catalytic core, at least 40% of a third catalytic core.

5. The catalytic matrix of claim 1, wherein at least 50% of the M and X of A and the catalytic core are bonded to =Y2 and =Y1 groups, respectively.

6. The catalytic matrix of claim 1, wherein the catalytic matrix comprises layers each comprising a plurality of groups of formula (III) having different values for i, j and/or k.

7. The catalytic matrix of claim 1, wherein a difference between the Y1-H bond enthalpy and the R—H bond enthalpy is less than a threshold value in a model system.

8. The catalytic matrix of claim 1, wherein the catalytic matrix comprises layers each comprising a pluralities of groups of formula (IV) having different values of j, i2 and k2.

9. The catalytic matrix of claim 8, wherein the threshold value is between about 10 and 25 kcal/mol.

\* \* \* \* \*